(12) United States Patent
Kappes et al.

(10) Patent No.: US 6,555,342 B1
(45) Date of Patent: Apr. 29, 2003

(54) FUSION PROTEIN DELIVERY SYSTEM AND USES THEREOF

(75) Inventors: John C. Kappes, Birmingham, AL (US); Xiaoyun Wu, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/460,548

(22) Filed: Dec. 14, 1999

Related U.S. Application Data

(63) Continuation-in-part of application No. 09/089,900, filed on Jun. 3, 1998, now abandoned.

(51) Int. Cl.$^7$ .................. C12P 21/00; C12N 15/867; C12N 15/63; C07H 21/04
(52) U.S. Cl. ............. 435/69.1; 435/320.1; 435/455; 435/456; 435/457; 435/5; 435/6; 435/7.1; 435/91.4; 435/91.41; 435/91.42; 435/325; 435/366; 435/69.7; 536/23.1; 536/23.4; 536/23.72; 536/24.1
(58) Field of Search ................... 435/320.1, 455, 435/456, 457, 5, 6, 7.1, 91.4, 91.41, 91.42, 325, 366; 536/23.1, 23.4, 23.72, 24.1

(56) References Cited

U.S. PATENT DOCUMENTS

| | | | |
|---|---|---|---|
| 5,175,099 A | 12/1992 | Wills | |
| 5,378,806 A | 1/1995 | Willis | |
| 5,665,577 A | 9/1997 | Sodroski et al. | |
| 5,861,161 A | 1/1999 | Cohen et al. | |
| 5,981,276 A | 11/1999 | Sodroski et al. | |
| 6,043,081 A | 3/2000 | Cohen et al. | |
| 6,365,150 B1 | 4/2002 | Leboulch et al. | |

FOREIGN PATENT DOCUMENTS

| | | |
|---|---|---|
| DE | 275259 | 1/1990 |
| EP | 356021 | 2/1990 |
| WO | 90/15875 | 12/1990 |
| WO | 92/00987 | 1/1992 |
| WO | 93/24632 | 12/1993 |
| WO | 93/25235 | 12/1993 |
| WO | 94/17825 | 8/1994 |
| WO | 95/16705 | 6/1995 |
| WO | 95/26361 | 10/1995 |
| WO | 96/07741 | 3/1996 |
| WO | 96/11696 | 4/1996 |
| WO | 97/36481 | 10/1997 |
| WO | WO 99/58701 A1 | 11/1999 |

OTHER PUBLICATIONS

Akari, et al., "Biological characterization of human immunodeficiency virus type 1 and 2 mutants in human peripheral blood mononuclear cells," *Arch. Virol.* 123:157–167 (1992).

Alton, et al., "Nucleotide sequence analysis of the chloramphenicol resistance transposon Tn9," *Nature* 282:864–869 (1979).

Ansari,–Lari, et al., "Expression of Human Immunodeficiency Virus Type 1 Reverse Transcriptase in trans during Virion Release and after Infection," *J. Virol.* 70:3870–3875 (1996).

Ansari–Lari, et al., "Analysis of Human Immunodeficiency Virus Type 1 Integrase Mutants," *Virology* 211:332–335 (1995).

Balotta, et al., "Antisense Phosphorothioate Oligodeoxynucleotides Targeted to the vpr Gene Inhibit Human Immunodeficiency Virus Type 1 Replication in Primary Human Macrophages," J. Virol. 67(7):4409–4414 (Jul. 1993).

Bukovsky, et al., "Lack of Integrase Can Markedly Affect Human Immunodeficiency Virus Type 1 Particle Production in Presence of an Active Viral Protease," *J. Virol.* 70:6820–6725 (1996).

Charneau, et al., "HIV–1 Reverse Transcription: A Termination Step at the Center of the Genome," *J. Mol. Biol.* 241:651–662 (1994).

Cohen, et al., "Human Immunodeficiency Virus vpr Product Is a Virion–Associated Regulatory Protein," *J. Virol.* 64(6):3097–3099 (Jun. 1990).

Cohen, et al., "Identification of HIV–1 vpr Product and Function," *J. Acq. Immune Def. Synd.* 3:11–18 (1990).

Dedera, et al., "Viral Protein R of Human Immunodeficiency Virus Types 1 and 2 Is Dispensable for Replication and Cytopathogenicity in Lymphoid Cells," *J. Virol.* 63(7): 3205–3208 (Jul. 1989).

Derosiers, "HIV with Multiple Gene Deletions as a Live Attenuated Vaccine for AIDS," AIDS Research and Human Retroviruses, 8(3): 411–421 (Nov. 3, 1992).

Di Marzio, et al., "Mutational Analysis of Cell Cycle Arrest, Nuclear Localization, and Virion Packaging of Human Immunodeficiency Virus Type 1 Vpr," *J. Virol.* 69(12): 7909–7916 (Dec. 1995).

(List continued on next page.)

*Primary Examiner*—David Guzo
(74) *Attorney, Agent, or Firm*—Alston & Bird LLP

(57) ABSTRACT

The present invention provides a composition of matter, comprising: DNA encoding a viral Vpx protein fused to DNA encoding a protein. In another embodiment of the present invention, there is provided a composition of matter, comprising: DNA encoding a viral Vpr protein fused to DNA encoding a protein. The present invention further provides DNA, vectors and methods for expressing a lentiviral pol gene in trans, independent of the lentiviral gag-pol. A gene transduction element is optionally delivered to a lentiviral vector according to the present invention. Also provided are various methods of delivering a virus inhibitory molecule to a target in an animal. Further provided is a pharmaceutical composition.

108 Claims, 28 Drawing Sheets

(4 of 28 Drawing Sheet(s) Filed in Color)

OTHER PUBLICATIONS

Engelman, et al., "Multiple Effects of Mutations in Human Immunodeficiency Virus Type 1 Integrase on Viral Replication," *J. Virol.* 69:2729–2736 (1995).

Finer, et al., "A High–Efficiency Retroviral Transduction System for Primary Human T Lymphocytes," *Blood* 83:43–50 (1994).

George, et al., "Current Methods in Sequence Comparison and Analysis," Macromolecule Sequencing and Synthesis, Selected Methods and Applications 127–149.

Gibbs, et al., Construction and In Virto Properties of SIV MAC Mutants with Deletions in "Nonessential" *Genes, AIDS Research and Human Retroviruses*, 10(5);607–616 (Nov. 5, 1994).

Gottlinger, et al., "Effect of mutations affecting the p6 gag protein on human immunodeficiency virus particle release," *Proc. Natl. Acad. Sci.* 88:3195–3199 (Apr. 1991).

Guyader, et al., "VPX mutants of HIV–2 are infectious in established cell lines but display a severe defect in peripheral blood lymphocytes," *The EMBO Journal* 8(4): 1169–1175 (1989).

Hattori, et al., "The HIV–2 Vpr Gene is Essential for Macrophage Infections," p. 309 (Abstract).

Hattori, et al., "The Human Immunodeficiency Virus Type 2 vpr Gene is Essential for Productive Infection of Human Macrophages," *Proc. Natl. Acad. Sci. USA* 87:8080–8084 (Oct. 1990).

He, et al., "Human Immunodeficiency Virus Type 1 Viral Protein R (Vpr) Arrests Cells in the G2 Phase of the Cell Cycle by Inhibiting p34cdc2 Activity," *J. Virol.* 69(11):6705–6711 (Nov. 1995).

Heinzinger, et al., The Vpr protein of human immunodeficiency virus type 1 influences nuclear localization of viral nucleic acids in nondividing host cells, *Proc. Natl. Acad. Sci. USA* 91:7311–7315 (Jul. 1994).

Hoch, et al., "vpr Deletion Mutant of Simian Immunodeficiency Virus Induces AIDS in Rhesus Monkeys," *J. Virol.* 69(8):4807–4813 (Aug. 1995).

Horton, et al., "HIV–2 Viral Protein X Association with the Gag p27 Capsid Protein," *Virology* 199:453–457 (1994).

Hu, et al., "Analysis and function of viral protein X (VPX) of HIV–2", *Virol.* 173:624–630 (1989).

Huang, et al., "Mutational Analysis of the Murine AIDS–Defective Viral Genome Reveals a High Reversion Rate in Vivo and A Requirement for an Intact Pr60gag Protein for Efficient Induction of Disease," *Journal of Virology* 60–68 (Jan. 1995).

Huang, et al., "P6Gag Is Required for Particle Production from Full–Length Human Immunodeficiency Virus Type 1 Molecular Clones Expressing Protease," *Journal of Virology* 6810–6818 (Nov. 1995).

Hutchinson, et al., utagenesis at a Specific Position in a DNA Sequence, *J. Biol. Chem* 253:6651.

Kappes, et al., "Human Immunodeficiency Virus Type 2 vpx Protein Augments Viral Infectivity," *Virology* 184:197–209 (1991).

Kappes, et al., "Identification of a Novel Retroviral Gene Uniquie to Human Immunodeficiency Virus Type 2 and Simian Immunodeficiency Virus SIV MAC," *J. Virol.* 62(9): 3501–3505 (Sep. 1988).

Kappes, et al., "Intracellular Transport and Virion Incorporation of vpx Requires Interaction with Other virus Type–Specific Components," *J. Virol.* 193:222–233 (1993).

Kappes, et al., "Targeting foreign proteins to HIV particles via fusion with Vpr and Vps," *J. Biol. Chem. Suppl.* 21(A): 395 (Jan. 1994).

Kappes, et al., "The HIV Vpx and Vpr genes mediate virion incorporation of nuclease fusion proteins," *J. Biol. Chem. Suppl.* 21(A):162 (Mar. 1995).

Kappes, et al., Intracellular Transport and Virion Incorporation of vpx Requires Interaction with other Virus Type–Specific Components, *J. Virol.* 193:222–223 (1993).

Kewalramani, et al., "Protein Stability Influences Human Immunodeficiency Virus Type 2 Vpr Virion Incorporation and Cell Cycle Effect," *Virology* 218:326–334 (1996).

Kewalramani, et al., "Vpx Association with Mature Core Structures of HIV–2," *Virology* 218:159–168 (1996).

Kirchhoff, et al., "Upstream U3 Sequences in Simian Immunodeficiency Virus are Selectively Deleted in Vivo in the Absence of an Intact nef Gene," *J. Virol.* 68(3): 2031–2037 (Mar. 1994).

Kondo, et al., "The p6gag Domain of Human Immunodeficiency Virus Type 1 is Sufficient for the Incorporation of Vpr into Heterolous Viral Particles," *J. Virol.* 69(5):2759–2764 (May 1995).

Lang, et al., "Importance of vpr for Infection of Rhesus Monkeys with Simian Immunodeficiency Virus," *J. Virol.* 67(2): 902–912 (Feb. 1993).

Lavallee, et al., "Requirement of the Pr55gag Precursor for Incorporation of the Vpr Product into Human Immunodeficiency Virus Type 1 Viral Particles," *J. Virol.* 68(3) 1926–1934 (Mar. 1994).

Lee, et al., "The role of vpx in the life cycle of HIV–2," submitted to the Proceedings of the Third Annual "Colloque Des Cent Gardes" (1988).

Levy, et al., "Extracellular Vpr Protein Increase Cellular Permissiveness to Human Immunodeficiency Virus Replication and Reactivates Virus from Latency," *J. Virol.* 69(2) 1243–1252 (Feb. 1995).

Levy, et al., "Induction of Cell Differentiation by Human Immunodeficiency Virus 1 vpr," *Cell* 72:541–550 (Feb. 26, 1993).

Levy, et al., "Serum Vpr regulates productive infection and latency of human immunodeficiency virus type 1," *Proc. Natl. Acad. Sci. USA* 91:10873–10877 (Nov. 1994).

Liu, et al., "Incorporation of Functional Human Immunodeficiency Virus Type 1 Integrase into Virions Independent of the Gag/Pol Precursor Protein," (Revised Manuscript, #JVI 548–97) *J. Virology* 71:7704–7710 (1997).

Liu, et al., "The Vif Protein of Human and Simain Immunodeficiency Viruses Is packaged into Virions and Associates with Viral Core Structures," *J. Virol.* 69:7630–7638 (1995).

Lu, et al., "A Leucine Triplet Repeat Sequence (LXX)4 in p6gag Is Important for Vpr Incorporation into Human Immunodeficiency Virus Type 1 Particles," *J. Virol.* 69(11):6873–6879 (1995).

Lu, et al., "A Leucine Triplet Repeat Sequence LXX4 in p6gag Is Important for Vpr Incorporation into Human Immunodeficiency Virus Type 1 Particles," *J. Virol.* 69(11): 6873–6879 (Nov. 1995).

Lu, et al., "Human Immunodeficiency Virus Type 1 Viral Protein R Localization in Infected Cells and Virions," *J. Virol.* 67(11): 6542–6552 (Nov. 1993).

Macreadie, et al., "A domain of human immunodeficiency virus type 1 Vpr containing repeated H(S/F)RIG amino acid motifs causes cell growth arrest and Structural defects," *Proc. Natl. Acad. Sci. USA* 92:2770–2274 (Mar. 1995).

Mahalingam, et al., "Functional Analysis of HIV–1 Vpr: Indentification of Determinants Essential for Subcellular Localization," *Virology* 212:331–339 (1995).

Mahalingam, et al., "HIV–1 Vpr interacts with human 34–kDa mov34 homologue, a cellular factor linked to the G2/M phase transition of the mammalian cell cycle," *Proc. Natl. Acad. Sci. USA* 95:3419–3424 (Mar. 1998).

Mahalingam, et al., "Identification of Residues in the N–Terminal Acidic Domain of HIV–1 Vpr Essential for Virion Incorporation," *Virology* 207:297–302 (1995).

Mahalingam, et al., "The Carboxy–Terminal Domain Is Essential for Stability and Not for Virion Incorporation of HIV–1 Vpr into Virus Particles," *Virology* 214:647–652 (1995).

Marcon, et al., "Dispensable Role of the Human Immunodeficiency Virus Type 2 Vpx Protein in Viral Replication," *J. Virol.* 65 (7): 3938–3942 (Jul. 1991).

Matsuda, et al., "A virion–specific inhibitory molecule with therapeutic potential for human immunodeficiency virus type 1," *Proc. Natl. Acad. Sci. USA* 90:3544–3548 (Apr. 1993).

Naldini, et al., *Science* 272: 263–267 (1996).

Natsoulis and Boeke, "New antiviral strategy using capsid–nuclease fusion proteins," *Nature* 352:632–635 (1991).

Natsoulis, et al., "Targeting of a nuclease to murine leukemia virus capsids inhibits viral multiplication," *Proc. Nat. Acad. Sci. USA* 92:364–368 (Jan. 1995).

Ogawa, et al., "Mutational Analysis of the Human Immunodeficiency Virus vpr Open Reading Frame," *J. Virol.* 63(9):4110–4114 (Sep. 1989).

Orkin, et al., "Report and Recommendations of The Panel to Assess the NIH Investment in Research On Gene Therepy," NIH Panel Report. Dec. 1995. Entire Report.

Park, et al., "Amino Acid Sequence Requirements for the Incorporation of the Vpx Protein of Simian Immunodeficiency Virus into Virion Particles," *J. Acq. Immune Def. Synd.* 10:506–510 (1995).

Park, et al., "Targeting a foreign protien into virion particles by fusion with the Vpx protein of simian immunodeficiency virus," *J. Acq. Immunoe Def. Synd.,* 11(4):341–50 (Apr. 1, 1996).

Paxton, et al., "Incorporation of Vpr into Human Immunodeficiency Virus Type 1 Virion: Requirement for the p6 Region of faf and Mutational Analysis," *J. Virol.* 67(12):7229–7237 (1993).

Paxton, et al., "Incorporation of Vpr into Human Immunodeficiency Virus Type 1 Virions: Requirement for the p6 Region of gag and Mutational Analysis," *J. Virol.* 67(12) 7229–7237 (Dec. 1993).

Percy, et al., "A poliovirus replicon containing the chloramphenicol acetyltransferase gene can be used to study the replication and encapsidation of poliovirus RNA," *J. Virol.*66(8): 5040–5046 (Aug. 1992).

Re, et al., "Human Immunodeficiency Virus Type 1 Vpr Arrests the Cell Cycle in G2 by Inhibiting the Activation of p34cdc2–Cyclin B," *J. Virol.* 69(11):6859–6864 (Nov. 1995).

Rogel, et al., "The Human Immunodeficiency virus type 1 vpr Gene Prevents Cell Proliferation during chronic Infection," *J. Virol.* 69(2): 882–888 (Feb. 1995).

Sato, et al., "Targeting of Chrolamphenicol Acetyltransferase to Human Immunodeficiency Virus Particles via Vpr and Vpx," *Microbiol. Immunol.* 39(12): 1015–1019 (1995).

Schnell, et al., "Construction of a Novel Virus That Targets HIV–1–Infected Cells and Controls HIV–1 Infections," *Cell Press* 90:849–857 (1997).

Shibata, et al., "Construction and Characterization of an Infectious DNA Clone and of Mutants of Simian Immunodeficiency Virus Isolated from the African Green Monkey," *J. Virol.* 64(1):307–312 (Jan. 1990).

Shibata, et al., "Generation of a Chimeric Human and Simain Immunodeficiency Virus Infectious to Monkey Peripheral Blood Mononuclear Cells," *J. Virol.* 65(7):3514–3520 (Jul. 1991).

Shibata, et al., "Mutational Analysis of the Human Immunodeficiency Virus Type 2 (HIV–2) Genome in Relation to HIV–1 and Simian Immunodeficiency Virus SIVabm," *J. Virol.* 64(2):742–747 (Feb. 1990).

Schumann, et al., "Therapeutic Effect of Gag–Nuclease Fusion Protein on Retrovirus–Infected Cell Cultures," *J. Virol.* 70:4329–37 (1996).

Smith, et al., "Single–step purification of polypeptides expressed in *Escherichia coli* as fusions with glutathione S–transferase," *Gene* 67:31–40 (1988).

Stewart, et al., "Human Immunodeficiency Virus Type 1 Vpr Induces Apoptosis following Cell Cycle Arrest," *J. Virol.* 71:5579–5592 (1997).

Tristem, et al., "Evolution of the Primate Lentiviruses: Evidence From Vpx and Vpr," *EMBO J.* 11:3405–3412 (1992).

Tristem, et al., "Origin of Vpx In Lentiviruses," *Nature* 347:341–342.39 (1990).

Trono. "HIV Accessory Proteins: Leading Roles for the Supporting Cast," *Cell* 82:189–192 (Jul. 28, 1995).

Wang, et al., "Particle assembly and Vpr expression in human immunodeficiency virus type 1–infected cells demonstrated by immunoelectron microscopy," *Journal of General Virology* 75:2607–2614 (1994).

Westervelt, et al., "Dual Regulation of Silent and Productive Infection in Monocytes by Distinct Human Immunodificiency Virus Type 1 Determininants," *J. Virol.* 66(6): 3925–3931 (Jun. 1992).

Wong–Staal, et al., "Human Immunodeficiency Virus: The Eighth Gene," *Aids Research and Human Retroviruses* 3(1) (1987).

Wu, et al., "Functional RT and IN Incorporated Into HIV–1 Particles Independent of the Gag/Pol Precursor Protein," *J. Virol.* 68:6161–6169 (1994).

Wu, et al., "Functional RT and IN Incorporated Into HIV–1 particles independent of the Gag/Pol precursor protein," *EMBO J.* 16:5113–5122 (1997).

Wu, et al., "Functional RT and IN incorporated Into HIV–1 Particles Independent of the Gag/Pol Precursor Protein," *EMBO J.* 16:0: 101–109 (1997).

Wu, et al., "HIV/SIV Virion Associated Accessory Genes Mediate Efficient Packaging of Nuclease Fusion Proteins Into The Virus Particle," The First National Conference on Human Retroviruses and Related Infections, Washington DC (1993).

Wu, et al., "Inhibition of HIV–1 replication by targeting Vpr fusion proteins to virions," *Biol. Abstr./BBM* 47(4):MT–323 (Jan. 1995).

Wu, et al., "Inhibition of Human and Simian Immunodeficiency Virus Protease Function by Targeting Vpx–Protease–Mutant Fusion Protein Into Viral Particles," *J. Virol.* 3378–3384 (1996).

Wu, et al., "Localization of the Vpx Packaging Signal within the C Terminus of the Human Immunodeficiency Virus Type 2 Gag Precursor Protein," *J. Virol.* 68(10):6164–6169 (Oct. 1994).

Wu, et al., "Multiple Glycoproteins Synthesized by the Smallest RNA Segment (S10) of Bluetongue Virus," *J. Virol.* 66:7104–7112 (1992).

Wu, et al., "Targeting foreign proteins to human immunodeficiency viruses types 1 and 2 via fusion with Vpr and Vpx," *Biol. Abstr./RRM* 47(4):MT–323 (Jan. 1995).

Wu, et al., "Targeting Foreign Proteins to Human Immunodeficiency Virus Particles Via Fusion with Vpr and Vpx," (Revised Manuscript, #JVI 1529–94), *J. Virology* 69:3389–3398 (1995).

Yao, et al., "Mutagenic Analysis of Human Immunodeficiency Virus Encodes a Virion–Associated Protein," *J. Virol.* 64(11):5688–5693 (Nov. 1990).

Yu, et al., "Open Reading Frame vpr of Simian Immunodeficiency Virus Facilitates Efficient viral Replication in Fresh Lymphocytes and Macrophages," *J. Virol.* 65(9):5088–5091 (Sep. 1991).

Yu, et al., "Vpx of Simian Immunodeficiency Virus Is Localized Primarily Outside the Virus Core in Mature Virions," *J. Virol.* 67(7): 4386–4390 (Jul. 1993).

Yuan, et al., "Human Immunodeficiency Virus vpr Gene Encodes a Virion–Associated Protein," *AIDS Research and Human Retroviruses* 6(11) 1265–1271 (1990).

Zhang, et al., "Rate and Mechanism of Nonhomologous Recombination During a Single Cycle of Retroviral Replication," *Science* 259:234–238 (1993).

Zhao, et al., "Biochem. Mechanism of HIV–1 Vpr function," *J. Biol. Chem.* 269: 15577–15582 (Jun. 1994).

Zhao, et al., "Biochemical Mechanism of HIV–1 Vpr Function: Oligomerization Mediated by the N–Terminal Domain," *J. Biol. Chem.* 269: 32131–32137 (Dec. 1994).

Zufferey, "Woodchuck Hepatitis Virus Posttranscriptional Regulatory Element Enhances Expression of Transgenes Delivered by Retroviral Vectors," *J. Virol.* 73:2886–2892 (1999).

Fletcher, T.M. III, et al., "Complementation of Integrase Function in HIV–1 Virons," Fourth Conference on Retroviruses and Opportunistic Infections, Jan. 22, 1997, Abstract No. 394.

Fletcher, T.M. III, et al., "Complementation of Integrase Function in HIV–1 Virons," Third Conference on Retroviruses and Opportunistic Infections, Jan. 28, 1996.

Kappes, J.C., et al., "Infectious Human Immunodeficiency Virus Type 1 Derived From Reverse Transcriptase (RT) and Integrase (IN) Minus Provirus Trans Complemented with VPR–RT and–IN Fusion Protein," Keystone Symposia, Apr. 8, 1997.

Liu, H., et al., Replication of Integrase Mutant HIV–1 Complemented in Trans With Heterologous in Protein, Cold Spring Harbor Meeting on Retroviruses, May 20, 1997.

Wakefield, I.K., et al., "Destroying HIV from Within," Fourth Conference on Retroviruses and Opportunistic Infections, Jan. 22, 1997.

Wu, X., et al., "Incorporation of Functional RT Protein Into HIV–1 Particles by Trans Expression as a VPR–RT Fusion Protein," $36^{th}$ Interscience Conference on Antimicrobial Agents and Chemotherapy, Sep. 22, 1997.

Wu, X., et al., "Infectious Human Immunodeficiency Virus Type 1 Derived From Reverse Transcriptase (RT) and Integrase (IN) Minus Provirus Complemented With RT and in IN Trans," Cold Spring Harbor Conference on Retroviruses, May 20, 1997.

Wu, X., et al., "HIV–1 DNA Synthesis in Infected Cells Requires IN Protein," Cold Spring Harbor Conference on Retroviruses, May 20, 1997.

Wu, X., et al., "Virion Incorporation of Vpr–RT Fusion Protein Rescues Replication of RT–Defective HIV–1," Third Conference on Retroviruses and Opportunistic Infections, Jan. 28, 1996.

Wu, X., et al., "Virion Incorporation of VPR–RT Fusion Protein Rescues Replication of RT–Defective HIV–1," Cold Spring Harbor Conference on Retroviruses, May. 21, 1996.

Fletcher, T.M., et al., "Complementation of Integrase Function in HIV–1 Virons," The EMBO Journal, 1997, pp. 5123–5138, vol. 16(16).

Yu, S., et al., "Human Foamy Virus Replication: A Pathway Distinct from That of Retroviruses and Hepadnaviruses," *Science*, 1996, pp. 1579–1582, vol. 271.

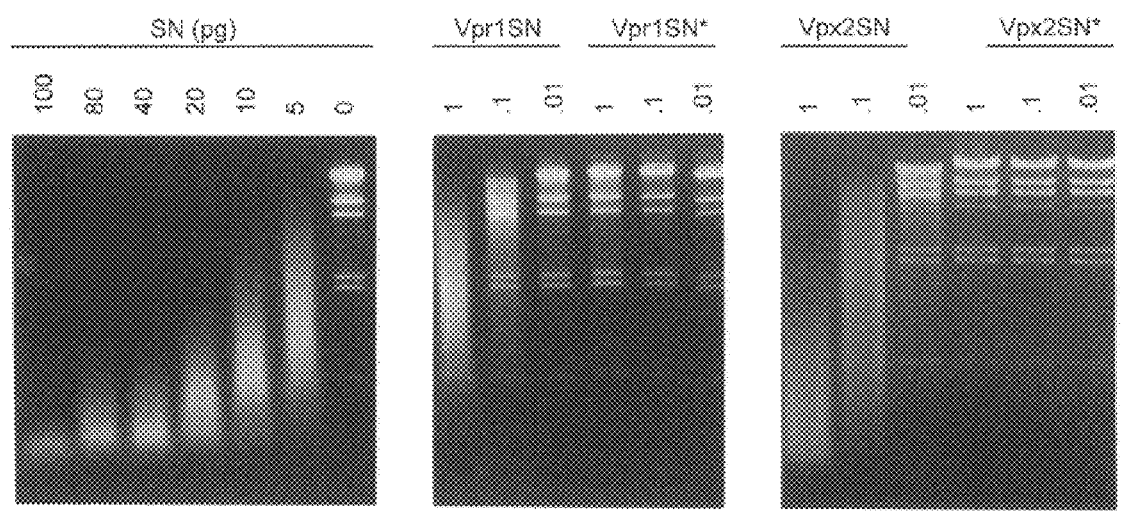
*FIG. 6A*   *FIG. 6B*   *FIG. 6C*

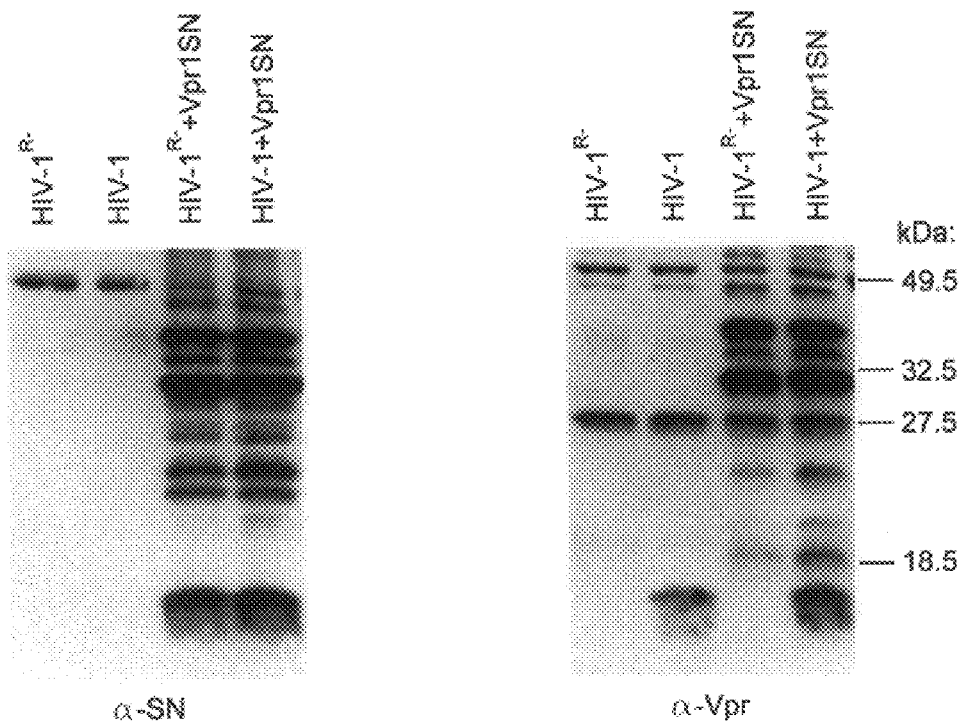
*FIG. 8A*
*FIG. 8B*
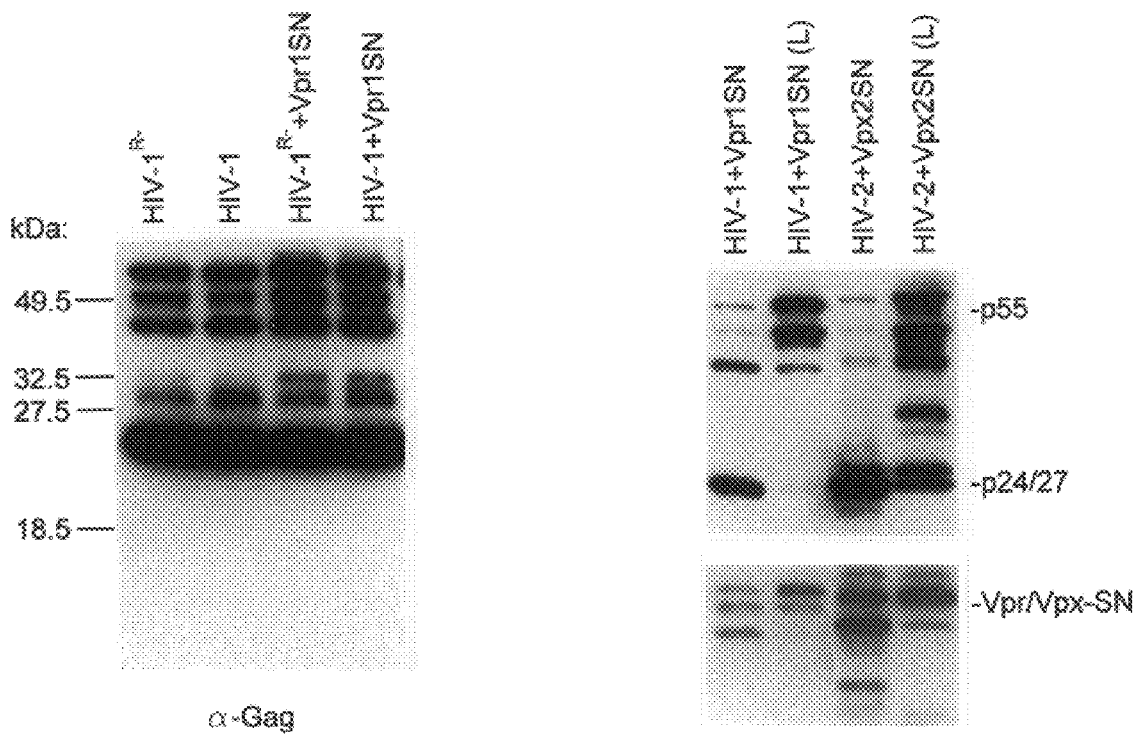
*FIG. 8C*
*FIG. 9*

HIV-1 GENOME
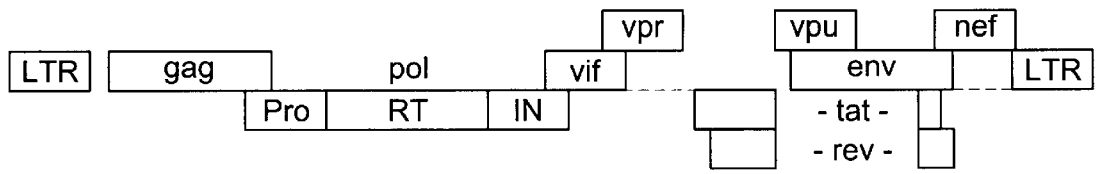
FIG. 12A
LENTIVIRUS VECTOR PLASMID EXPRESSION SYSTEM
MULTIPLY DELETED PACKAGING PLASMID
(pΔ8.2)
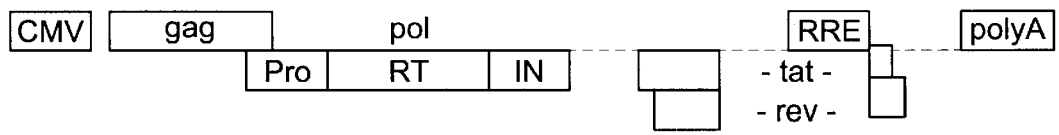
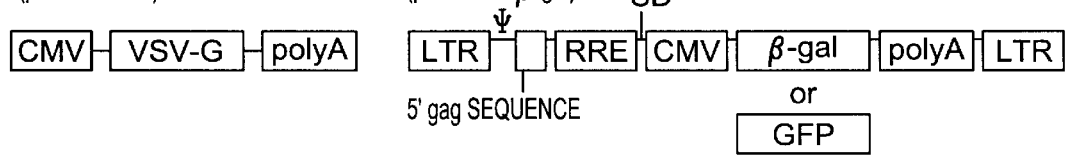
FIG. 12B
TRANS-LENTIVIRAL VECTOR EXPRESSION SYSTEM
TRANS-LENTIVIRAL PACKAGING PLASMID
(pCR-gag-pro)
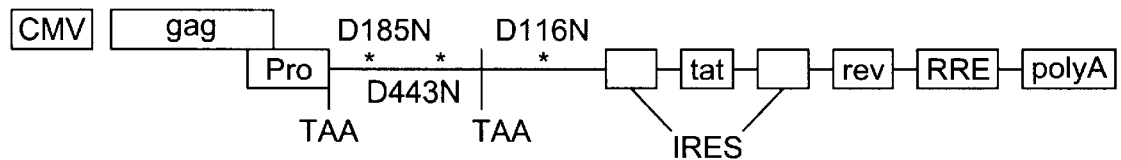
TRANS-LENTIVIRAL ENZYMATIC PLASMID
(pLR2P-vpr-RT-IN)
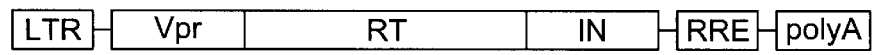
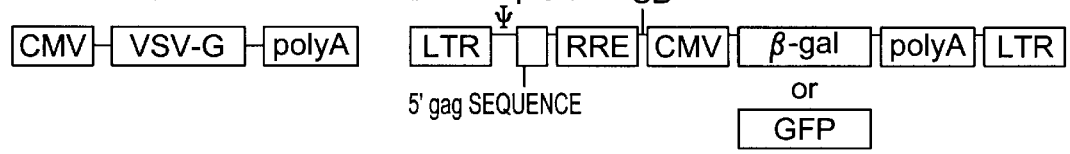
FIG. 12C pHR-CFTR

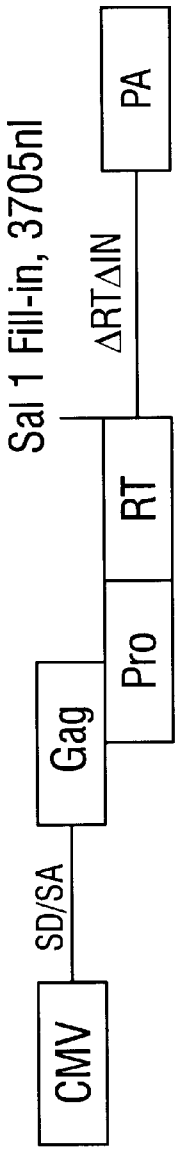
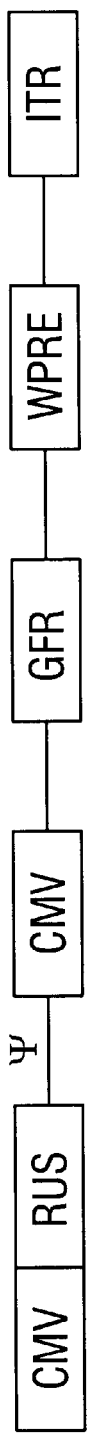
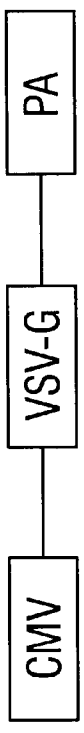
FIG. 21A  pCMV, Gag-Pro
FIG. 21B  pCMV, GagNC-RT-IN
FIG. 21C  PRT-CMV,GFP, WPRE (the original vector* was modified to contain the WPRE)
FIG. 21D  pMD-G

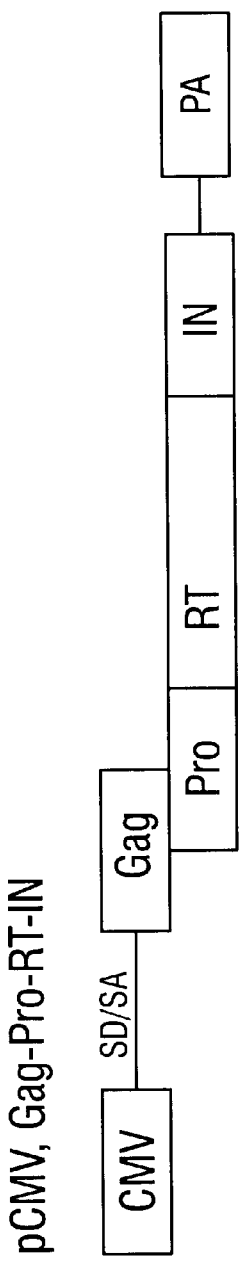
FIG. 22A   pCMV, Gag-Pro-RT-IN
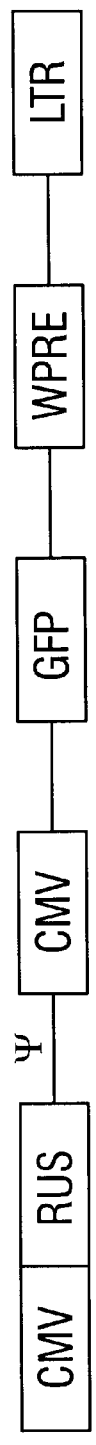
FIG. 22B   pRT-CMV, GFP, WPRE (the original vector* was modified to contain the WPRE)
FIG. 22C   pMD-G

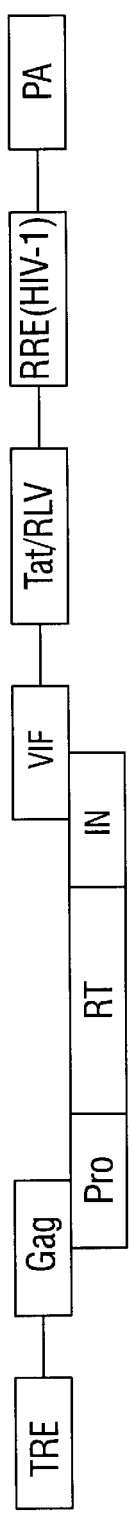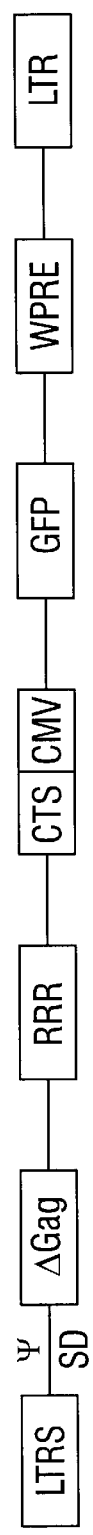
FIG. 23A   pTRE, Gag-Pro-RT-IN
FIG. 23B   PHR-CTS, CMV, GFP, WPRE
FIG. 23C   pMD-G

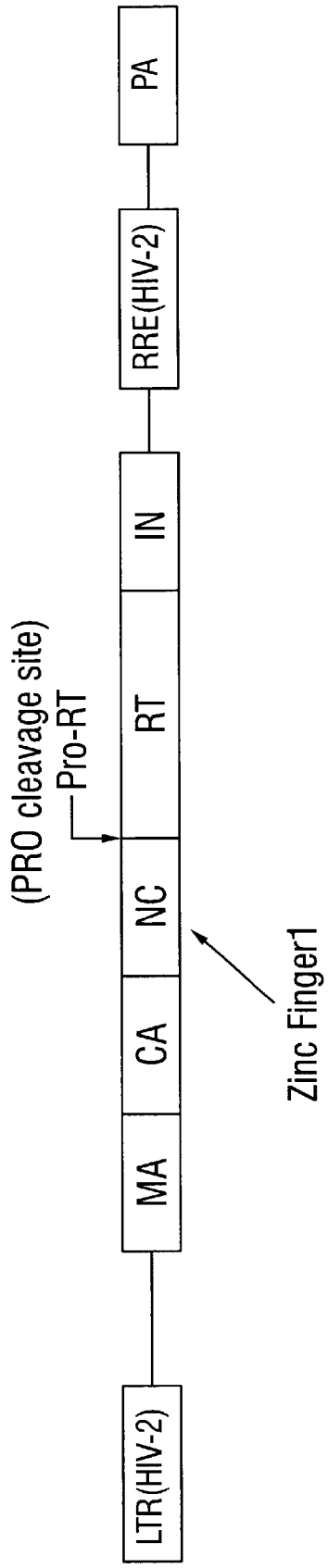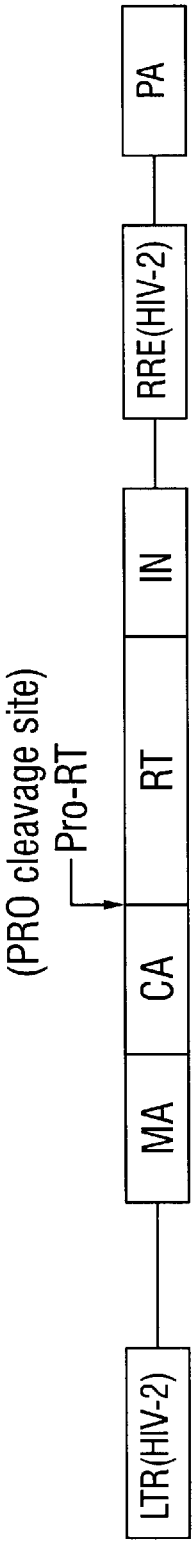
*FIG. 24B*
*FIG. 24C*

SEQUENCE LISTING

<160> NUMBER OF SEQ ID NOS: 18

<210> SEQ ID NO 1
<211> LENGTH: 27
<212> TYPE: DNA
<213> ORGANISM: Artificial Sequence
<220> FEATURE:
<223> OTHER INFORMATION: oligonucleotide primers

<400> SEQUENCE: 1
gccacctttg tcgactgtta aaaaact                                27

<210> SEQ ID NO 2
<211> LENGTH: 24
<212> TYPE: DNA
<213> ORGANISM: Artificial Sequence
<220> FEATURE:
<223> OTHER INFORMATION: oligonucleotide primers

<400> SEQUENCE: 2
gtcctaggca agcttcctgg atgc                                   24

<210> SEQ ID NO 3
<211> LENGTH: 25
<212> TYPE: DNA
<213> ORGANISM: Artificial Sequence
<220> FEATURE:
<223> OTHER INFORMATION: oligonucleotide primers

<400> SEQUENCE: 3
aaggagagcc atgggtgcga gagcg                                  25

<210> SEQ ID NO 4
<211> LENGTH: 26
<212> TYPE: DNA
<213> ORGANISM: Artificial Sequence
<220> FEATURE:
<223> OTHER INFORMATION: oligonucleotide primers

<400> SEQUENCE: 4
ggggatccct ttattgtgac gagggg                                 26

<210> SEQ ID NO 5
<211> LENGTH: 25
<212> TYPE: DNA
<213> ORGANISM: Artificial Sequence
<220> FEATURE:
<223> OTHER INFORMATION: oligonucleotide primers

<400> SEQUENCE: 5
attgtgggcc atgggcgcga gaaac                                  25

<210> SEQ ID NO 6
<211> LENGTH: 24
<212> TYPE: DNA
<213> ORGANISM: Artificial Sequence
<220> FEATURE:
<223> OTHER INFORMATION: oligonucleotide primers

<400> SEQUENCE: 6
gggggggccc tactggtctt ttcc                                   24

<210> SEQ ID NO 7
<211> LENGTH: 28

```
<212> TYPE: DNA
<213> ORGANISM: Artificial Sequence
<220> FEATURE:
<223> OTHER INFORMATION: oligonucleotide primers

<400> SEQUENCE: 7
gaagatctac catggaagcc ccagaaga                                              28

<210> SEQ ID NO 8
<211> LENGTH: 39
<212> TYPE: DNA
<213> ORGANISM: Artificial Sequence
<220> FEATURE:
<223> OTHER INFORMATION: oligonucleotide primers

<400> SEQUENCE: 8
cgcggatccg ttaacatcta ctggctccat ttcttgctc                                  39

<210> SEQ ID NO 9
<211> LENGTH: 25
<212> TYPE: DNA
<213> ORGANISM: Artificial Sequence
<220> FEATURE:
<223> OTHER INFORMATION: oligonucleotide primers

<400> SEQUENCE: 9
gtgcaacacc atggcaggcc ccaga                                                 25

<210> SEQ ID NO 10
<211> LENGTH: 39
<212> TYPE: DNA
<213> ORGANISM: Artificial Sequence
<220> FEATURE:
<223> OTHER INFORMATION: oligonucleotide primers

<400> SEQUENCE: 10
tgcactgcag gaagatctta gacctggagg gggaggagg                                  39

<210> SEQ ID NO 11
<211> LENGTH: 17
<212> TYPE: DNA
<213> ORGANISM: Artificial Sequence
<220> FEATURE:
<223> OTHER INFORMATION: fusion junctions of the pTM-vpr1SN/SN* plasmid

<400> SEQUENCE: 11
agtagatgtt gggatcc                                                          17

<210> SEQ ID NO 12
<211> LENGTH: 5
<212> TYPE: PRT
<213> ORGANISM: Artificial Sequence
<220> FEATURE:
<223> OTHER INFORMATION: fusion junctions of the pTM-vpr1SN/SN* plasmid

<400> SEQUENCE: 12

Ser Arg Cys Trp Asp
  1               5

<210> SEQ ID NO 13
<211> LENGTH: 29
<212> TYPE: DNA
<213> ORGANISM: Artificial Sequence
<220> FEATURE:
<223> OTHER INFORMATION: fusion junctions of the pTM-vpx2SN/SN* plasmid

<400> SEQUENCE: 13
```

```
ctaagatcgg ggagctcact agtggatcc                                            29
```

<210> SEQ ID NO 14
<211> LENGTH: 9
<212> TYPE: PRT
<213> ORGANISM: Artificial Sequence
<220> FEATURE:
<223> OTHER INFORMATION: fusion junctions of the pTM-vpx2SN/SN* plasmid

<400> SEQUENCE: 14

```
Leu Arg Ser Gly Ser Ser Leu Val Asp
 1               5
```

<210> SEQ ID NO 15
<211> LENGTH: 21
<212> TYPE: DNA
<213> ORGANISM: Artificial Sequence
<220> FEATURE:
<223> OTHER INFORMATION: fusion junctions of the pLR2P-vpr1CAT  plasmid

<400> SEQUENCE: 15

```
agtagatgtt gggatctaat g                                                    21
```

<210> SEQ ID NO 16
<211> LENGTH: 7
<212> TYPE: PRT
<213> ORGANISM: Artificial Sequence
<220> FEATURE:
<223> OTHER INFORMATION: fusion junctions of the pLR2P-vpr1CAT plasmid

<400> SEQUENCE: 16

```
Ser Arg Cys Trp Asp Leu Met
 1               5
```

<210> SEQ ID NO 17
<211> LENGTH: 33
<212> TYPE: DNA
<213> ORGANISM: Artificial Sequence
<220> FEATURE:
<223> OTHER INFORMATION: fusion junctions of the pLR2P-vpx2CAT plasmid

<400> SEQUENCE: 17

```
ctaagatcgg ggagctcact agtggatcta atg                                       33
```

<210> SEQ ID NO 18
<211> LENGTH: 11
<212> TYPE: PRT
<213> ORGANISM: Artificial Sequence
<220> FEATURE:
<223> OTHER INFORMATION: fusion junctions of the pLR2P-vpx2CAT plasmid

<400> SEQUENCE: 18

```
Leu Arg Ser Gly Ser Ser Leu Val Asp Leu Met
 1               5                  10
```

FUSION PROTEIN DELIVERY SYSTEM AND USES THEREOF

RELATED APPLICATION

This patent application is a continuation-in-part of patent application Ser. No. 09/089,900 filed Jun. 3, 1998 which is incorporated herein by reference.

BACKGROUND OF THE INVENTION

1. Field of the Invention

The present invention relates generally to the fields of molecular virology and protein chemistry. More specifically, the present invention relates to the use of Human and Simian Immunodeficiency Virus (HIV/SIV) Gag proteins, or amino acid residues that mediate their packaging, as vehicles for delivery of proteins/peptides to virions or virus-like particles and uses thereof.

2. Description of the Related Art

Unlike simple retroviruses, human and simian immunodeficiency viruses (HIV/SIV) encode proteins in addition to Gag, Pol, and Env that are packaged into virus particles. These include the Vpr protein, present in all primate lentiviruses, and the Vpx protein, which is unique to the HIV-2/SIV$_{SM}$/SIV$_{MAC}$ group of viruses. Since Vpr and Vpx are present in infectious virions, they have long been thought to play important roles early in the virus life cycle. Indeed, recent studies of HIV-1 have shown that Vpr has nucleophilic properties and that it facilitates, together with the matrix protein, nuclear transport of the viral preintegration complex in nondividing cells, such as the macrophage. Similarly, Vpx-deficient HIV-2 has been shown in exhibit delayed replication kinetics and to require 2–3 orders of magnitude more virus to produce and maintain a productive infection in peripheral blood mononuclear cells. Thus, both accessory proteins appear to be important for efficient replication and spread of HIV/SIV in primary target cells.

Incorporation of foreign proteins into retrovirus particles has previously been reported by fusion with gag. The yeast retrotransposon Ty1 was tested as a retrovirus assembly model to interfere with viral replication. (G. Natsoulis et al. *Nature* 1991, 352:632–5). More recently, the expression of a murine retrovirus capsid-staphylococcal nuclease fusion protein was found to inhibit murine leukemia virus replication in tissue culture cells. The expression of Gag-staphylococcal nuclease reduces viral titer and diminishes viral infectivity to promote an anti-HIV strategy. (G. Schumann et al. *J. Virol.* 1996, 70:4329–37).

Lentiviral vectors, specifically those based on HIV-1, HIV-2 and SIV, have utility in gene therapy, due to their attractive property of stable integration into nondividing cell types (Naldini, L. et al. *Science* 1996, 272:263–267; Stewart, S. A. et al. *J. Virol.* 1997, 71:5579–5592; Zhang, J. et al. *Science* 1993, 259:234–238). The utility of lentiviral-based vector use for human therapy requires the development of a safe lentivral-based vector. HIV virion associated accessory proteins (Vpr and Vpx) have been shown to be useful as vehicles to deliver protein of both viral and non-viral origin into HIV particles (Liu, H. et al. *J. Virol.* 1995, 69:7630–7638; Liu, H. et al. *J. Virol.* 1997, 71:7704–7710; Wu, X. et al. *J. Virol.* 1994, 68:6161–6169; Wu, X. et al. *EMBO Journal* 1997, 16:5113–5122; Wu, X. et al. *J. Virol.* 1996, 70:3378–3384). We recently demonstrated that trans- RT and IN mimic cis- RT and IN (derived from Gag-Pol). The trans- RT and IN proteins effectively rescue the infectivity and replication of virions derived from RT-IN minus provirus through the complete life cycle (Liu, H. et al. *J. Virol.* 1997, 71:7704–7710; Wu, X. et al. *J. Virol.* 1994, 68:6161–6169). Moreover, these findings demonstrate that truncated Gag-Pol precursor polyprotein (Gag-Pro) support the formation of infectious particles when the functions of RT and IN are provided in trans. This finding demonstrated for the first time for a lentivirus that the full length Gag-Pol precursor is not required for the formation of infectious particles. Our data also show that trans Vpr-RT-IN, or Vpr-RT together with Vpr-IN are fully functional and support virus infectivity, integration of the proviral DNA, and replication (through one cycle) of RT defective, IN defective and RT-IN defective viruses (Liu, H. et al. *J. Virol.* 1997, 71:7704–7710; Wu, X et al. *J. Virol.* 1994, 68:6161–6169). It should also be noted that our data demonstrate that enzymatically active RT does not require Vpr for incorporation into virions (FIGS. 19A and B). RT can be incorporated into HIV-1 virions when expressed in trans even without its expression as a fusion partner of Vpr. These data demonstrate that the functions of these critical enzymes can be provided in trans, independent of their normal mechanism for expression and virion incorporation as components of the Gag-Pol precursor protein.

The prior art is deficient in the lack of effective means of delivering or targeting foreign, e.g., toxic proteins to virions. The present invention fulfills this longstanding need and desire in the art.

SUMMARY OF THE INVENTION

The present invention shows that Gag and/or Gag variants can be used as vehicles to target proteins of viral and non-viral origin into HIV/SIV virions. Gage gene fusions were constructed with bacterial staphylococcal nuclease (SN), chloramphenicol acetyl transferase (CAT) genes, green fluorescence protein (GFP), reverse transcriptase (RT), integrase (IN) and combinations thereof. Fusion proteins containing a Gag moiety should be packaged into HIV particles by expression in trans, to the native viral genome.

Gag fusion proteins were constructed and their abilities to package into HIV particles were demonstrated. The present invention shows that Gag fusion proteins were expressed in mammalian cells and were incorporated into HIV particles even in the presence of wild-type Gag proteins. The present invention further shows that virion incorporated Gag fusions remain infective in contrast to the prior art (G. Schuman et al. *J. Virol.* 1996, 70:4379–37). Thus, targeting heterologous Gag fusion proteins, including deleterious enzymes, to virions represents a new avenue toward anti-HIV drug discovery and gene therapy.

The invention shows that Gag proteins and variants thereof are operative as vehicles to deliver fully functional RT and IN in trans into lentiviral and retroviral particles, independently of their normal expression as components of the Gag-Pol precursor protein. Therefore this invention generates a novel packaging component (Gag-Pro), and a novel trans-enzymatic element that provides enzyme function for retroviral-based vectors. According to the present invention, the generation of potentially infectious/replicating retroviral forms (LTR-gag-pol-LTR) is decreased, since according to the present invention this requires recombination of at least three separate RNAs derived from the different plasmids: vector plasmid, packaging plasmid, a trans-enzyme expression plasmid and envelope plasmid, and as such is unlikely to occur. Virion Gag proteins are utilized in the present invention as vehicles to deliver the RT and IN proteins into lentiviral vectors, independently of Gag-Pol. As such, a "trans-lentiviral" or "transretroviral" vector is utilized for gene delivery, and gene therapy.

In one embodiment of the present invention, there is provided a composition of matter, comprising: DNA encoding a viral Gag protein fused to DNA encoding a virus inhibitory protein.

In another embodiment of the present invention, there is provided a composition of matter, comprising: DNA encoding a viral Gag protein truncate fused to DNA encoding a virus inhibitory protein.

In yet another embodiment of the present invention, there is provided a method of delivering a virus inhibitory molecule to a target in an animal, comprising the step of administering to said animal an effective amount of the composition of the present invention.

In still yet another embodiment of the present invention, there is provided a pharmaceutical composition, comprising a composition of the present invention and a pharmaceutically acceptable carrier.

Other and further aspects, features, and advantages of the present invention will be apparent from the following description of the presently preferred embodiments of the invention given for the purpose of disclosure.

BRIEF DESCRIPTION OF THE DRAWINGS

The file of this patent contains drawings executed in color. Copies of this patent with color drawings will be provided by the Patent and Trademark Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not be considered limiting in their scope.

FIG. 2 shows the expression of Vpr1- and VPX2- SN and SN* fusion proteins in mammalian cells.

FIG. 3 shows the incorporation of Vpr-1- and Vpx2- SN and SN* fusion proteins into virus-like particles (VLP).

FIG. 4 shows that virus-specific signals mediate incorporation of Vpr- and Vpx- Sn into VLPs.

FIG. 5 shows a competition analysis of Vpr1SN and Vpx2SN for incorporation into VLPs.

FIG. 6 shows the nuclease activity of VLP-associated Vpr1SN and Vpx2SN proteins. Virus-like particles were concentrated from culture supernatants of T7 expressing HeLa cells cotransfected with pTM-gag1/pTM-vpr1SN, pTM-gag1/pTM-vpr1SN*, pTM-gag2/pTM-vpx2SN and pTM-gag2/pTM-vpx2SN* by ultracentrifugation (125,000 ×g, 2 hrs.) through 20% cushions of sucrose. Pellets containing Vpr1- SN and SN* (B) and Vpx2-SN and SN* (C) were resuspended in PBS. Tenfold dilutions were made in nuclease reaction cocktail buffer (100 mM Tris-HCl pH 8.8, 10 mM $CaCl_2$, 0.1% NP40) and boiled for 1 minute. 5 ul of each dilution was added to 14 ul of reaction cocktail buffer containing 500 ng of lambda phage DNA (HindIII fragments) and incubated at 37° C. for 2 hours. Reaction products were electrophoresed on 0.8% agarose gels and DNA was visualized by ethidium bromide staining. Standards (A) were prepared by dilution of purified staphylococcal nuclease (provided by A. Mildvan) into cocktail buffer and assayed.

FIG. 7 shows the incorporation of Vpx2SN into HIV-2 by trans complementation.

FIG. 8 shows the incorporation of Vpr1SN into HIV-1 virions by trans complementation. Culture supernatant virus from HLtat cells transfected with pNL4–3 (HIV-1) and pNL4–3R (HIV-1 vpr mutant) or cotranfected with pNL4–3/pLR2P-vpr1SN and pNL4–3R/pLR2P-vpr1SN was prepared for immunoblot analysis as described above. Blots were probed with anti-SN (FIG. 8A), anti-Vpr1 (FIG. 8B) and anti-Gag (FIG. 8C) antibodies.

FIG. 9 shows the inhibition of Vpr1/Vpx2-SN processing by an HIV protease inhibitor. HIV-1 (pSG3) and HIV-2 (pSXB1) proviral DNAs were cotransfected separately into replica cultures of HLtat cells with pLR2P-vpr1SN and pLR2P-vpx2SN, respectively. One culture of each transfection contained medium supplemented with 1 uM of the HIV protease inhibitor L-699–502. Virions were concentrated from culture supernatants by ultracentrifugation through cushions of 20% sucrose and examined by immunoblot analysis using anti-Gag (FIG. 9A) and anti-SN (FIG. 9B) antibodies.

FIG. 10 shows the incorporation of enzymatically active Vpr1- and Vpx2- CAT fusion proteins into HIV virions.

FIG. 11 shows virion association of enzymatically active CAT and SN fusion proteins.

FIG. 12 shows the HIV-1 genome, the construction of pΔ8.2, pCMV-VSV-G, pHR-CMV-β-gal, pCR-gag-pro, pLR2P-vpr-RT-IN, pCMV-VSV-G and pHR-CMV-β-gal plasmids. FIG. 12A shows an illustration of the HIV-1 genome. FIG. 12B shows the lentivirus vector plasmids expression system. FIG. 12C shows the illustration of a trans-lentiviral vector expression system, where RT and IN are contiguous as Vpr fusion partners.

FIG. 21 shows component constructs of a trans-retroviral vector according to the present invention. FIG. 21A shows a pCMV, Gag-Pro packaging plasmid. FIG. 21B shows a pCMV, GagNC-RT-IN trans-enzyme expression plasmid. FIG. 21C shows a vector plasmid. FIG. 21D shows an envelope plasmid construct operative in the present invention.

FIG. 22 shows component constructs of a retroviral vector according to the present invention. FIG. 22A shows a pCMV, Gag-Pro-RT-IN retroviral packaging plasmid. FIGS. 22B and C are the vector plasmid and envelope plasmids of FIGS. 21C and D, respectively.

FIG. 23 shows component constructs of a lentiviral vector according to the present invention. FIG. 23A shows a pTRE, Gag-Pro-RT-IN packaging plasmid. FIG. 23B shows a pHR-CTS, CMV, GFP, WPRE lentiviral vector plasmid. FIG. 23C is the envelope plasmid at FIG. 21D.

FIGS. 24(A)–(C) show representative trans-lentiviral trans-enzyme plasmids according to the present invention indicating Pro cleavage sites and zinc finger locations.

DETAILED DESCRIPTION OF THE INVENTION

Figure 1A:
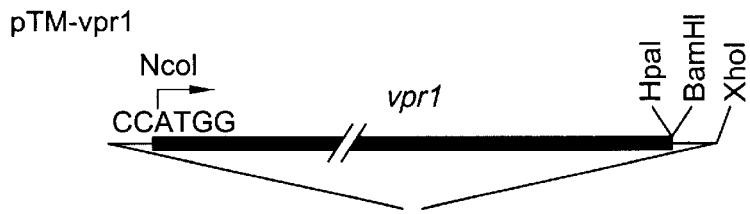
FIG. 1A shows the illustration of the pTM-vpr1 expression plasmid. The HIV-$1_{-62\ u2}$ vpr coding region was amplified by PCR and ligated into pTM1 at the NcoI and BamHI restriction sites.
Figure 1B:
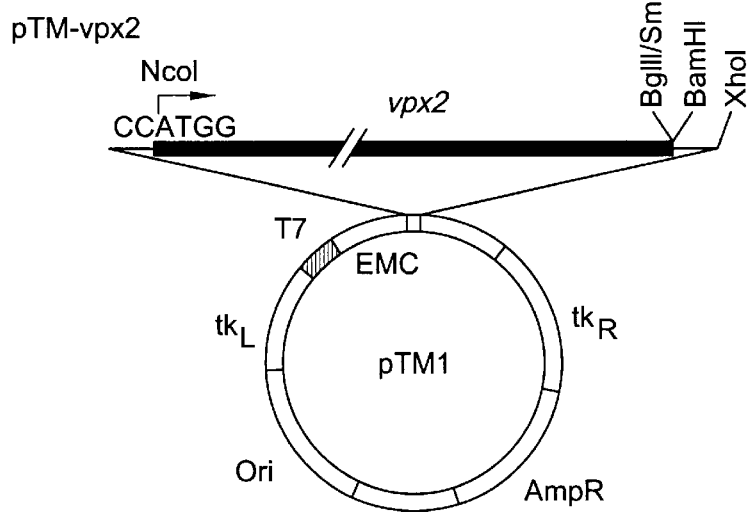
FIG. 1B shows the illustration of the pTM-vpx2 expression plasmid. The HIV-$2s_T$ vpx coding region was amplified by PCR and ligated into pTM1 at the NcoI and BglI/SmaI sites.
Figure 1C:
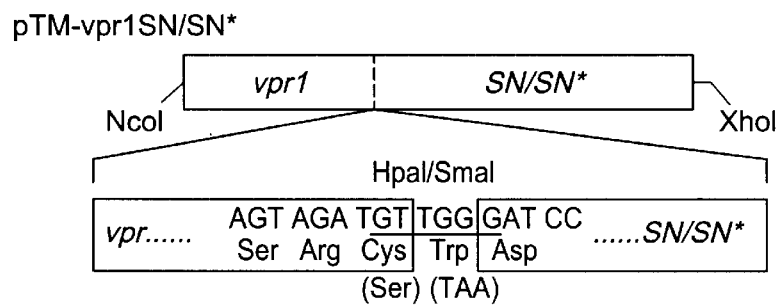
FIG. 1C shows the illustration of the fusion junctions of the pTM-v1pr1SN/SN* expression plasmids (SEQ ID NOS: 11 and 12). SmaI/XhoI DNA fragments containing Sn and SN* were ligated into HpaI/XhoI cut pTM-vpr1. Blunt-end ligation at HpaI and SmaI sites changes the vpr translational stop codon (TAA) to Trp and substituted the C terminal Ser with a Cys residue. FIG. ID shows the illustration of the fusion junctions of the pTM-vpx2SN/SN* expression plasmids (SEQ ID NOS: 13 and 14). BahHI/XhoI DNA fragments containing SN and SN* were ligated into BahHI/XhoI cut pTM-vpx2. In the construction of these plasmids, the Vpx C terminal Arg codon was changed to a Val codon and a Ser residue was introduced in place of the Vpx translational stop codon (TAA). Fusion of vpx and SNGSN* at the BamHI sites left a short amino acid sequence of the pTM1 polylinker (double underlined) between the two coding regions.

As used herein, the term "fusion protein" refers to either the entire native protein amino acid sequence of Vpx (of any HIV-2 and SIV) or Vpr (of any HIV-1 and SIV) or retroviral Gag or any subfraction of their sequences that have been joined through recombinant DNA technology and are capable of association with either native HIV/SIV virions or a retrovirus-like particle.

As used herein, the term "virion" refers to HIV-1, HIV-2 and SIV virus particles.

As used herein, the term "retrovirus-like particle" refers to any composition of HIV-1, HIV-2, SIV or retrovirus proteins other than which exists naturally in naturally infected hosts that are capable of assembly and release from either natural or immortalized cells that express these proteins.

As used herein, the term "variant" refers to a polypeptide or nucleotide sequence having at least 30% sequence identity with the native sequence including fragments thereof as calculated by Fast DB as per "Current Methods in Sequence Comparison and Analysis," Macromolecule Sequencing and Synthesis, Selected Methods and Applications, pp. 127–149.

As used herein, the term "transfect" refers to the introduction of nucleic acids (either DNA or RNA) into eukaryotic or prokaryotic cells or organisms.

As used herein, the term "gene transduction element" refers to the minimal required genetic information to transduce a cell with a gene.

As used herein, the term "virus-inhibitory protein" refers to any sequence of amino acids that have been fused with Vpx or Vpr or Gag sequences that may alter in any way the ability of a retrovirus to multiply and spread in either individual cells (prokaryotic and eukaryotic) or in higher organisms. Such inhibitory molecules may include: HIV/SIV proteins or sequences, including those that may possess enzymatic activity (examples may include the HIV/SIV protease, integrase, reverse transcriptase, Vif and Nef proteins) HIV/SIV proteins or proteins/peptide sequences that have been modified by genetic engineering technologies in order to alter in any way their normal function or enzymatic activity and/or specificity (examples may include mutations of the HIV/SIV protease, integrase, reverse transcriptase, Vif and Nef proteins), or any other non-viral protein that, when expressed as a fusion protein with Vpr or Vpx or Gag, alter virus multiplication and spread in vitro or in vivo.

In the present invention, the HIV Vpr and Vpx proteins were packaged into virions through virus type-specific interactions with the Gag polyprotein precursor. HIV-1 Vpr (Vpr1) and HIV-2 Vpx (Vpx2) are utilized to target foreign proteins to the HIV particle as their open reading frames were fused in-frame with genes encoding the bacterial staphylococcal nuclease (SN), an enzymatically inactive mutant of SN (SN*), and the chloramphenicol acetyl transferase (CAT). Transient expression in a T7-based vaccinia virus system demonstrated the snythesis of appropriately sized Vpr1SN/SN* and Vpx2SN/SN* fusion proteins which, when co-expressed with their cognate p55$^{Gag}$ protein, were efficiently incorporated into virus-like particles (VLPs). Packaging of the fusion proteins was dependent on virus type-specific determinants, as previously seen with wild-type Vpr and Vpx proteins. Particle associated Vpr1S N and Vpx2SN fusion proteins were enzymatically active as determined by in vitro digestion of lambda phage DNA. To demonstrate that functional Vpr1 and Vpx2 fusion proteins were targeted to HIV particles, the gene-fusions were cloned into an HIV-2 LTR/RRE regulated expression vector and co-transfected with wild-type HIV-1 and HIV-2 proviruses. Western blot analysis of sucrose gradient purified virions revealed that both Vpr1 and Vpx2 fusion proteins were efficiently packaged regardless of whether SN, SN* or CAT were used a C terminal fusion partners. Moreover, the fusion proteins remained enzymatically active and were packaged in the presence of wild-type Vpr and Vpx proteins. Interestingly, virions also contained smaller sized proteins that reacted with antibodies specific for the accessory proteins as well as SN and CAT fusion partners. Since similar proteins were absent from Gag-derived VLPs as well as in virions propagated in the presence of an HIV protease inhibitor, they must represent cleavage products produced by the viral protease. Taken together, these results demonstrate the Vpr and Vpx can be used to target functional proteins, including potentially deleterious enzymes, to the HIV/SIV particle. These properties are useful for the development of novel antiviral strategies.

In the present invention, a gene cassette is coupled to a retrovirus Gag variant within a trans-enzyme plasmid to induce fusion protein expression of the gene. Through selection of the gene and modification of the Gag nucleotide sequence, the vectors of the present invention are operative as antiviral therapeutics and/or gene delivery vectors when transfected into host cells in conjunction with genes or variants thereof coding packaging, vector and envelope polypeptides. While the present invention is detailed herein when plasmids each encoding different vector functions, it is appreciated that such functions are readily combined into a lesser number of plasmids including one, two and three plasmids which are cotransfected into a host cell. Preferably, a multiple plasmid gene delivery system is utilized according to the present invention.

A Gag based trans-lentiviral vector was produced by transfecting 293T cells with the pCMV-gag-pro (packaging plasmid), a different trans-enzyme plasmid based on Gag, the pPCMV-eGFP (transfer vector), and the pMD-G (env plasmid). The Gag based trans-lentiviral vector of the present invention demonstrates that the Gag precursor protein is able to deliver function fusion proteins to a host cell. The fusion proteins illustratively including RT, IN, RT-IN, GFP, CAT, CFTR and the like. As a control, trans-lentiviral vector based Vpr was produced by transfecting 293T cells with the pCMV-gag-pro (packaging plasmid), the pLR2P-Vpr-RTIN (trans-enzyme plasmid), the pPCMV-eGFP (transfer vector), and the pMD-G (env plasmid) (Wu, X. et al. *EMBO Journal* 1997, 16:5113–5122 (1997). Using fluorescence microscopy to monitor GFP expression, the infectivity of the trans-lentiviral vector particles was monitored on monolayer cultures of HeLa cells. As shown in Table 1, the titer of the trans-lentiviral vector based on Gag ranged from 0.4 to $4\times10^5$/ml, while that of the trans-lentiviral vector based on Vpr ranged from 5 to $9\times10^5$/ml. The Gag precursor protein according to the present invention is capable of delivering functional proteins into the vector particles.

retrovirus, like the lentivirus, also Cis acting RT-IN derived from the native Gag-Pol structure (GAG-PR-RT-IN) is replaced by trans-RT-IN derived from Gag-RT and Gag-IN or a triple fusion of Gag-RT-IN in a retrovirus such as a lentivirus. Thus, a trans-retroviral vector based Gag was produced by transfecting 293T cells with the 5 ug of packaging construct (pCMV-ATG/gag-pro), 2 ug of the trans-enzyme plasmid (pCMV-ATG/gag-RT-IN), 5 ug of the transfer vector (pRTCMV-eGFP-WPRE) and the pMD-G (env plasmid). As a control, the retrovirus vector was produced by transfecting 293T cells with the pCMV-ATG/gag-pol (packaging plasmid), 5 ug of the transfer vector (pRTCMV-eGFP-WPRE) and the pMD-G (env plasmid). Using fluorescence microscopy to monitor GFP expression, the infectivity of the trans-lentiviral vector particles was monitored on monolayer cultures of HeLa cells. As shown in Table 2, the titer of the trans-retrovirus vector ranged from 0.6 to $1.8\times10^7$/ml. Retrovirus vector titers ranged from 0.8 to $2.5\times10^7$/ml. This result demonstrates that the simple rgag precursor protein of a retrovirus also can deliver the functional proteins into a vector particle in trans. Thus, according to the present invention gene delivery to a host cell occurs with a Gag precursor gene a fusion partner to a protein of interest, thereby making a variety of retroviruses operative as gene delivery vector systems.

TABLE 2

Titers of the Trans-Retroviral and Retroviral Vectors

| Trans-enzyme Plasmid | Packaging Plasmid | Vector Plasmid | Envelope Plasmid | Viral Titer |
|---|---|---|---|---|
| NA* | pCMV,Gag-Pro-RT-IN | pRT-CMV,GFP,WPRE | pMD-G | $7.18 \times 10^6$ |
| NT** | pCMV,Gag-Pro | pRT-CMV,GFP,WPRE | pMD-G | $6 \times 10^3$ |
| pCMV,GagNC-RT-IN | NT** | pRT-CMV,GFP,WPRE | pMD-G | 0 |
| pCMV,GagNC-RT-IN | pCMV,Gag-Pro | pRT-CMV,GFP,WPRE | pMD-G | $1.78 \times 10^7$ |

*NA not applicable
**NT Not transfected

Reproducibly, the titer of the trans-lentiviral vector based Gag was approximately 2–5 fold less than that of the trans-lentiviral vector based Vpr for RT-IN.

TABLE 1

Titers of Trans-Lentiviral GagRTIN Vectors

| Constructs | Trans-Lentiviral Delivery Vectors | Viral Titer | Control Viral Titer* |
|---|---|---|---|
| A | pTRE, GagNC-RT-IN,RRE-1 | $3.5 \times 10^4$ | $5 \times 10^5$ |
| B | pPLR2P-GagNC(IZF)-RT-IN,RRE-2** | $3.75 \times 10^5$ | $6.5 \times 10^5$ |
| C | pLR2P-CA-RT-IN,RRE-2*** | $1.25 \times 10^5$ | $8.75 \times 10^5$ |
| D | pLR2P-GagNC-RT-IN,RRE-2 | $2.5 \times 10^5$ | $5 \times 10^5$ |
| E | pLR2P-GagNC(ΔPC)-RT-IN,RRE-2**** | $1.25 \times 10^5$ | $5 \times 10^5$ |

*pLR2P-Vpr-RT-IN plasmid was used as positive control.
**The 3' Zinc Finger domain was deleted in the NC domain of this construct.
***The whole NC domain was deleted in this construct.
****Only the Pro-RT protease cleavage site exists between the Gag and RT domains of this construct The ability of trans-RT-IN to support virus infectivity of the lentivirus parties (virions derived from RT-IN minus proviral DNA of HIV-1) or a lentivirus-based vector, indicates that trans-RT-IN fusion protein is readily substituted for cis acting RT-IN. To determine whether the trans-RT-IN (derived from the Gag-RT-IN fusion protein) of a simple Methods
(1) Vector particles were generated by DNA transfection into 293T cells.
(2) Vector titers were determined by infecting HeLa cells. The results are expressed as infectious particles/ml of culture supernatant collected from transfected 293T cells.

Gag fusions are operative here from retroviruses and lentiviruses including Moloney Leukemia Virus (MLV), Abelson murine leukemia virus, AKR (endogenous) murine leukemia virus, Avian carcinoma, Mill Hill virus 2, Avian leukosis virus—RSA, Avian myeloblastosis virus, Avian myelocytomatosis virus 29, Bovine syncytial virus, Caprine arthritis encephalitis virus, Chick syncytial virus, Equine infectious anemia virus, Feline leukemia virus, Feline syncytial virus, Finkel-Biskis-Jinkins murine sarcoma virus, Friend murine leukemia virus, Fujinami sarcoma virus, Gardner-Arnstein feline sarcoma virus, Gibbon ape leukemia virus, Guinea pig type C oncovirus, Hardy-Auckerman feline sarcoma virus, Harvey murine sarcoma virus, Human foamy virus, Human spumavirus, Human T-lymphotropic virus 1, Human T-lymphotropic virus 2, Jaagsiekte virus, Kirsten murine sarcoma virus, Langur virus, Mason-Pfizer monkey vikrus, Moloney murine sarcoma virus, Mouse mammary tumor virus, Ovine pulmonary adenocarcinoma virus, Porcine type C oncovirus, Reticuloendotheliosis virus, Rous sarcoma virus, Simian foamy virus, Simian sarcoma virus, Simian T-lymphotropic virus, Simian type D virus 1, Snyder-Theilen feline sarcoma virus, Squirrel monkey retrovirus, Trager duck spleen necrosis virus, UR2 sarcoma virus, Viper retrovirus, Visna/maedi virus, Woolly monkey sarcoma virus, and Y73 sarcoma virus human-, simian-, feline-, and bovine immunodeficiency viruses (HIV, SIV, FIV, BIV). While RT and IN fusions with Gag are operative herein, it is appreciated that a variety of therapeutic and diagnostic fusion proteins are similarly deliverable to a target cell according to the methodologies and vectors disclosed herein.

Gag-based trans-lentiviral vectors are disclosed based on non-primate lentiviruses and simple retroviruses encoding retrovirus Gag precursor proteins which have functions akin to those of primate lentiviral Vpr or Vpx proteins. Contrary to the prior art, the present invention maintains viral infectivity in non-dividing primary cells. The WPRE sequence encoded within a vector of the present invention is necessary therefor. Infectivity of the vectors of the present invention is further enhanced through the use of a gene transfer vector containing the posttranscriptional regulatory element of woodchuck hepatitis virus (WPRE). While the inclusion of a WPRE gene or gene fragment capable of regulating posttranscription increases trans-lentiviral titer alone, the inclusion of additional PPT-CTS sequences creates a cumulative enhancement in viral infectivity. WPRE has been shown to increase luciferase or GFP production in similar virus-based vectors (R. Bufferey, *J. Virol.* 73, 2886–2892 (1999). Alternatively, the central terminator sequence (CTS) and central polypurine tract (PPT) are introduced into the gene transfer vector and new viral and trans-viral vectors to independently increase titer, as detailed in U.S. Provisional Application No. 60/164,626 filed Nov. 10, 1999. PPT and CTS have been implicated in HIV-1 reverse transcription. P. Charneau et al., *J. Mol. Biol.* 241, 651–662 (1994). It is appreciated the other control sequences capable of stabilizing messenger RNA and thereby facilitating protein expression are operative in place of WPRE, PPT and CTS within the present invention.

The present invention provides for a delivery of a trans protein or gene to a viral vector through coupling to either a viral protein or gene delivery, respectively; wherein the viral protein is Vpr or Vpx or Gag and the gene encodes either Vpr or Vpx or Gag. Certain truncation variants to these trans protein or genes perform the regulatory or enzymatic functions of the full sequence protein or gene. For example, the nucleic acid sequences coding for protease, integrase, reverse transcriptase, Vif, Nef, Gag, RT, IN and CFTR can be altered by substitutions, additions, deletions or multimeric expression that provide for functionally equivalent proteins or genes. Due to the degeneracy of nucleic acid coding sequences, other sequences which encode substantially the same amino acid sequences as those of the naturally occurring proteins may be used in the practice of the present invention. These include, but are not limited to, nucleic acid sequences comprising all or portions of the nucleic acid sequences encoding the above proteins, which are altered by the substitution of different codons that encode a functionally equivalent amino acid residue within the sequence, thus producing a silent change. For example, one or more amino acid residues within a sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present invention are proteins or fragments or derivatives thereof which are differentially modified during or after translation, e.g., by glycosolation, protolytic cleavage, linkage to an antibody molecule or other cellular ligands, etc. In addition, the recombinant ligand encoding nucleic acid sequences of the present invention may be engineered so as to modify processing or expression of a ligand. For example, a signal sequence may be inserted upstream of a ligand encoding sequence to permit secretion of the ligand and thereby facilitate apoptosis.

Additionally, a ligand encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacea), etc.

The following examples are given for the purpose of illustrating various embodiments of the invention and are not meant to limit the present invention in any fashion.

EXAMPLE 1

Cells and Viruses

HeLa, HeLa-tat (HLtat), 293T and CV-1 cells were maintained in Dulbecco's Modified Eagle's Medium supplemented with 10% fetal bovine serum (FBS), 100 U penicillin and 0.1 mg/ml streptomycin. HLtat cells constitutively express the first exon of HIV-1 tat and were provided by Drs. B. Felber and G. Pavlakis. A recombinant vaccinia virus (rVT7) containing the bacteriophage T7 RNA polymerase gene was used to facilitate expression of viral genes placed under the control of a T7 promoter. Stocks of rVT7 were prepared and titrated in CV-1 cells as described in previously by Wu, et al *J. Virol.* 1992, 66:7104–7112. HIV-1$_{YU2}$, HIV-1 pNL 4-3-R⁻ and pNL 4-3, HIV-1$_{HXB2D}$, HIV-2$_{ST}$, and HIV-2$_{7312A}$ proviral clones were used for the construction of recombinant expression plasmids and the generation of transfection derived viruses.

EXAMPLE 2

Antibodies

To generate HIV-1 Vpr specific antibodies, the HIV-1$_{yu-2}$ vpr open reading frame was amplified by polymerase chain reaction (PCR) using primers (sense: 5'GCCACCTTTGTCGACTGTTAAAAAACT-3' (SEQ ID NO:1) and anti-sense 5'-GTCCTAGGCAAGCTTCCTGGATGC-3' (SEQ ID NO:2) containing SalI and HindIII sites and ligated into the prokaryotic expression vector, pGEX, generating pGEX-vpr1. This construct allowed expression of Vpr1 as a C terminal fusion protein and glutathione S-transferase (gst), thus allowing protein purification using affinity chromatography. *E. coli* (DH5a) were transformed with pGEX-vpr1 and protein expression was induced with isoprpyl (3-D thiogalactopyranoside (IPTG). Expression of the gst-Vpr1 fusion protein was confirmed by SDS-PAGE. Soluble gst- Vpr1 protein was purified and Vpr1 was released by thrombin cleavage using previously described procedures of Smith, et al. *Gene* 1988, 67:31–40. New Zealand White rabbits were immunized with 0.4 mg of purified Vpr1 protein emulsified 1:1 in Freunds complete adjuvant, boosted three times at two week intervals with 0.25 mg of Vpr1 mixed 1:1 in Freunds' incomplete adjuvant and bled eight and ten weeks after the first immunization to collect antisera. Additional antibodies used included monoclonal antibodies to HIV-1 Gag (ACT1, and HIV-2 Gag (6D2.6), polyclonal rabbit antibodies raised against the HIV-2 Vpx protein and anti-SN antiserum raised against purified bacterially expressed SN protein.

EXAMPLE 3

Construction of T7-based Expression Plasmids

A DNA fragment encompassing $^{HIV-1}$HXB2D$^{gag}$ (nucleotides 335–1837) was amplified by PCR using primers (sense: 5'-AAGGAGAGCCATGGGTGCG AGAGCG-3' (SEQ ID NO: 3) and anti-sense; 5'GGGGATCC CTT-TATTGT GACGAGGGG-3' (SEQ ID NO: 4) containing NcoI and BamHI restriction sites (underlined). The PCR product was digested with NcoI and BamHI, purified and ligated into the polylinker of the pTM1 vector, generating pTM-gag1. Similarly, a DNA fragment containing the gag coding region of HIV-2$_{ST}$ (nucleotides 547–2113) was amplified by PCR using sense and anti-sense primers 5'-ATTGTGGGCCATGGGCGCGAGAAAC-3' (SEQ ID NO: 5) and 5'-GGGGGG CCCCTACTGGTCTTTTCC-3 (SEQ ID NO: 6) respectively. The reaction product was cut with NcoI and SmaI (underlined), purified and ligated into the polylinker of pTM1, generating pTM-gag2.

For expression of Vpr1 under the control of the T7 promoter, a DNA fragment containing the HIV-1$_{YU2}$ vpr coding region (nucleotides 5107–5400) was amplified by PCR using primers (sense: 5'-GAAGATCTACCATGG AAGCCCCAGAAGA-3' (SEQ ID NO:7) and anti-sense: 5'-CGCGGATCCGTTAACATCTACTGGCTCCATTTCTT GCTC-3' (SEQ ID NO:8) containing NcoI and HpaI/BamHI sites, respectively (underlined). The reaction product was cut with NcoI and BamHI and ligated into pTM1, generating a pTM-vpr1 (FIG. 12A). In order to fuse SN and SN* in-frame with vpr1, their coding regions were excised from pGN1561.1 and pGN1709.3, respectively and through a series of subcloning steps, ligated into the SmaI/XhoI sites of pTM-vpr1, generating pTM-vpr1SN and pTM-vpr1SN*. This approach changed the translational stop codon of Vpr1 to a Trp codon and the C terminal Ser residue to a Cys. The resulting junctions between vpr1 and SN/SN* are depicted in FIG. 12C.

Figure 1D:
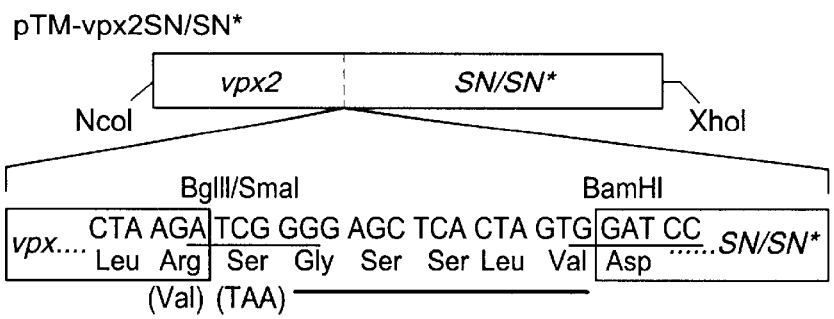
FIG. 1 shows the construction of vpr1, vpr1SN/SN*, vpx2 and vpx2SN/SN* expression plasmids.

For expression of Vpx2 under T7 control, a DNA fragment containing the HIV-2$_{ST}$ vpx coding sequence (nucleotides 5343–5691) was amplified by PCR using primers (sense: 5'GTGCAACACCATGGCAGGCCCCAGA-3' (SEQ ID NO:9) and anti-sense: 5'-TGCACTGCAGGAAGATCTTAGACCTGGAGGGGGAG GAGG-3' (SEQ ID NO: 10) containing NcoI and BglII sites, respectively (underlined). After cleave with BglII and Klenow fill-in, the PCR product was elevated with NcoI, purified and ligated into the NcoI and SmaI sites of pTM1, generating pTM-vpx2 (FIG. 12B). To construct in-frame fusion with vpx2, BamHI/XhoI, SN- and SN*-containing DNA fragments were excised from pTM-vpr1 SN and pTM-vpr1 SN* and ligated into pTM-vpx2, generating pTM-vpx2SN and pTM-vpx2SN*, respectively. This approach introduced one amino acid substitution at the C terminus of Vpx (Val to Arg), changed the translational stop codon of vpx to Ser and left five amino acids residues of the pTM1 plasmid polylinker. The resulting junctions between vpx2 and SN/SN* are depicted in FIG. 1D.

EXAMPLE 4

Construction of HIV LTR-based Vpr or Vpx Expression Plasmids

Figure 7A:
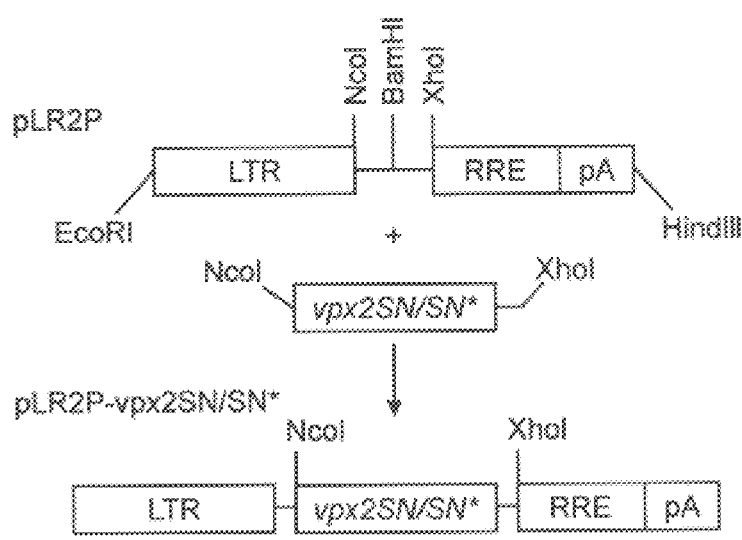
FIG. 7A shows the construction of the pLR2P-vpx2SN/SN* expression plasmids. To facilitate efficient expression of HIV genes, the HIV-2 LTR and RRE were engineered into the polylinker of pTZ19U, generating pLR2P. The organization of these elements within the pTZ19U polylinker is illustrated. NcoI/XhoI vpx2SN and vpx2SN* (vpxSN/SN*) containing DNA fragments were ligated into pLR2P, generating pLR2P-vpx2SN and pLR2P-vpx2SN* (pLR2P-vpxSN/SN*).

For efficient expression of Vpr and Vpx fusion proteins in the presence of HIV, a eukaryotic expression vector (termed pLR2P) was constructed which contains both an HIV-2 LTR (HIV-2$_{ST}$, coordinates −544 to 466) and an HIV-2 RRE (HIV-2$_{ROD}$, coordinates 7320 to 7972) element (FIG. 7A). These HIV-2 LTR and RRE elements were chosen because they respond to both HIV-1 and HIV-2 Tat and Rev proteins. The vpr1, vpr1SN, vpx2 and vpx2SN coding regions were excised from their respective pTM expression plasmids (see FIG. 1) with NcoI and XhoI restriction enzymes and ligated into pLR2P, generating pLR2P-vpr1, pLR2P-vpr1SN, pLR2P-vpx2 and pLR2P-vpx2SN, respectively (FIG. 7A). For construction and expression of vpr- and vpx-CAT gene fusions, the SN containing regions (BamHI/XhoI fragments) of pLR2P-vpr1SN and pLR2P-vpx2SN were removed and substituted with a PCR amplified BglII/XhoI DNA fragment containing CAT, generating pLR2P-vpr1CAT and pLR2P-vpx2CAT, respectively (FIG. 9A).

EXAMPLE 5

Construction of Lentiviral Plasmids Involving Gag Fusions

Figure 24A:
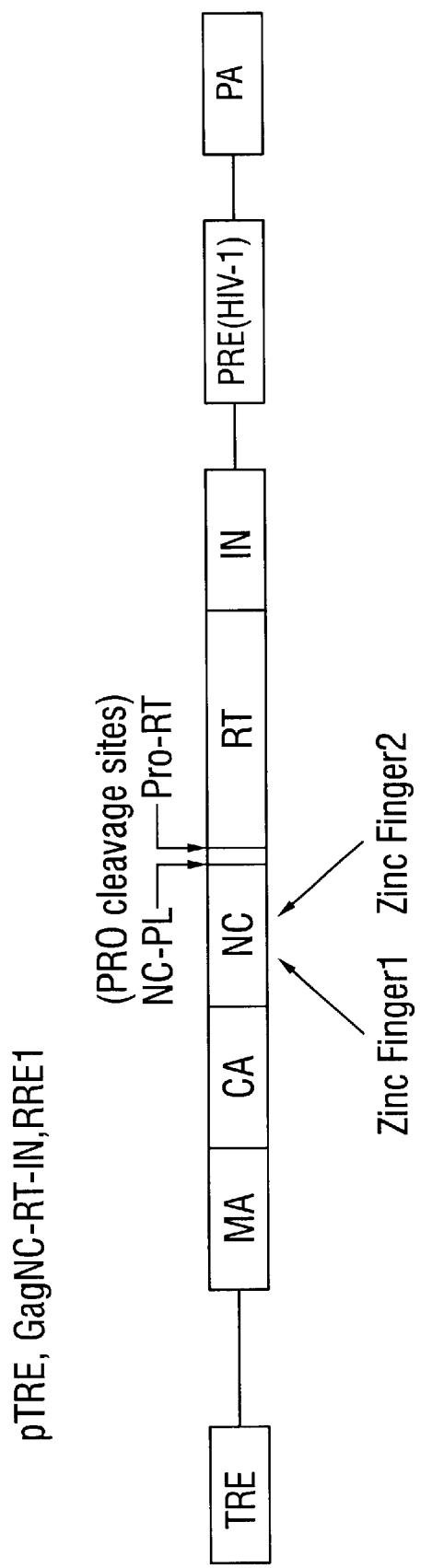

The pHRCMV-eGFP plasmid was derived by modifying pHRCMV-Lacz, which has been described (Naldini, L. et al. *Science* 1996, 272:263–267). The pHRCMV-eGFP plasmid was constructed by ligating a BamHI/XhoI DNA fragment containing eGFP (derived from pEGFP-C1; CLONTECH Laboratories, Palo Alto, Calif.) into the pHRCMV-lacz plasmid after removing lacz by digestion with BamHI and XhoI. To construct the pPCMV-eGFP, a 150 bp sequence (with coordinates 4327–4483) and containing the central PPT and central terminal site (CTS) was amplified from the SG3 molecular clone by PCR and ligated into pHRCMV-eGFP that was cut with ClaI. To construct the Tet-inducible expression plasmids, 430 bps of TRE-inducible promoter derived from pTRE; CLONTECH Laboratories, Palo Alto, Calif., was cut by XhoI 1 filled to blunt ends and Bam H 1. The CMV promoter of pcDNA3.1(+) plasmid (Invitrogen, Calif.) was replaced using SpeI 1 (filled to blunt ends) and BamHI 1, generating pTRE-neo. The 6.7 kb of the fragments containing the HIV-based packaging components derived from pCMVgag-pol was cloned into pTRe-neo using EcRI 1 and XhoI 1, generating pTRE-gag-pol which contains functional vif, tat, rev, gag and pol genes. To construct the RT-IN minus plasmid shown in FIG. 23A, the region (from 1975 to 5337) of pTREgag-pol were substituted with an RT-IN containing BclI/SalI DNA fragment (from 1975 to 5337) of pSG3S-RT was ligated into the BclI and SalI sites of the pTREgag-pol plasmid, generating pTREgag-pro. The RT-IN sequence contained translational stop codons (TAA) at the first amino acid position of the RT and IN coding regions and was under control of CMV promoter. A 39-base pair internal deletion in the 4 sequence was introduced, the internal region (1357 bp) of envelope gene was deleted from 5827 to 7184, generating pCMVgag-pol. To construct the RT-IN minus plasmid, the region (from 1975 to 5337) of pCMVgag-pol were substituted with an RT-IN containing BclI/SalI DNA fragment (from 1975 to 5337) of pSG3S-RT was ligated into the BclI and SalI sites of the pCMVgag-pol plasmid, generating pCMVgag-pro shown in Table 2. The RT-IN sequence contained translational stop codons (TAA) at the first amino acid position of the RT and IN coding regions. To construct the series of trans-enzyme plasmids shown in FIGS. 24A–C and Table 2, different fragments of HIV-1 gag genes were amplified by PCR and were cloned into pLR2PvprRTIN using Nocl 1 and Bagl 11, generating a series of gag-RTIN fusion expression plasmids. pLR2gagNC-RTIN shown in Table 1 as construct D contained the Gag gene with the p6 portion deleted. pLR2PgagNC(1ZF)-RTIN shown in FIG. 24B and construct contained the Gag gene with the second 1ZF of NC and p1–p6 fragment deleted. pLR2PgagCA-RTIN shown as FIG. 24C and in Table 1 as construct C contained the Gag gene which deleted the NC-p1–p6 fragment. pLR2PVprRTIN construction is described in regard to FIG. 12. pMD-G is constructed according to existing techniques (Wu, X. et al. *EMBO Journal* 1997, 16:5113–5122 (1997)).

EXAMPLE 6

Construction of Retroviral Plasmids Involving Gag Fusions

A RT-IN minus packaging construct is formed based on Moloney murine leukemia virus pCMV-ATG/gag-pol was cut by Sal 1 and filled with Klenow, generating pCMV-ATG/gag-pro, with the RT gene being mutated by the reading frame shift at the position of 366 aa as shown in FIG. 21A. A trans-enzyme plasmid, the 312 bp of fragment which contains protease region was deleted from the gag-pol of pCMV-ATG/gag-pol, generating pCMV-ATG/gag-RT-IN as shown in FIG. 21B. The GFP transfer vector based on Moloney murine leukemia virus, GFP-WPRE which was obtained from pPCMV-eGFP-WPRE (M. H. Finer et al. *Blood* 1994, 83:43–50) and cloned into pRTCMV using BamHI 1 and Apol 1, generating pRTCMV-eGFP-WPRE as shown in FIG. 21C.

EXAMPLE 7

Preparation of Vector Stocks and Infection

Trans-lentiviral vector stocks were produced by transfecting the 5 ug of packaging construct (pTREgag-pol), the 2 ug of VSV-G construct (pMD-G), and 5 ug of the transfer vector (pPCMV-eGFP WPRE) and 1 ug of pTet-off (CLONTECH Laboratories, Palo Alto, Calif.) and different trans-enzyme plasmids into the subconfluent 293T cell by the calcium phosphate precipitation method. Trans-retroviral vector stocks were produced by transfecting the 5 ug of packaging construct (pCMV-ATG/gag-pro), the 2 ug of VSV-G construct (pMD-G), and 5 ug of the transfer vector (pRTCMV-eGFP-WPRE) and 2 ug of the trans-enzyme plasmid (pCMV-ATG/gag-RT-IN). Approximately 1×10⁶ cells were seeded into six-well plates 24 hr prior to transfection. The vector stocks were harvested 60 hr post-transfection. Supernatants of the transfected cultures were clarified by low speed centrifugation (1000 g, 10 min), and filtered through a 0.45-um-pore-size filter, aliquoted and subsequently frozen at −80. The target cell were infected in the DMEM-1% FBS containing 10 ug/ml of DEAETestron for 4 hr at 37° C. The medium was subsequently replaced with fresh DMEM-10% FBS or preconditional medium. To determine the titer of eGFP vector, the supernatant stock of 1.0, 0.2, 0.04, and 0.008 ul were used to infect the culture of HeLa cell. 2–3 days late, positive (green) cell colonies were counted using a fluorescence microscope.

EXAMPLE 8

Transfections

Transfections of proviral clones were performed in HLtat cells using calcium phosphate DNA precipitation methods as described by the manufacturer (Strategene). T7-based (pTM1) expression constructs were transfected using Lipofectin (BioRad) into rVT7 infected HeLa cells as described previously by Wu et al. *J. Virol.* 1994, 68:6161–6169. These methods were those recommended by the manufacturer of the Lipofectin reagent.

EXAMPLE 9

Western Immunoblot Analysis

Virions and virus-like particles (VLPs) were concentrated from the supernatants of transfected or infected cells by ultracentrifugation through 20% cushions of sucrose (125, 000×g, 2 hrs., 4° C.). Pellets and infected/transfected cells were solubilized in loading buffer [62.5 mM Tris-HCl (pH 6.8) 0.2% sodium dodecyl sulfate (SDS), 5% 2-mercaptoethanol, 10% glycerol], oiled and separated on 12.5% polyacrylamide gels containing SDS. Following electrophoresis, proteins were transferred to nitrocellulose (0.2 $\mu$m; Schleicher & Schuell) by electroblotting, incubated for one hour at room temperature in blocking buffer (5% nonfat dry milk in phosphate buffered saline [PBS]) and then for two hours with the appropriate antibodies diluted in blocking buffer. Protein bound antibodies were detected with HRP-conjugated specific secondary antibodies using ECL methods according to the manufacturer's instructions (Amersham).

EXAMPLE 10

SN Nuclease Activity Assay

Cells and viral pellets were resuspended in nuclease lysis buffer (40 mM Tris-HCl, pH 6.8, 100 mM NaCl, 0.1% SDS, 1% Triton X-100) and clarified by low speed centrifugation (1000×g, 10 min.). Tenfold dilutions were made in nuclease reaction cocktail buffer (100 mM Tris-HCl, pH 8.8, 10 mM CaCl$_2$, 0.1% NP40) and boiled for 1 minute. 5 $\mu$l of each dilution was added to 14 $\mu$l of reaction cocktail buffer containing 500 ng of lambda phage DNA (HindIII fragments) and incubated at 37° C. for 2 hours. Reaction products were electrophoresed on 0.8% agarose gels and DNA was visualized by ethidium bromide staining.

EXAMPLE 11

Expression of Vpr1- and Vpx2-SN and SN* Fusion Proteins in Mammalian Cells

Figure 2A:
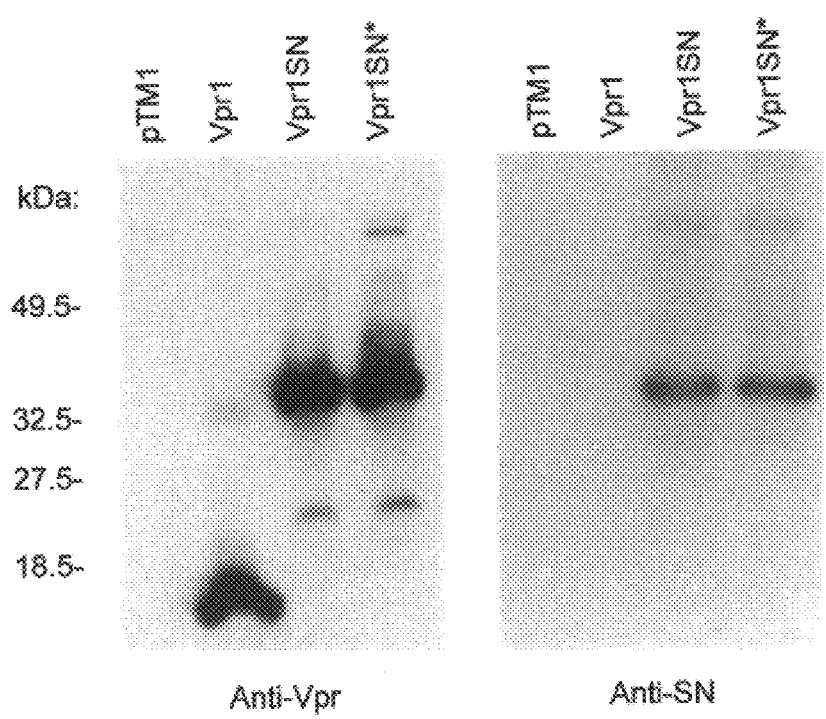
FIG. 2A shows the pTM1, pTM-vpr1, pTM-vpr1SN and pTM-vpr1SN* were transfected into HeLa cells one hour after infection with rVT7 (MOI=10). Twenty-four hours later cell lysates were prepared and examined by immunoblot analysis. Replica blots were probed with anti-Vpr1 (left) and anti-SN (right) antibodies.
Figure 2B:
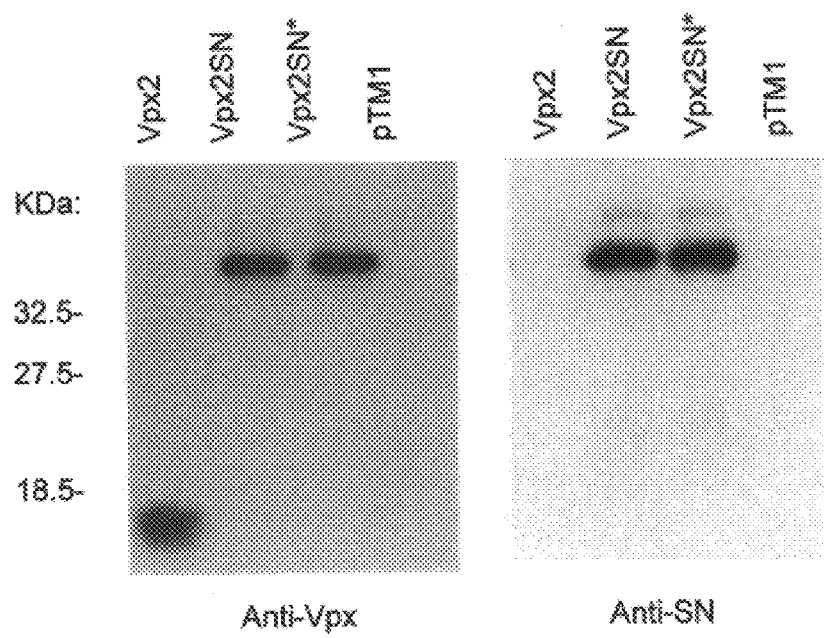
FIG. 2B shows that replica blots, prepared from rVT7 infected HeLa cells transfected with pTM1, pTM-vpx2, pTM-vpx2SN and pTM-vpx2SN*, were probed with anti-Vpx2 (left) and anti-SN (right) antibodies. Bound antibodies were detected by ECL (Amersham) methods as described by the manufacturer.

Expression of Vpr1- and Vpx2- SN/SN* fusion proteins in mammalian cells was assessed using the recombinant vaccinia virus-T7 system (rVT7). HeLa cells were grown to 75–80% confluency and transfected with the recombinant plasmids pTM-vpr, pTM-vpx, pTM-vpr1SN/SN*, and pTM-vpx2SN/SN* (FIG. 1). Twenty-four hours after transfection, cells were washed twice with PBS and lysed. Soluble proteins were separated by SDS-PAGE and subjected to immunoblot blot analysis. The results are shown in FIG. 2. Transfection of pTM-vpr1SN and pTM-vpr1SN* resulted in the expression of a 34 kDa fusion protein that was detectable using both anti-Vpr and anti-SN antibodies (A). Similarly, transfection of pTM-vpx2SN and pTM-vpx2SN* resulted in the expression of a 35 kDa fusion protein which was detected using anti-Vpx and anti-SN antibodies (B). Both fusion proteins were found to migrate slightly slower than expected, based on the combined molecular weights of Vpr1 (14.5 kDa) and SN (16 kDa) and Vpx2 (15 kDa) and SN, respectively. Transfection of pTM-vpr1 and pTM-vpx2 alone yielded appropriately sized wild-type Vpr and Vpx proteins. Anti-Vpr, anti-Vpx and anti-SN antibodies were not reactive with lysates of pTM1 transfected cells included as controls. Thus, both SN and SN* fusion proteins can be expressed in mammalian cells.

EXAMPLE 12

Figure 3A:
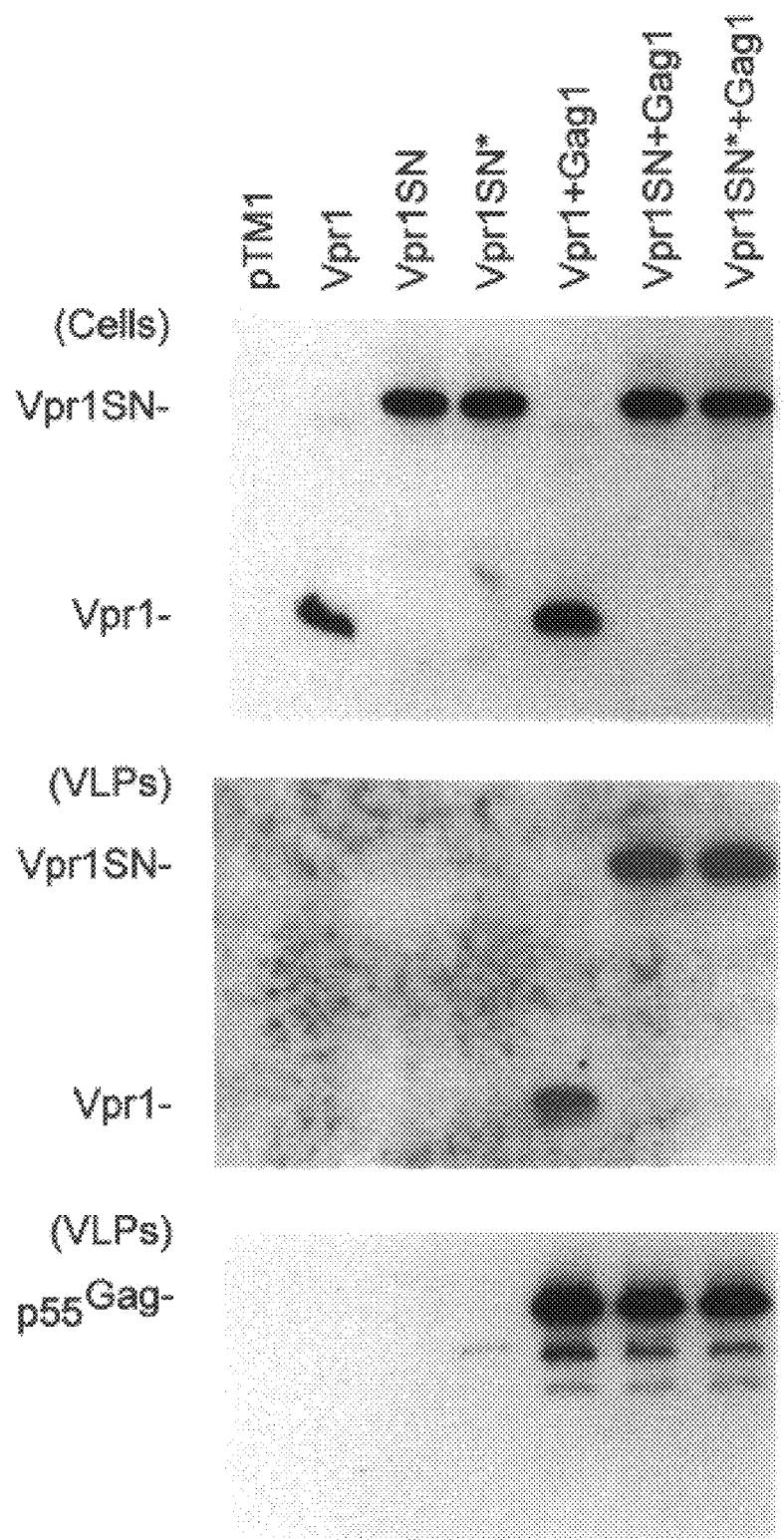
FIG. 3A transfection of T7 expressing (rVT7 infected) HeLa cells with pTM-vpr1, pTM-vpr1SN, and pTM-vpr1SN* alone and in combination with pTM-gag1. pTM1 was also transfected for control Culture supernatant were collected twenty-four hours after transfection, clarified by centrifugation (1000×g, 10 min.) and ultracentrifuged (125,000×g, 2 hrs.) over cushions of 20% sucrose. Pellets (VLPs, middle and bottom panels) and cells (top panels) were solubilized in loading buffer and examined by immunoblot analysis using anti-Vpr1 (top and middle) and anti-Gag (bottom) antibodies as probes.

Incorporation of Vpr1- and Vpr2-SN/SN* Fusion Proteins into Virus-like Particles In vaccinia and baculovirus systems, the expression of HIV Gag is sufficient for assembly and extracellular release of VLPs. Vpr1 and Vpx2 can be efficiently incorporated into Gag particles without the expression of other viral gene products. To demonstrate that the Vpr1 and Vpx2 fusion proteins could be packaged into VLPs, recombinant plasmids were coexpressed with HIV-1 and HIV-2 Gag proteins in the rVT7 system. pTM-vpr1, pTM-vpr1SN and pTM-vpr2SN* were transfected into HeLa cells alone and in combination with the HIV-1 Gag expression plasmid, pTM-gag1. Twenty-four hours after transfection, cell and VLP extracts were prepared and analyzed by immunoblot analysis (FIG. 3A). Anti-Vpr antibody detected Vpr1, Vpr1SN and Vpr1SN* in cell lysates (top panel) and in pelleted VLPs derived by coexpression with pTM-gag1 (middle panel). In the absence of HIV-1Gag expression, Vpr1 and Vpr1SN were not detected in pellets of culture supernatants (middle panel). As expected VLPs also contained p55 Gag (bottom panel). Thus, Vpr1SN/SN* fusion proteins were successfully packaged into VLPs.

Figure 3B:
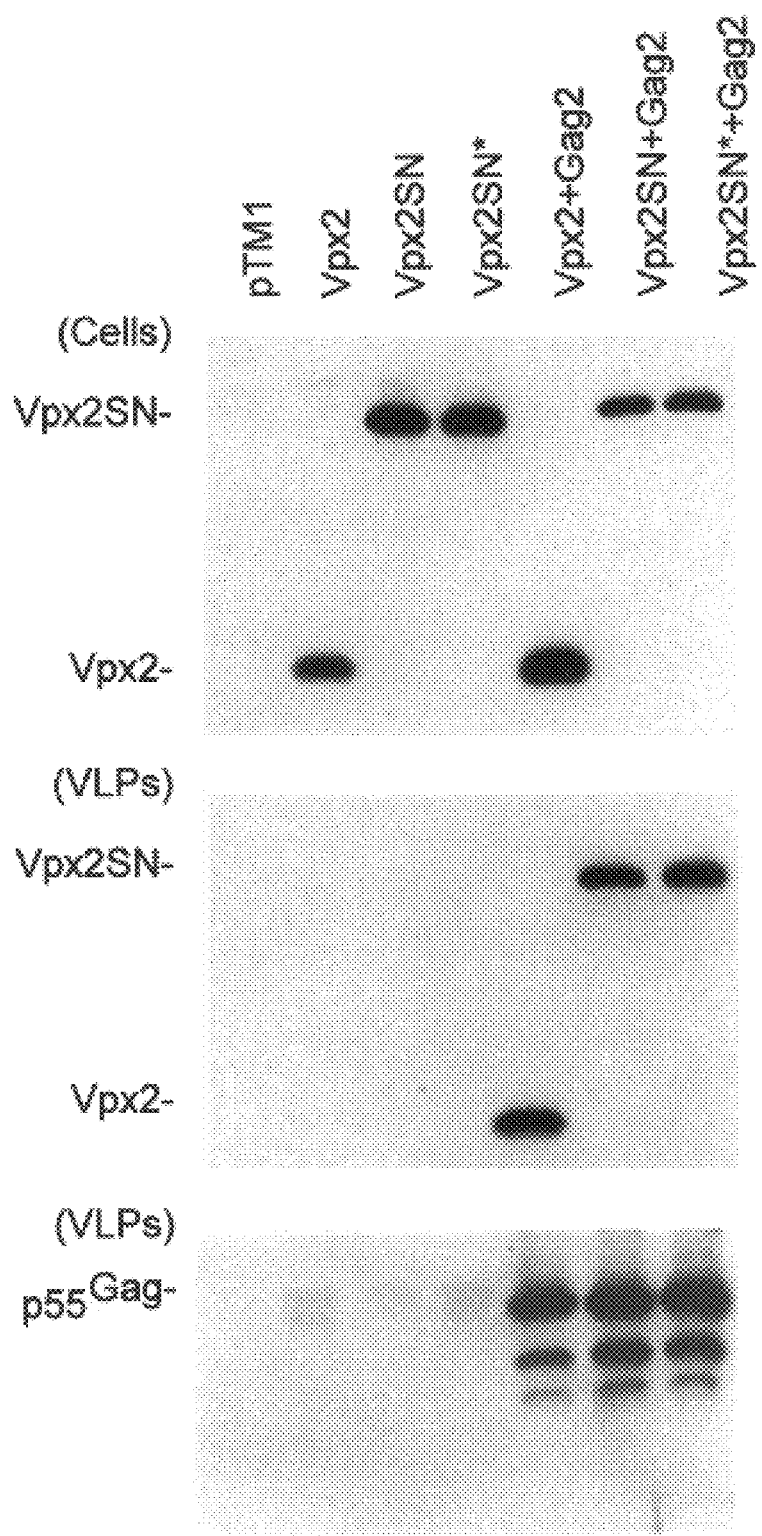
FIG. 3B transfection of T7 expressing HeLa cells pTM-vpx2, pTM-vpx2SN and pTM-vpx2SN* alone and in combination with pTM-gag2. Pellets (VLPs, middle and bottom panels) and cells (top panel) were lysed, proteins were separated by SDS-PAGE and electroblotted to nitrocellulose as described above. Replica blots were probed with anti-Vpx2 (top and middle panels) and anti-Gag (bottom panel) antibodies. Bound antibodies were detected using ECL methods.

To demonstrate that Vpx2SN was similarly capable of packaging into HIV-2 VLPs, pTM-vpx2, pTM-vpx2SN and pTM-vpx2SN* were transfected into HeLa cells alone and in combination with the HIV-2 Gag expression plasmid, pTM-gag2. Western blots were prepared with lysates of cells and VLPs concentrated from culture supernatants by ultracentrifugation (FIG. 3B). Anti-Vpx antibody detected Vpx2, Vpx2SN and Vpx2SN* in cell lysates (top panel) and in VLPs derived by coexpression with pTM-gag2 (middle panel). Anti-Gag antibody detected p55 Gag in VLP pellets (bottom panel). Comparison of the relative protein signal intensities suggested that the Vpr1- and Vpx2-SN and SN* fusion proteins were packaged into VLPs in amounts similar to wild-type Vpr1 and Vpx2 proteins. Sucrose gradient analysis of VLPs containing Vpr1SN and Vpx2SN demonstrated co-sedimentation of these fusion proteins with VLPs (data not shown).

Figures 4A, 4B:
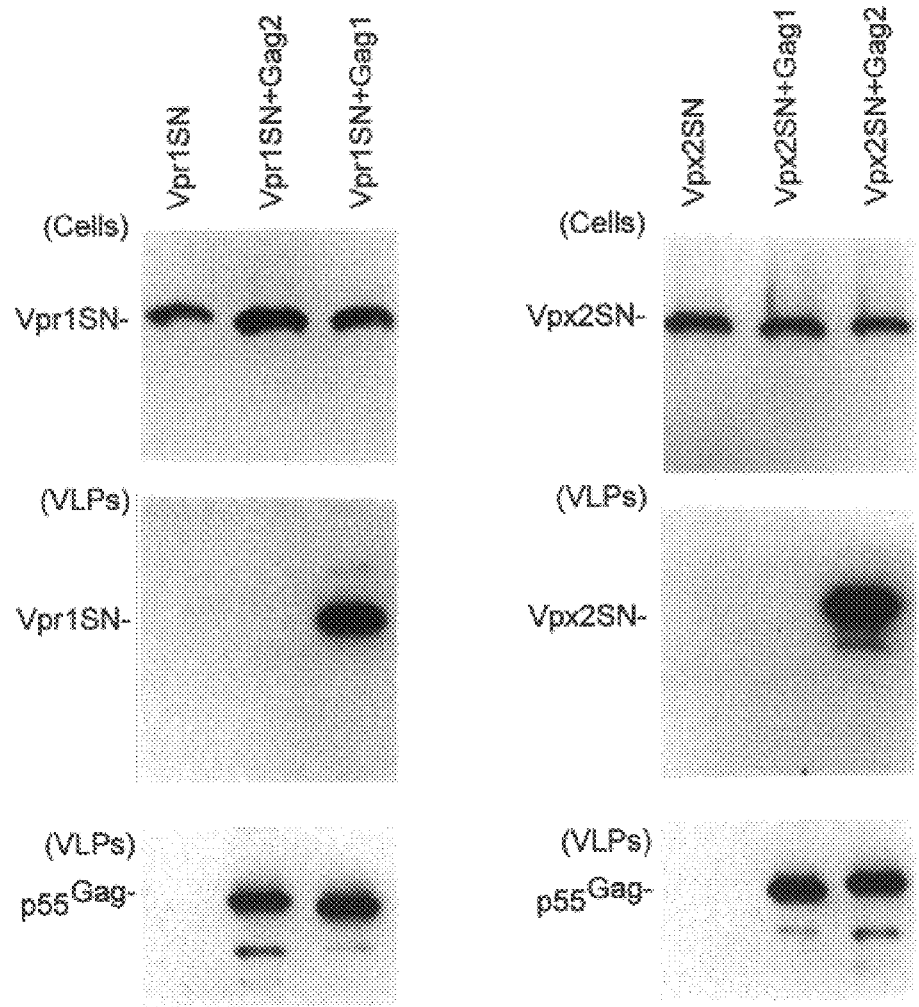
FIG. 4A shows that HIV-1 Gag mediates packaging of Vpr1SN. rVT7 infected (T7 expressing) HeLa cells were transfected with pTM-vpr1SN alone and in combination with pTM-gag2 and pTM-gag1. Pellets (VLPs, middle and bottom panels) and cells (top panel) were prepared 24 hours after transfection and examined by immunoblot analysis using anti-Vpr1 (top and middle) and anti-Gag (bottom) antibodies for probes. (B) HIV-2 Gag mediates packaging of Vpx2SN. T7 expressing HeLa cells were transfected with pTM-vpx2SN alone and in combination with pTM-gag1 and pTM-gag2. Pellets (VLPs, middle and bottom panels) and cells (top panel) were prepared 24 hours after transfection and examined by immunoblot analysis using anti-Vpx2 (top and middle) and anti-Gag (bottom) antibodies for probes.

The Gag C terminal region is required for incorporation of Vpr1 and Vpx2 into virions. However, packaging was found to be virus type-specific, that is, when expressed in trans, Vpx2 was only efficiently incorporated into HIV-2 virions and HIV-2 VLPs. Similarly, HIV-1 Vpr required interaction with the HIV-1 Gag precursor for incorporation into HIV-1 VLPs. To show that the association of Vpr1SN and Vpx2SN with VLPs was not mediated by the SN moiety, but was due to the Vpr and Vpx specific packaging signals, pTM-vpr1SN and pTM-vpx2SN were cotransfected individually with either pTM-gag1 or pTM-gag2. For control, pTM-vpr1 and pTM-vpx2 were also transfected alone. Twenty-four hours later, lysates of cells and pelleted VLPs were examined by immunoblotting (FIG. 4). While Vpr1SN was expressed in all cells (FIG. 4A, top panel), it was only associated with VLPs derived from cells transfected with pTM-gag1. Similarly, Vpx2SN was detected in all pTM-vpx2 transfected cells (FIG. 4B, top panel), but was only associated with VLPs derived by cotransfection with pTM-gag2 (FIG. 4B, middle panel). HIV-1 and HIV-2 Gag monoclonal antibodies confirmed the presence of Gag precursor protein in each VLP pellet (FIG. 4B, bottom panels). Thus, incorporation of Vpr1SN and Vpx2SN into VLPs requires interaction of the cognate Gag precursor protein, just like native Vpr1 and Vpx2.

Figure 5A:
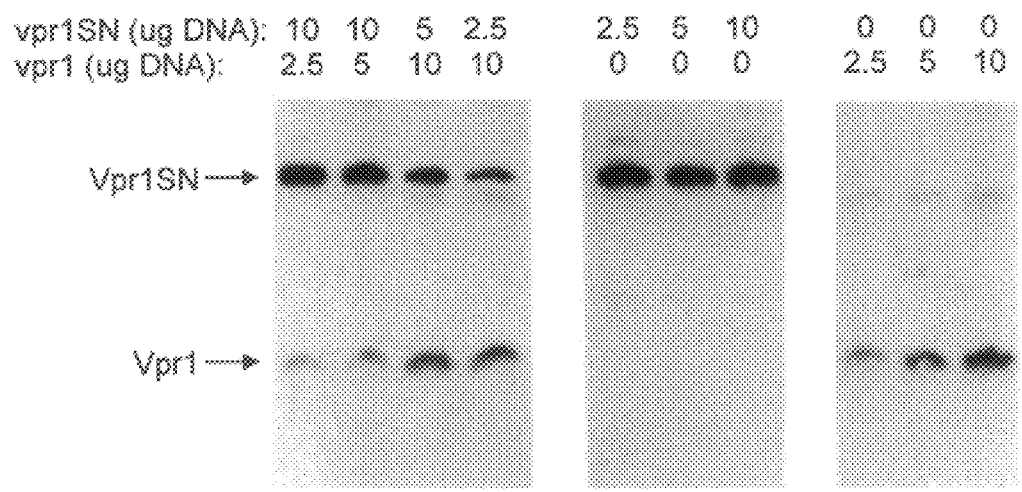
FIG. 5A shows transfection of T7 expressing HeLa cells with different amounts of pTM-vpr1 (2.5, 5 and 10 ug) and pTM-vpr1SN (2.5, 5 and 10 ug), either individually or together in combination with pTM-gag1 (10 ug).
Figure 5B:
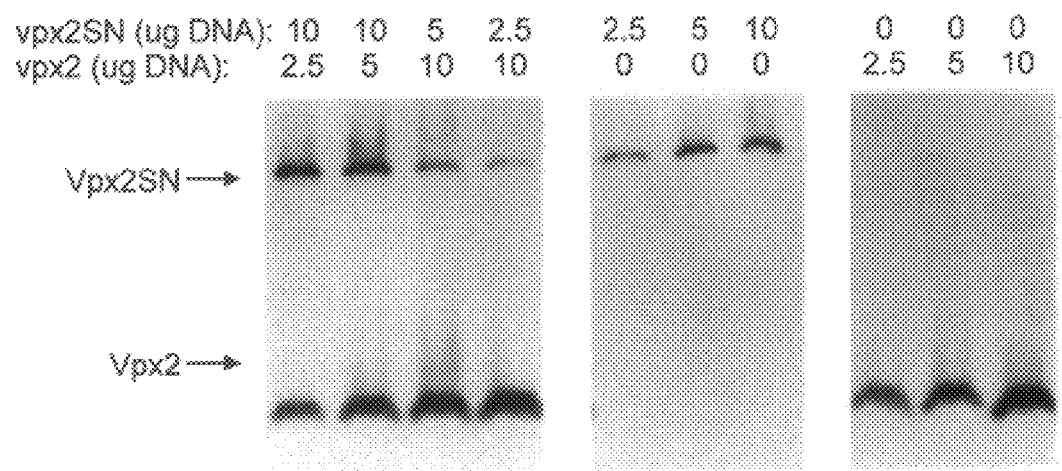
FIG. 5B shows that HeLa cells were transfected with different amounts of pTM-vpx2 (2.5, 5 and 10 ug) and pTM-vpx2SN (2.5, 5 and 10 ug), either individually or together with pTM-gag2 (10 ug). Twenty hours after transfection, particles were concentrated by ultracentrifugation through sucrose cushions and analyzed by immunoblotting using anti-Vpr1 (A) or anti-Vpx2 (B) antibodies.

While Vpr1SN and Vpx2SN fusion proteins clearly associated with VLPs (FIG. 3), the question remained whether they would continue to do so in the presence of the native accessory proteins. The efficiency of Vpr1SN and Vpx2SN packaging was compared by competition analysis (FIG. 5). pTM-vpr1SN and pTM-vpx2SN were cotransfected with pTM-gag1/pTM-vpr1 and pTMgag2/pTM-vpx2, respectively, using ratios that ranged from 1:4 to 4:1 (FIG. 5A and FIG. 5B, left panels). For comparison, pTM-vpr1SN and pTM-vpr1 were transfected individually with pTM-gag1 (FIG. 5A, middle and right panels respectively) and pTM-vpx2SN and pTM-vpx2 were transfected with pTM-gag2 (FIG. 5B, middle and right panels respectively). VLPs were pelleted through sucrose cushions, lysed, separated by PAGE, blotted onto nitrocellulose and probed with anti-SN antibody. The results revealed the presence of both Vpr1 and Vpr1SN in VLPs when cotransfected into the same cells (FIG. 5A, left panel). Similarly, coexpressed Vpx2 and Vpx2SN were also copackaged (FIG. 5B, left panel). Comparison of the relative amounts of VLP-associated Vpr1SN and Vpx2SN when expressed in the presence and absence of the native protein, indicated that there were no significant packaging differences. Thus, Vpr1/Vpx2 fusion proteins can efficiently compete with wild-type proteins for virion incorporation.

EXAMPLE 13

Vpr1SN and Vpx2SN Fusion Proteins Possess Nuclease Activity

To demonstrate that virion associated SN fusion proteins were enzymatically active, VLPs concentrated by ultracentrifugation from culture supernatants of HeLa cells transfected with pTM-gag1/pTM-vpr1SN and pTM-gag2/pTM-vpx2SN were analyzed for nuclease activity using an in vitro DNA digestion assay. Prior to this analysis, immunoblotting confirmed the association of Vpr1SN and Vpx2SN with VLPs (data not shown). FIG. 6 shows lambda phage DNA fragments in 0.8% agarose gels after incubation with dilutions of VLPs lysates that contained Vpr1- or Vpx2- SN fusion proteins. VLPs containing Vpr1SN* and Vpx2SN* were included as negative controls and dilutions of purified SN served as reference standards (FIG. 6A). Both virion associated Vpr1SN (FIG. 6B) and Vpx2SN (FIG. 6C) fusion proteins exhibited nuclease activity as demonstrated by degradation of lambda phage DNA. Cell-associated Vpr1SN and Vpx2SN fusion proteins also possessed nuclease activity when analyzed in this system (data not shown). To control for SN specificity, this analysis was also conducted in buffers devoid of $Ca^{++}$ and under these conditions no SN activity was detected (data not shown). Thus, SN remains enzymatically active when expressed as a fusion protein and packaged into VLPs.

EXAMPLE 14

Incorporation of Vpx2SN fusion protein into HIV-2 virions

Figure 7B:
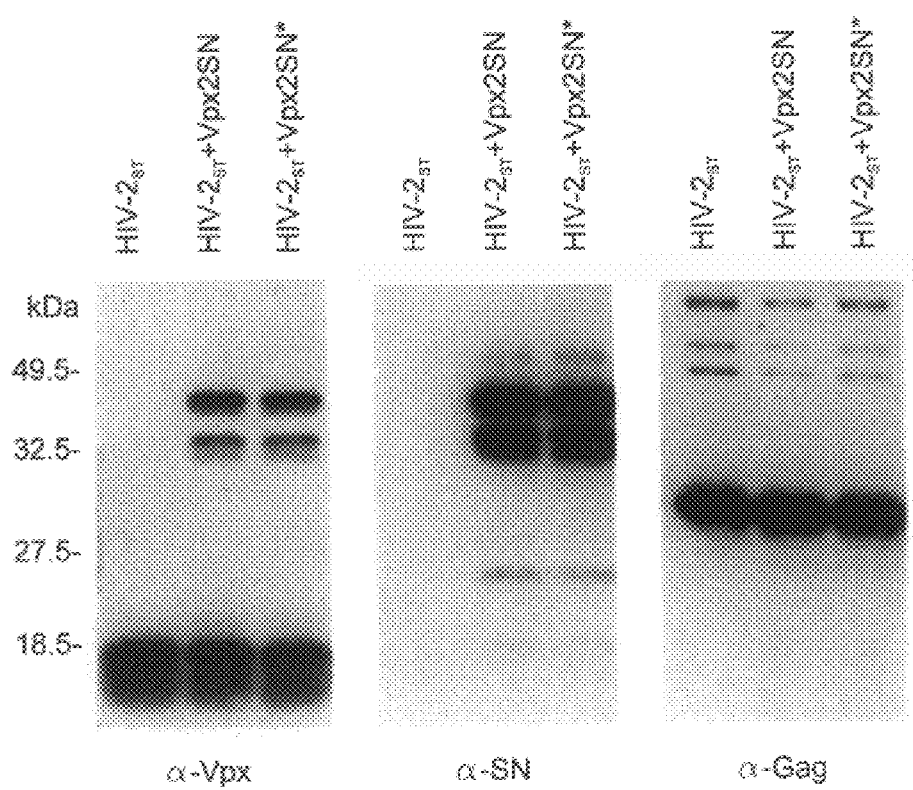
FIG. 7B shows the association of Vpx2SN with HIV-2 virions. Monolayer cultures of HLtat cells were transfected with HIV-2$_{ST}$ proviral DNA (pSXB1) and cotransfected with pSXB1/pTM-vpx2SN and pSXB1/pTM-vpx2SN*. Extracellular virus was concentrated from culture supernatants forty-eight hours after transfection by ultracentrifugation (125,000 ×g, 2 hrs.) through cushions of 20% sucrose. Duplicate Western blots of viral pellets were prepared and probed independently with anti-Vpx2 (left) anti-SN (middle) and anti-Gag (right) antibodies.

Vpx is incorporated into HIV-2 virions when expressed in trans. To show that Vpx2 fusion proteins were similarly capable of packaging into wild-type HIV-2 virions, an expression plasmid (pLR2P) was constructed placing the vpx2SN and vpx2SN* coding regions under control of HIV-2 LTR and RRE elements. The HIV-2 RRE was positioned downstream of the fusion genes to ensure mRNA stability and efficient translation (FIG. 7A). To show that the fusion proteins could package when expressed in trans, HIV-2$_{ST}$ proviral DNA (pSXBI) was transfected alone and in combination with pLR2P-vpx2SN and pLR2P-vpx2SN*. Forty-eight hours later, extracellular virus was pelleted from culture supernatants by ultracentrifugation through cushions of 20% sucrose and examined by immunoblot analysis (FIG. 7B). Duplicate blots were probed using anti-Vpx (left), anti-SN (middle) and anti-Gag (right) antibodies. Anti-Vpx antibody detected the 15 kDa Vpx2 protein in all viral pellets. In virions derived by cotransfection of HIV-2$_{ST}$ with pLR2P-vpx2SN and pLR2P-vpx2SN*, additional proteins of approximately 35 and 32 kDa were clearly visible. The same two proteins were also apparent on a duplicate blot probed with anti-SN antibodies, indicating that they represented Vpx2SN fusion proteins (FIG. 7B, middle panel). The predicted molecular weight of full-length Vpx2SN fusion protein is 33 kDa. As native Vpx and SN run slightly slower than predicted, it is likely that the 35 kDa species represents the full-length Vpx2SN fusion protein. Anti-SN antibodies detected additional proteins of approximately 21 and 17 kDa (these proteins were more apparent after longer exposure). Since only the 35 kDa protein was detected in Gag derived VLPs, which lack Pol proteins (FIG. 2), the smaller proteins represented cleavage products of Vpx2SN and Vpx2SN* generated by the viral protease. Anti-Gag antibodies confirmed the analysis of approximately equivalent amounts of virions from each transfection.

Figure 7C:
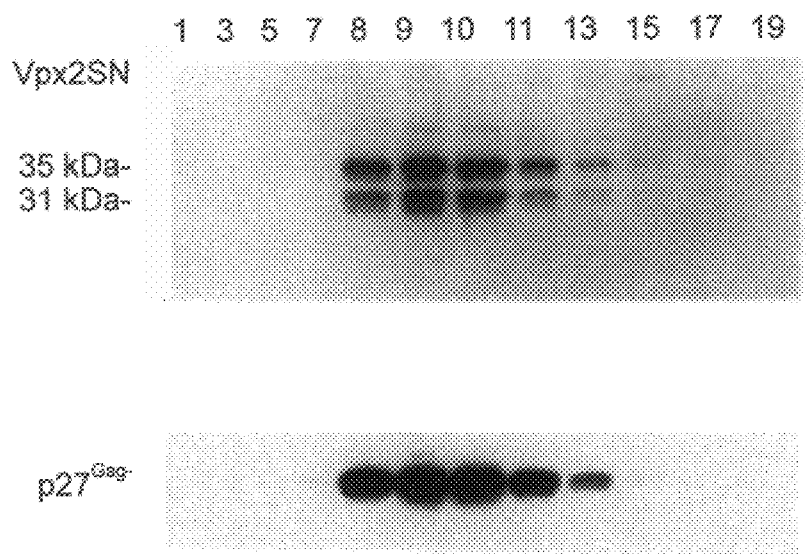
FIG. 7C shows a sucrose gradient analysis. Pellets of supernatant-virus prepared from pSXB1/pTM-vpx2SN cotransfected HLtat cells were resuspended in PBS, layered over a 20–60% linear gradient of sucrose and centrifuged for 18 hours at 125,000×g. Fractions (0.5 ml) were collected from the bottom of the tube, diluted 1:3 in PBS, reprecipitated and solubilized in electrophoresis buffer for immunoblot analysis. Replica blots were probed with anti-SN (top) and anti-Gag (bottom) antibodies. Fraction 1 represents the first collection from the bottom of the gradient and fraction 19 represent the last collection. Only alternate fractions are shown, except at the peak of protein detection.

To show packaging of Vpx2SN into HIV-2 virions, sucrose gradient analysis was performed. Extracellular virus collected from culture supernatants of HLtat cells forty-eight hours after cotransfection with pLR2P-vpx2SN and HIV-2$_{ST}$ was pelleted through cushions of 20% sucrose. Pellets were resuspended in PBS and then centrifuged for 18 hours over linear gradients of 20–60% sucrose. Fractions were collected and analyzed by immunoblotting (FIG. 7C). Duplicate blots were probed separately with anti-SN (top) and anti-Gag (bottom) antibodies. Peak concentrations of both Vpx2SN and Gag were detected in fractions 8–11, demonstrating direct association and packaging of Vpx2SN into HIV-2 virions. These same sucrose fractions (8–11) were found to have densities between 1.16 and 1.17 g/ml, as determined by refractometric analysis (data not shown). Again, both the 35 kDa and 32 kDa forms of Vpx2SN were detected, providing further evidence for protease cleavage following packaging into virus particles.

Figure 7D:
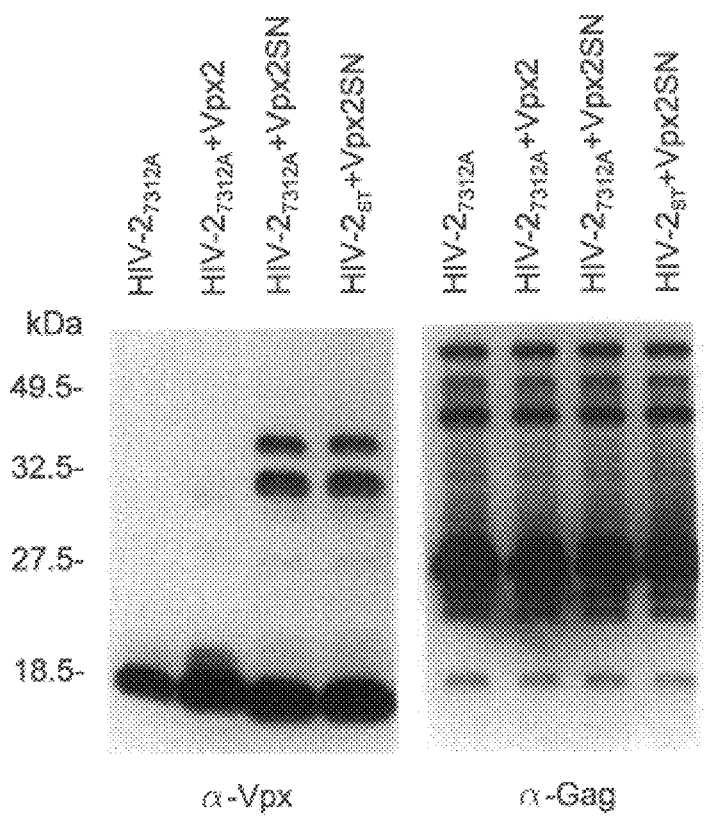
FIG. 7D shows the incorporation of Vpx2SN into HIV-2$_{7312A}$ Vpr and Vpx comptetent virus. Virus concentrated from supernatants of HLtat cells transfected with HIV-2$_{7312A}$ proviral DNA (pJK) or cotransfected with pJK/pLR2P-vpx2SN or pJK/pLR2P-vpx2SN* was prepared for immunoblot analysis as described above. Included for control were virions derived by pSXB1/pLR2P-vpx2SN* cotransfection. Duplicate blots were probed with anti-Vpx (left) and anti-Gag (right) antibodies.

Since HIV-2$_{ST}$ is defective in vpr, this may have affected the packaging of the Vpx2SN fusion protein. A second strain of HIV-2, termed HIV-2$_{7312A}$, was analyzed which was cloned from short-term PBMC culture and contains open reading frames for all genes, including intact vpr and vpx genes (unpublished). A plasmid clone of HIV-2$_{7312A}$ proviral DNA (pJK) was transfected alone and in combination with pLR2P-vpx2SN into HLtat cells. For comparison, HIV-2$_{ST}$ was also co-transfected with pLR2P-vpx2SN. Progeny virus was concentrated by ultracentrifugation through sucrose cushions and examined by immunoblot analysis (FIG. 7D). Duplicate blots were probed with anti-Vpx (left) and anti-Gag (right) antibodies. The results revealed comparable levels of Vpx2SN incorporation into vpr competent virus (HIV-2$_{7312A}$) compared with vpr-defective virus (HIV-2$_{ST}$). Moreover, the 35 kDa and 32 kDa proteins were again detected in HIV-2$_{7312A}$ virions. Thus, efficient incorporation of the Vpx2SN protein into replication-competent wild-type HIV-2 was demonstrated, even in the presence of native Vpr and Vpx proteins.

EXAMPLE 15

Incorporation of Vpr1SN into HIV-1 virions

Using the same LTR/RRE-based expression plasmid, it was also shown that Vpr1SN could package into HIV-1 virions by co-expression with HIV-1 provirus (as discussed above, the HIV-2LTR can be transactivated by HIV-1 Tat and the HIV-2 RRE is sensitive to the HIV-1 Rev protein). Virions released into the culture medium 48 hours after transfection of HLtat cells with pNL4-3 (HIV-1) and pNL4-3-R⁻ (HIV-1R) alone and in combination with pLR2P-vpr1SN were concentrated by ultracentrifugation and examined by immunoblot analysis (FIG. 8). As observed in cotransfection experiments with HIV-2, anti-SN antibodies identified two major Vpr1SN fusion proteins of approximately 34 to 31 kDa. These proteins were not detected in virions produced by transfection of pNL4-3 and pNL4-e-R⁻ alone. From expression in the rVT7 system, the full-length Vpr1SN fusion protein was expected to migrate at 34 kDa. Therefore, the 31 kDa protein likely represents a cleavage product. Anti-SN antibodies also detected a protein migrating at 17 kDa. Anti-Vpr antibody detected the 34 and 31 kDa proteins in virions derived from cotransfected cells. It is noteworthy that both the anti-Vpr and anti-SN antibodies detected the 31 kDa protein most strongly, and that anti-Vpr antibody did not detect the 17 kDa protein recognized by anti-SN antibody. These results also show that even in virions in which native Vpr protein was packaged, Vpr1SN was also incorporated in abundance. Gag monoclonal antibody detected similar amounts of Gag protein in all viral pellets and demonstrated processing of the p55$^{Gag}$ precursor (FIG. 8C).

To demonstrate more directly that cleavage of the Vpr1- and Vpx2-SN fusion proteins was mediated by the HIV protease, virus was concentrated from pNL4-3-R⁻/pLR2P-vpr1SN and pSXB1/pLR2P-vpx2SN transfected cells that were culture in the presence of 1 μM of the HIV protease inhibitor L-689,502 (provided by Dr. E. Emini, Merck & Co., Inc.). As expected, immunoblot analysis of virions demonstrated substantially less processing of p55$^{Gag}$ (FIG. 9A). Similarly, virions produced in the presence of L-689, 502 also contained greater amounts of the uncleaved species of Vpr1SN and Vpx2SN fusion proteins (FIG. 9B). Taken together, these results demonstrate that Vpr1- and Vpx2-SN fusion proteins are subject to protease cleavage during or subsequent to virus assembly.

EXAMPLE 16

Vpr1-CAT and Vpr2-CAT fusion protein incorporation into HIV virions

Figure 10A:
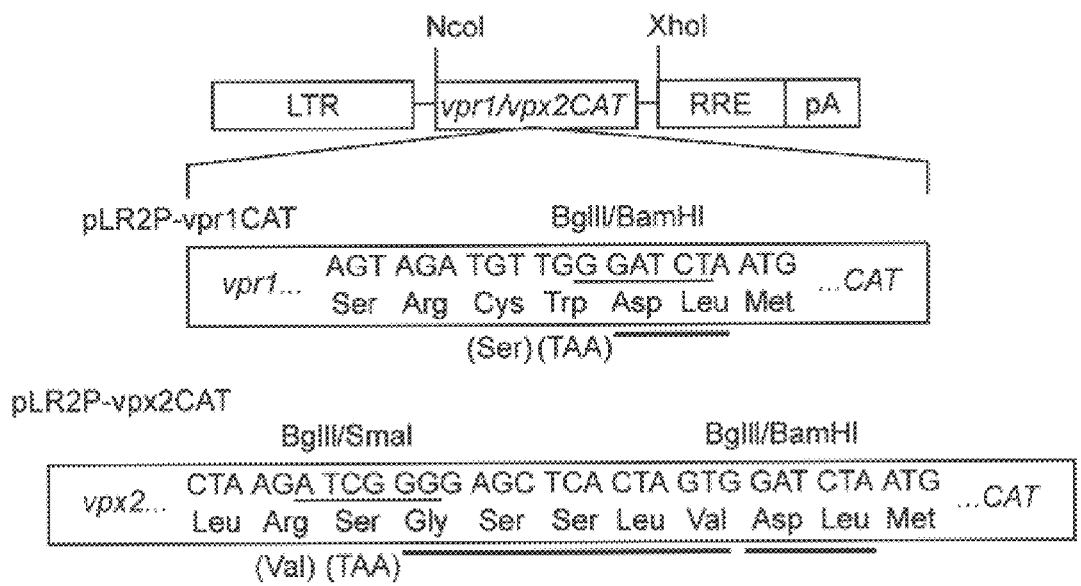
FIG. 10A shows an illustration of the fusion junctions of the pLR2P-vpr1CAT and pLR2P-vpx2CAT expression plasmids (SEQ ID NOS: 15, 16, 17, and 18). PCR amplified BamHI/XhoI DNA fragments containing CAT were ligated into BglII/XhoI cut pLR2P-vpr1SN and pLR2P-vpx2SAN, replacing SN (see FIG. 1). This construction introduced two additional amino acid residues (Asp and Len, above blackened bar) between the vpr1/vpx2CAT coding regions.
Figure 10B:
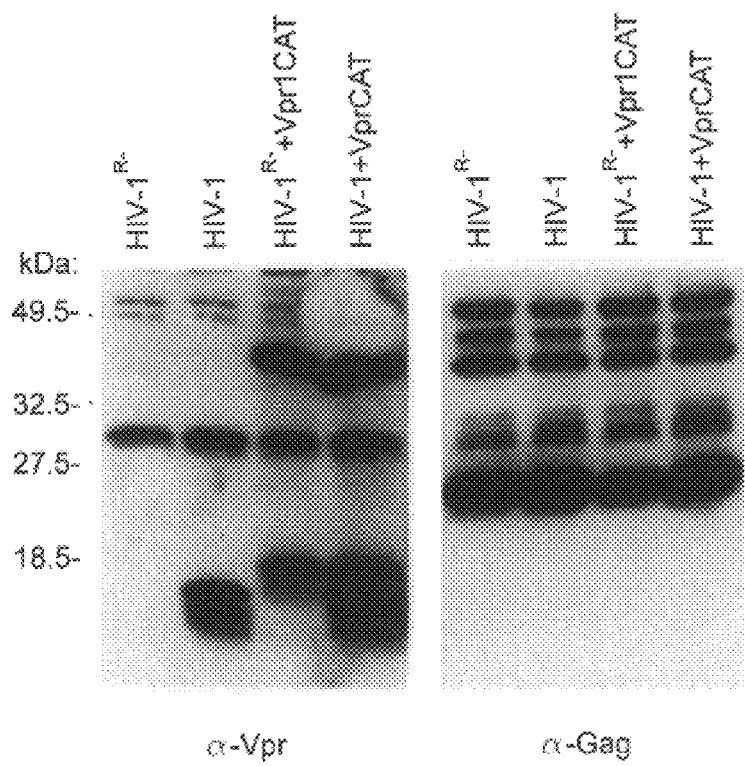
FIG. 10B shows the incorporation of Vpr1CAT into HIV-1 virions. Virus produced from HLtat cells transfected with pNL4–3 (HIV-1) and pNL4–3R (HIV-1-R), or cotransfected with pNL4–3/pLR2P-vpr1CAT and pNL4–3R/pLR2P-vpr1CAT was prepared as described above and examined by immunoblot analysis. Replica blots were probed with anti-Vpr1 (left) and anti-Gag (right) antibodies.
Figure 10C:
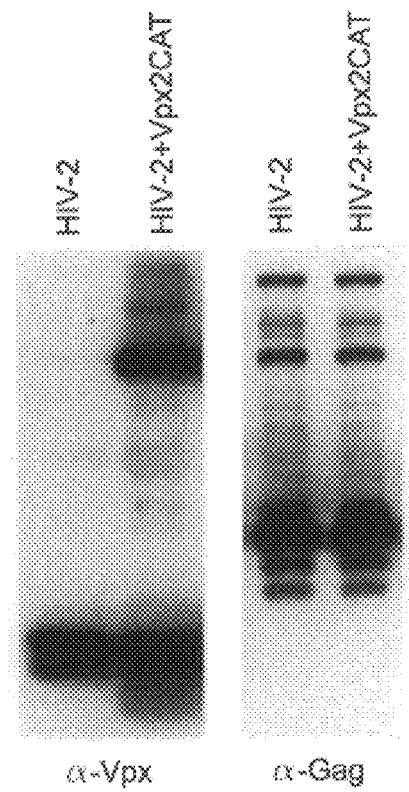
FIG. 10C shows the incorporation of Vpx2CAT into HIV-2 virions. Virus produced from HLtat cells transfected with pSXB1 (HIV-2) or cotransfected with pSXB1/pLR2P-Vpx2CAT was prepared as described above and examined by immunoblot analysis. Replica blots were probed with anti-Vpx2 (left) and anti-Gag (right) antibodies.

To show that Vpx2 and Vpr1 could target additional proteins to the HIV particle, the entire 740 bp CAT gene was substituted for SN in the pLR2P-vpx2SN and pLR2P-vpr1SN vectors, generating pLR2P-vpr1CAT and pLR2P-vpx2CAT (FIG. 10A). pNL4-3/pLR2P-vpr1CAT, pn14-3R⁻/pLR2P-vpr1CAT and pSXB1/pLR2P-vpx2CAT were co-transfected into HLtat cells. As controls, pNL4-3, pNL4-3-R⁻ and pSXB1 were transfected alone. Progeny virions, concentrated from culture supernatants, were analyzed by immunoblotting (FIGS. 10B and 10C). Using anti-Vpr antibodies, 40 kDa fusion proteins were detected in viral pellets derived by co-transfection of pRL2P-vpr1CAT with both pNL4-3 and pNL4-3-R⁻ (FIG. 10B). This size is consistent with the predicted molecular weight of the full-length Vpr1CAT fusion protein. In addition, anti-Vpr antibodies also detected a 17 kDa protein which did not correspond to the molecular weight of native Vpr1 protein (14.5 kDa in virions derived from cells transfected with pNL4-3). The same protein was recognized weakly with anti-CAT antibodies, suggesting a fusion protein cleavage product containing most Vpr sequence. Very similar results were obtained with virions derived from HLtat cells co-transfected with HIV-2$_{ST}$ and pRL2P-vpx2CAT, in which anti-Vpx antibody detected 41 and 15 kDa proteins (FIG. 10C). These results demonstrate that Vpr1CAT and Vpx2CAT fusion proteins are packaged into virions. However, like in the case of SN fusion proteins, CAT fusion proteins were also cleaved by the HIV protease (the Vpx2CAT cleavage product is not visible because of co-migration with the native Vpx protein. CAT cleavage appeared less extensive, based on the intensity of the full-length CAT fusion protein on immunoblots.

Figure 10D:
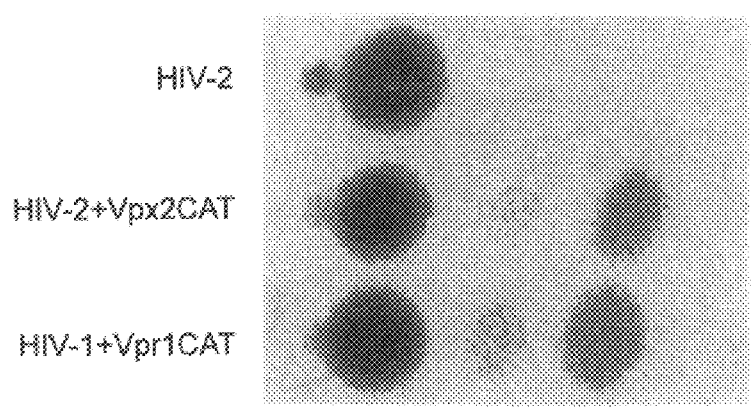
FIG. 10D shows that virion incorporated Vpr1- and Vpx2- CAT fusion proteins posses enzymatic activity. Viruses pelleted from HLtat cells transfected with pSXB1 (HIV-2) or cotransfected with pSXB1/pLR2P-vpx2CAT and pNL4–3/pLR2P-vpr1CAT were lysed and analyzed for CAT activity. HIV-2 was included as a negative control.

Lysates of HIV-1 and HIV-2 viral particles were diluted 1:50 in 20 mM Tris-base and analyzed for CAT activity by the method of Allon, et al. *Nature* 1979, 282:864–860. FIG. 10D indicates that virions which contained Vpr1CAT and Vpx2CAT proteins possessed CAT activity. These results show the packaging of active Vpr1- and Vpr1- and Vpx2-CAT fusion proteins.

EXAMPLE 17

Virion incorporated SN and CAT fusion proteins are enzymatically active

Figure 11A:
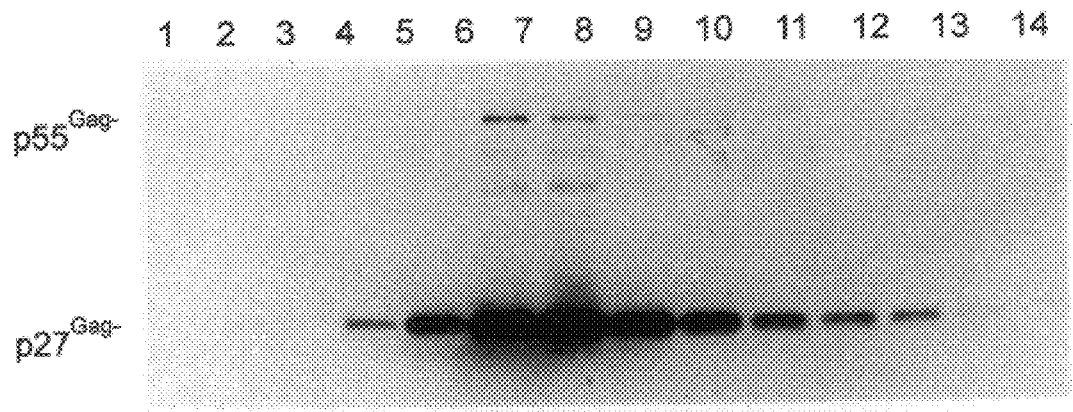
FIG. 11A shows that HIV-2 virions collected from the culture supernatant of HLtat cells cotransfected with pSXB1 and pLR2P-vpx2 were sedimented in linear gradients of 20–60% sucrose. 0.7 ml fractions were collected and analyzed by immunoblot analysis using Gag monoclonal antibodies as a probe.
Figure 11B:
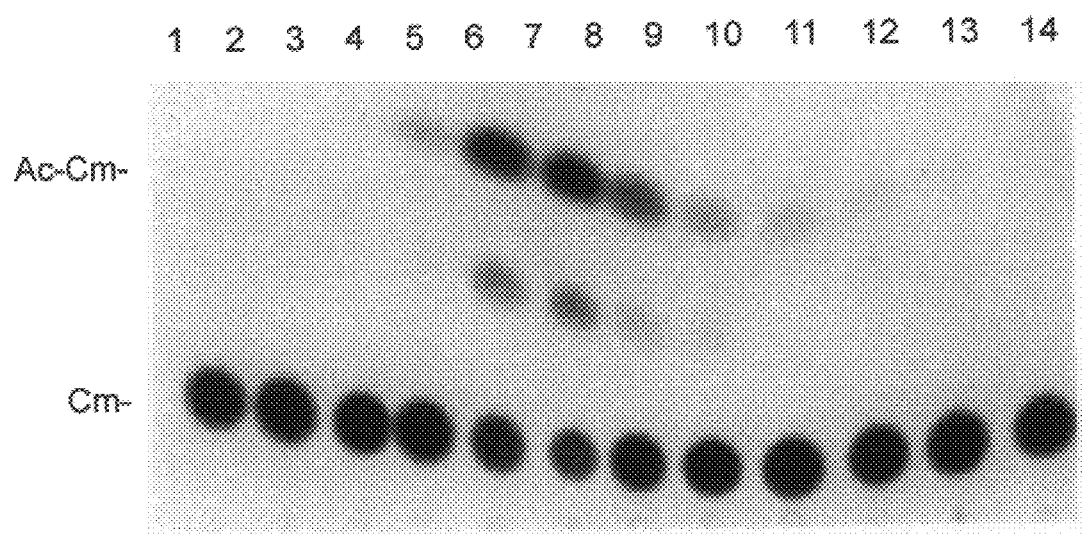
FIG. 11B shows CAT enzyme activity was determined in each fraction by standard methods. The positions of nonacetylated [$^{14}$C] chloramphenicol (Cm) and acetylated chloramphenicol (Ac–Cm) are indicated.

The ability of Vpr1 and Vpx 2 to deliver functionally active proteins to the virus particle was further confirmed by sucrose gradient analysis. Virions derived from HLtat cells co-transfected with HIV-2$_{ST}$ and pLR2P-vpx2 were sedimented in linear gradient of 20–60% sucrose as described above. Fractions were collected and analyzed for viral Gag protein (FIG. 11) and corresponding CAT activity (FIG. 11B). Peak amounts of Gag protein were detected in fractions 6 and 7 (density 1.16 and 1.17, respectively). Similarly, peak amounts of acetylated chloramphenicol (Ac-cm) were also detected in fractions 6 and 7.

Figure 11C:
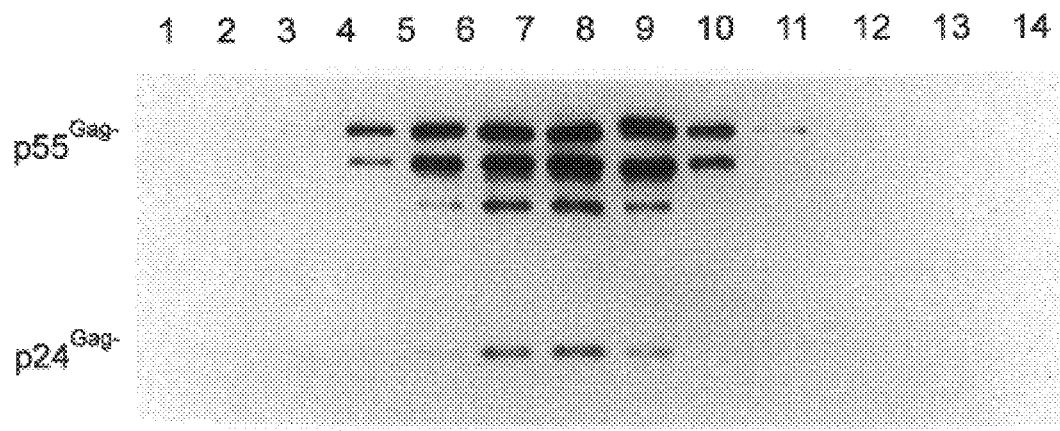
FIG. 11C shows HIV-1 virions derived from HLtat cells cotransfected with pSG3 and pLR2P-vpr1SN and cultured in the presence of L-689,502 were sedimented in linear gradients of 20–60% sucrose. Fractions were collected and analyzed for virus content by immunoblot analysis using Gag monoclonal antibodies.
Figure 11D:
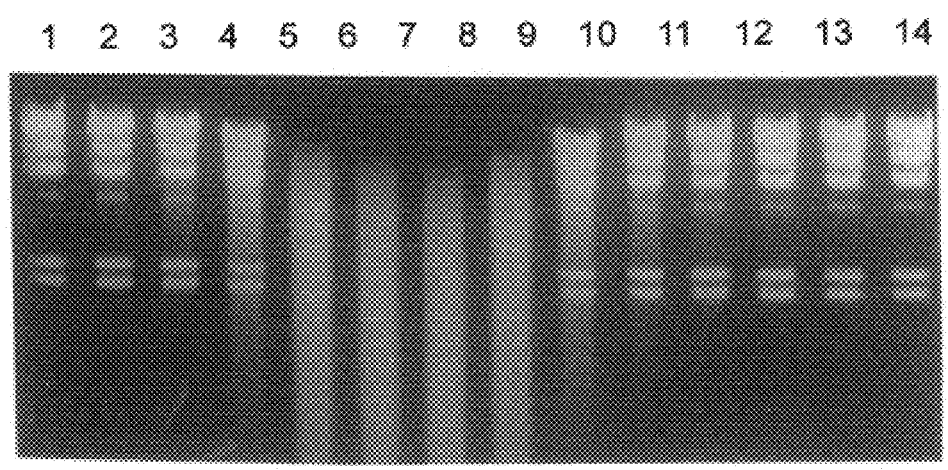
FIG. 11D shows that SN activity was determined in each fraction as described in FIG. 6.

Whether virion associated SN fusion protein retained nuclease activity was also shown. HIV-2$_{SG3}$ virions containing Vpr1SN were analyzed after sedimentation in linear gradients of sucrose (FIG. 11). Since the present invention demonstrated that protease cleavage of SN fusion proteins (FIGS. 7, 8 and 9) markedly reduced Vpr1SN nuclease activity (data not shown), these experiments were performed by culturing pSG3/pLR2P-vpr1SN co-transfected cells in the presence of L-689,502 as described above. Immunoblot analysis of sedimented virions revealed peak concentrations of Gag in fractions 6 and 7 and substantially reduced p55 processing (FIG. 11C). Peak SN activity was associated with the fractions that contained the highest concentrations of virus (FIG. 11D). These results thus document that virion incorporation per se does not abrogate the enzymatic activity of Vpr/Vpx fusion proteins, although cleavage by the viral protease may inactivate the fusion partners.

EXAMPLE 18

Construction and design of a gag-pro (RT-IN minus) packaging plasmid

Several different strategies have been used to express Gag-Pro. Placing Gag and Pro in the same reading frame leads to over expression of Pro and marked cell toxicity. It is known that deletions within the RT and IN coding regions, including smaller deletion mutations, may cause marked defects in the expression levels of the Gag-Pro and Gag-Pol proteins, respectively (Ansari-Lari, M. A. et al., *Virology* 1995, 211:332–335; Ansari-Lari, M. A. et al. *J. Virol.* 1996, 70:3870–3875; Bukovsky, A. et al. *J. Virol.* 1996, 70:6820–6725; Engelman, A. et al. *J. Virol.* 1995, 69:2729–2736; Schell, M. J. et al. *Cell Press* 1997, 90:849–857). Importantly, the viral particles produced under these circumstances are defective in proteolytic processing and are not infectious, even if RT and IN are provided in trans (Wu, X. et al. *J. Virol.* 1994, 68:6161–6169). The reduced levels of expression and virion associated Gag-Pol protein is apparently due to an effect on the frequency of Gag-Pol frame-shifting. Gag-Pol frame-shifting is not markedly affected when the translation of RT and IN is abrogated, which is distinct from deletions of viral DNA fragment. Virions which assembly Gag-Pro, when RT and IN protein synthesis is abrogated by a translational stop codon, mature and are infectious when RT and IN are provided in trans (Wu, X. et al., *J. Virol,* 1994, 68:6161–6169). Therefore, a Gag-Pro packaging plasmid of the present invention is preferably constructed by abrogating translation of sequence downstream of Pro (RT-IN). Other mutations Gag and Pol would also function as part(s) of the trans-lentiviral packaging system if they did not cause major defects in particle assembly and infectivity. In addition to introducing a translational stop codon (TAA) at the first amino acid residue of RT, at least one addition "fatal" mutation is positioned with RT and IN (FIG. 12B). This mutation further decreases the likelihood of reestablishing a complete Gag-Pol coding region by genetic recombination between packaging (gag-pro) and enzymatic (vpr-RT-IN) plasmids. It is appreciated that the stop codon can be inserted within the gene sequence in a position other than at the first codon for the first amino acid residue of a protein and still be an effective measure to prevent infectivity. A stop codon generally inserted with the front half of the amino acid encoding nucleic acid residues is effective, although the stop codon is preferentially at the beginning of the translational sequence. A fatal mutation as used herein refers to a mutation within the gene sequence that render the coded polypeptide sequence functionally ineffectual in performing the biological role of the wild protein.

The Gag-Pro expression plasmid (pCR-gag-pro) includes the CMV promoter and the HIV-2 Rev responsive element (RRE) (FIG. 12C). The RRE allows for the efficient expression of HIV proteins (including Gag, PR, RT, IN) that contain mRNA inhibitory sequences. RT and IN are provided by trans-expression with the pLR2P-vpr-RT-IN expression plasmid (FIG. 12C). This vector expresses the Vpr-RT-IN fusion protein which is incorporated into HIV-1 virions/vector in trans, and is proteolytically processed by the viral protease to generate functional forms of RT (p51 and p66) and IN (Wu, X. et al. *J. Virol.* 1994, 68:6161–6169). This earlier work shows that functional RT and IN can be provided separately (Vpr-RT and Vpr-IN) (Liu, H. et al. *J. Virol.* 1997, 71:7704–7710; Wu, X. et al. *J. Virol.* 1994, 68:6161–6169). Preferably, the Vpr component of the fusion protein contains a His71Arg substitution which knocks out the Vpr cell cycle arrest function.

EXAMPLE 19

Figure 13:
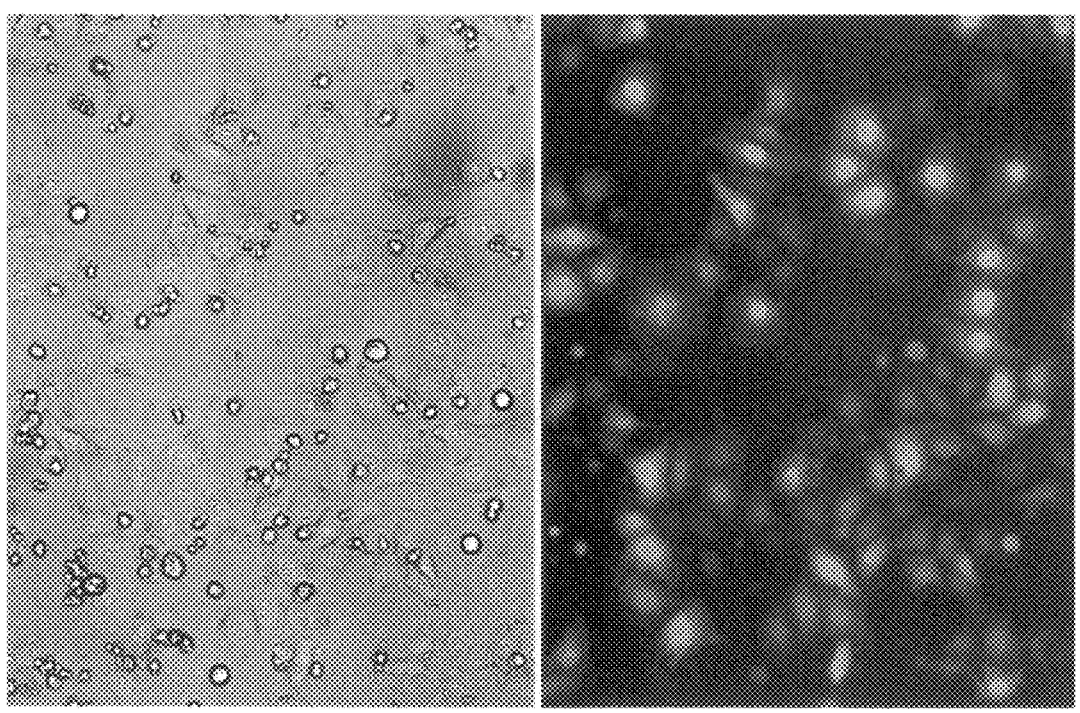
FIG. 13 shows positive gene transduction with a trans-lentiviral vector of the instant invention as determined by fluorescence microscopy.
Figure 14:
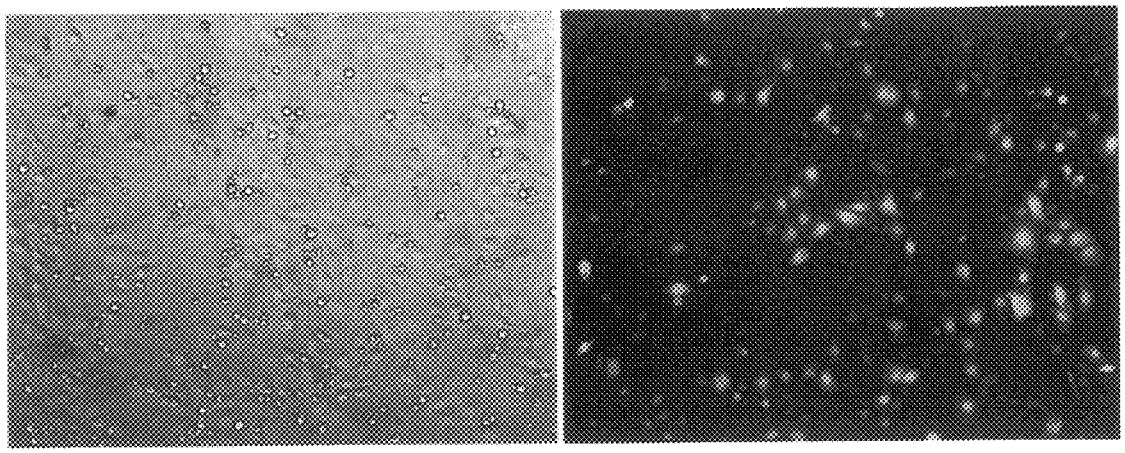
FIG. 14 shows positive gene transduction with a lentiviral vector as a control as determined by fluorescence microscopy.

Production of the trans-lentiviral vector 4 ug each of pCR-gag-pro, pLR2P-vpr-RT-In (enzymatic plasmid), pHR-CMV-β-gal (marker gene transduction plasmid) and pCMV-VSV-G (env plasmid) were transfected into 293T cell line 293T cells were used since they produce high titered stocks of HIV particles/vector and are exquisitely sensitive to transfection, including multiple plasmid transfections. As a control, in side-by-side experiments, the pΔ8.2 packaging plasmid was also transfected with pHR-CMV-β-gal and pCMV-VSV-G (FIG. 12B). The pΔ8.2 plasmid is a lentivirus packaging vector obtained from Dr. D. Trono. The pΔ8.2 produces high titered vector stocks upon transfection with pHR-CMV-β-gal and pCMV-VSV-G (Naldini L. et al. *Science* 1996, 272:263–267; Zhang, J. et al. *Science* 1993, 259:234–238), (approximately 1–5×10$^5$ infectious particles/ml supernatant, with a p24 antigen concentration of 150–800 ng/ml). Approximately 72 hours after transfection, the culture supernatants were harvested, clarified by low-speed centrifugation, filtered through a 0.45 micron filter, and analyzed for p24 antigen concentration by ELISA. To examiner the titer of the trans-lentiviral vector, supernatant stocks of 24, 5, 1, and 0.2 ul were used to infect cultures of HeLa cells and IB3 cells. Two days later, the cells are stained with X-gal, and positive (blue) cells are counted using a light microscope. Table 3 shows that the titer of trans-lentiviral vector. These results show that the trans-lentiviral vector can achieve titers as high as 2×10$^5$/ml, although its titer is consistently lower than that of lentiviral vector (2–5 folds less). For direct examination of transduction in living cells the transduction plasmid was also constructed to contain the GFP gene/marker (FIG. 12B and 12C). Stocks of trans-lentiviral and lentiviral vector were produced as described above and used to infect HeLa cells. Two days later the cells were examined by fluorescence microscopy. FIGS. 13 and 14 show positive gene transduction with the trans-lenti and lentiviral vectors respectively.

TABLE 3

Generation of Trans-Lentiviral Vector

| Packaging Plasmid | RT-IN Plasmid | Titer (inf. units/ml × 10$^{-5}$) | |
|---|---|---|---|
| | | HeLa | IB3 |
| pCMVΔR9 | — | 2.5 (+/−5.1) | 1.2 (+/−2.7) |
| pCMVΔR9-S$^{RT-IN}$ | — | 0 | 0 |
| pCMVΔR9-S$^{RT-IN}$ | Vpr-RT-IN | 1.1 (+/−3.1) | 0.8 (+/−2.5) |

EXAMPLE 20

Construction of trans-lentiviral vector by ultracentrifugation

To examine whether the trans-lentiviral vector was stable during the concentration by ultracentrifugation, the supernatant-trans-lentiviral vector was concentrated by ultracentrifugation (SW28, 23,000 rpm, 90 min., 4° C.). As a control supernatant-lentiviral vector was concentrated in parallel. The titers for both were determined both before and after concentration. Table 4 shows our results and indicates that the trans-lentiviral vector is stable during concentration by ultracentrifugation.

TABLE 4

Concentration of Trans-Lentiviral Vector

| Packaging Plasmid | RT-IN Plasmid | Titer (inf. units/ml × 10$^{-5}$) | |
|---|---|---|---|
| | | HeLa | IB3 |
| pCMVΔR9 | — | 54 | 31 |
| pCMVΔR9-S$^{RT-IN}$ | Vpr-RT-IN | 28 | 19 |

EXAMPLE 21

Trans-lentiviral vector for CFTR gene transduction

Figure 15:
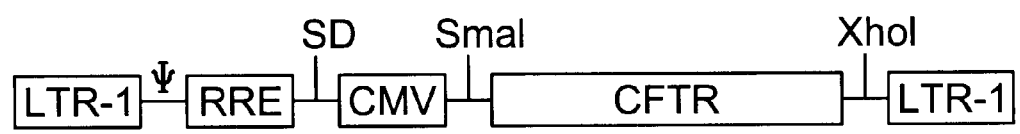
FIG. 15 shows the construction of a pHR-CFTR trans-lentiviral vector of the present invention.
Figure 16:
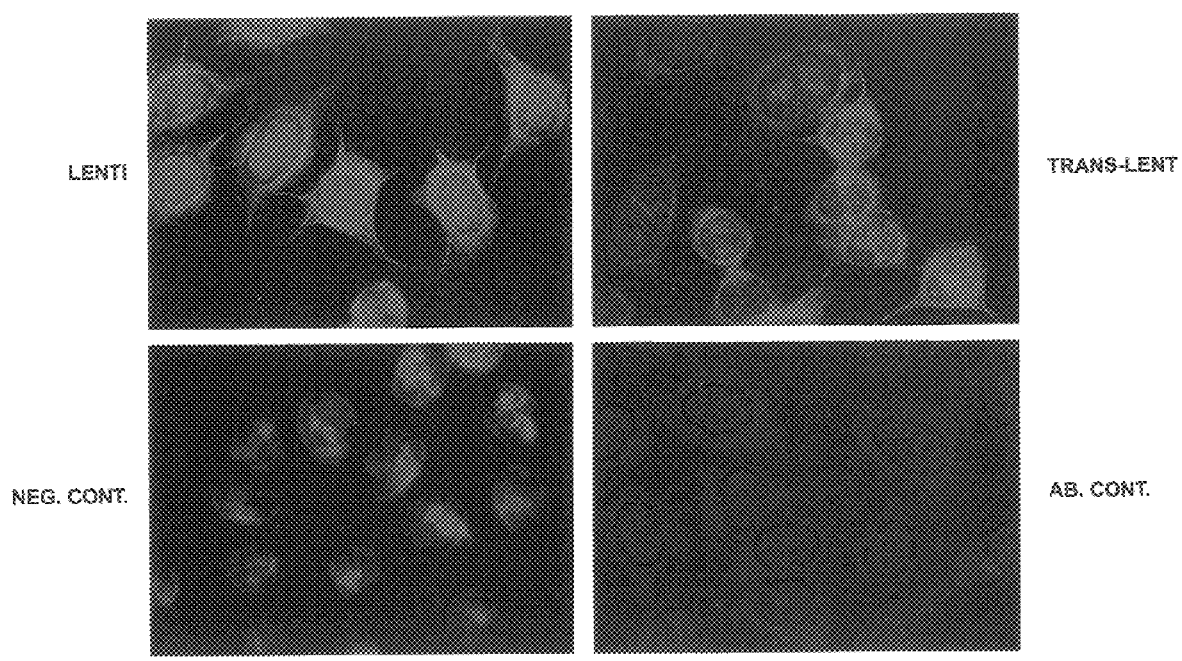
FIG. 16 shows the expression of CFTR on HeLa cells using the trans-lentiviral vector, and the lentiviral vector as a control. Transduced cells were probed with polyclonal antibodies in immunofluorescence microscopy.
Figure 17:
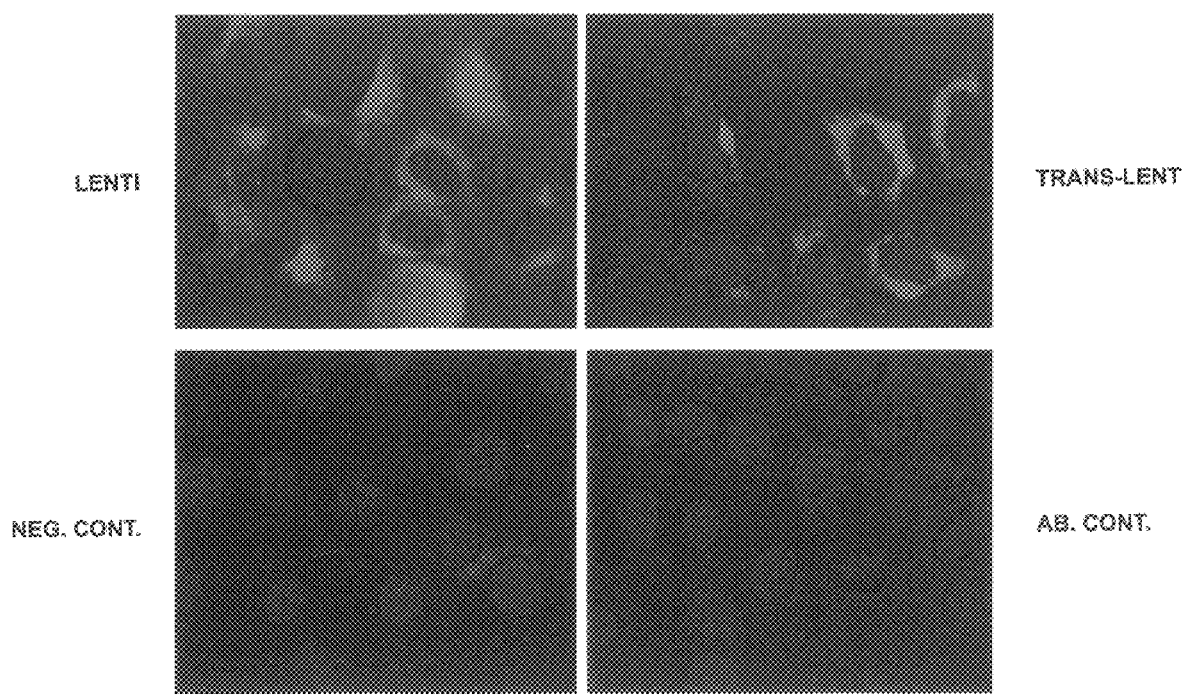
FIG. 17 shows the expression of CFTR on HeLa cells using monoclonal antibodies in immunofluorescence microscopy.
Figure 18:
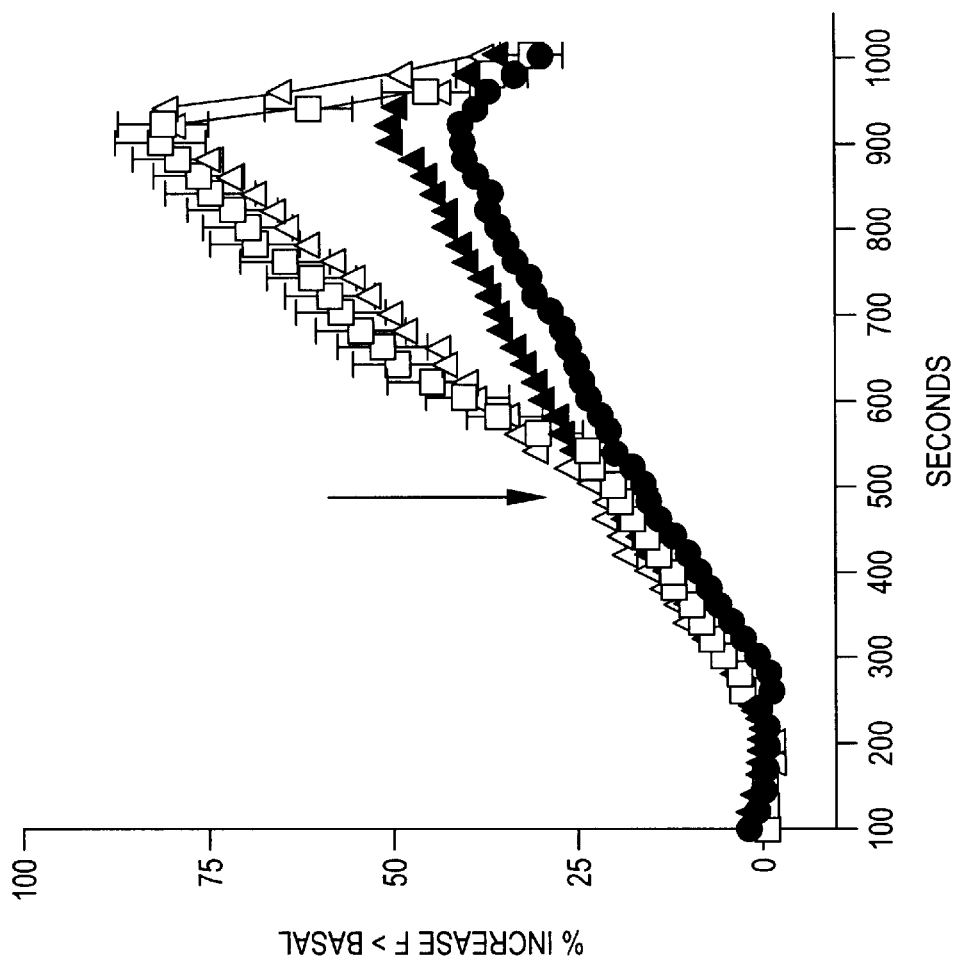
FIG. 18 shows the restoration of CFTR function in trans-lentiviral transduced HeLa cells as measured by a halide sensitive fluorophore.

Lentiviral-based vectors are attractive for use in the lung due to their ability to transduce non-divided cells. This unique characteristic may represent an important advantage of lentiviral vectors for gene therapy of CF. A trans-lentiviral vector was used to deliver the CFTR gene into HeLa cells. The CFTR gene was cloned into the pHR transduction plasmid, using SmaI and XhoI sites (FIG. 15). Trans-lentiviral and lentiviral (as control) vectors were generated by transfection as described above, and used to transduce HeLa cells grown on cover slips. Two days later the cells were examined by immunofluorescene microscopy, using both polyclonal (FIG. 16) and monoclonal antibodies (FIG. 17). The results show CFTR expression and localization of CFTR on the cell surface. Furthermore, the transduced HeLa cells examined by SPQ (halide-sensitive fluorophore) showed restored CFTR function (FIG. 18).

The present invention demonstrated the capability of HIV-1 Vpr and HIV-2 Vpx to direct the packaging of foreign proteins into HIV virions when expressed as heterologous fusion molecules. The trans complementation experiments with HIV proviral DNA revealed that Vpr1 and Vpx2 fusion proteins were also incorporated into replication-competent viruses. Moreover, packaging of the fusion proteins in the presence of wild-type Vpx and/or Vpr proteins (FIGS. 16 and 17) indicated that the viral signals mediating their packaging were not obstructed by the foreign components of the fusion molecules. Likewise, virion-associated SN and CAT fusion proteins remained enzymatically active.

Based on the immunoblot analysis of VLPs and virions, the present invention illustrates that both virion associated CAT and SN/SN* are susceptible to cleave by the viral protease. There appears to be at least one cleavage site in CAT and two cleavage sites in the SN/SN* proteins. Based on calculated molecular weights of the major SN/SN* cleavage products, it appears that SN and SN* are cleaved one near their C termini and once near the fusion protein junctions. Since the fusion protein junctions of Vpr1SN and Vpx2SN are not identical it is also possible that these regions differ with respect to their susceptibility to the viral protease. Although Vpx2SN/SN* were processed to a lesser extent than Vpr1SN (FIGS. 7 and 8), the major cleavage sites appear to be conserved. There is not doubt that both the HIV-1 and HIV-2 proteases recognize processing sites in the fusion partners and that there is sufficient physical contact to enable cleavage. This is evidenced both by the reduction of cleavage product intensities on immunoblots as well as by an increased enzymatic activity in the presence of an HIV protease inhibitor.

The demonstration that Vpr1 and Vpx2 fusion proteins are capable of associating with both VLPs and virions facilitates studies on these accessory proteins and on HIV assembly in general. The approach of generating deletion mutants to study protein structure/function relationships is often of limited value since this can reduce protein stability or change the three-dimensional structure of the protein. In the case of Vpr, a single amino acid substitution at residue 76 has been shown to destabilize its expression in infected cells. Studies have indicated that deletion mutations in vpr and vpx result in premature degradation of the proteins following expression. Fusion of Vpr and Vpx mutant proteins with, e.g., SN or CAT as demonstrated by the present invention, increase stability.

The successful packaging of Vpr1/Vpx2SN fusion proteins into virions indicates their use for accessory protein targeted viral inactivation. The present invention demonstrates the Vpr and Vpx may serve as vehicles for specific targeting of virus inhibitory molecules, including SN. In contrast to HIV Gag, Vpr and Vpx are small proteins that can be manipulated relatively easily without altering virus replication and thus may represent vehicles with considerable versatility for application to such an antiviral strategy.

EXAMPLE 22

Figure 19A:
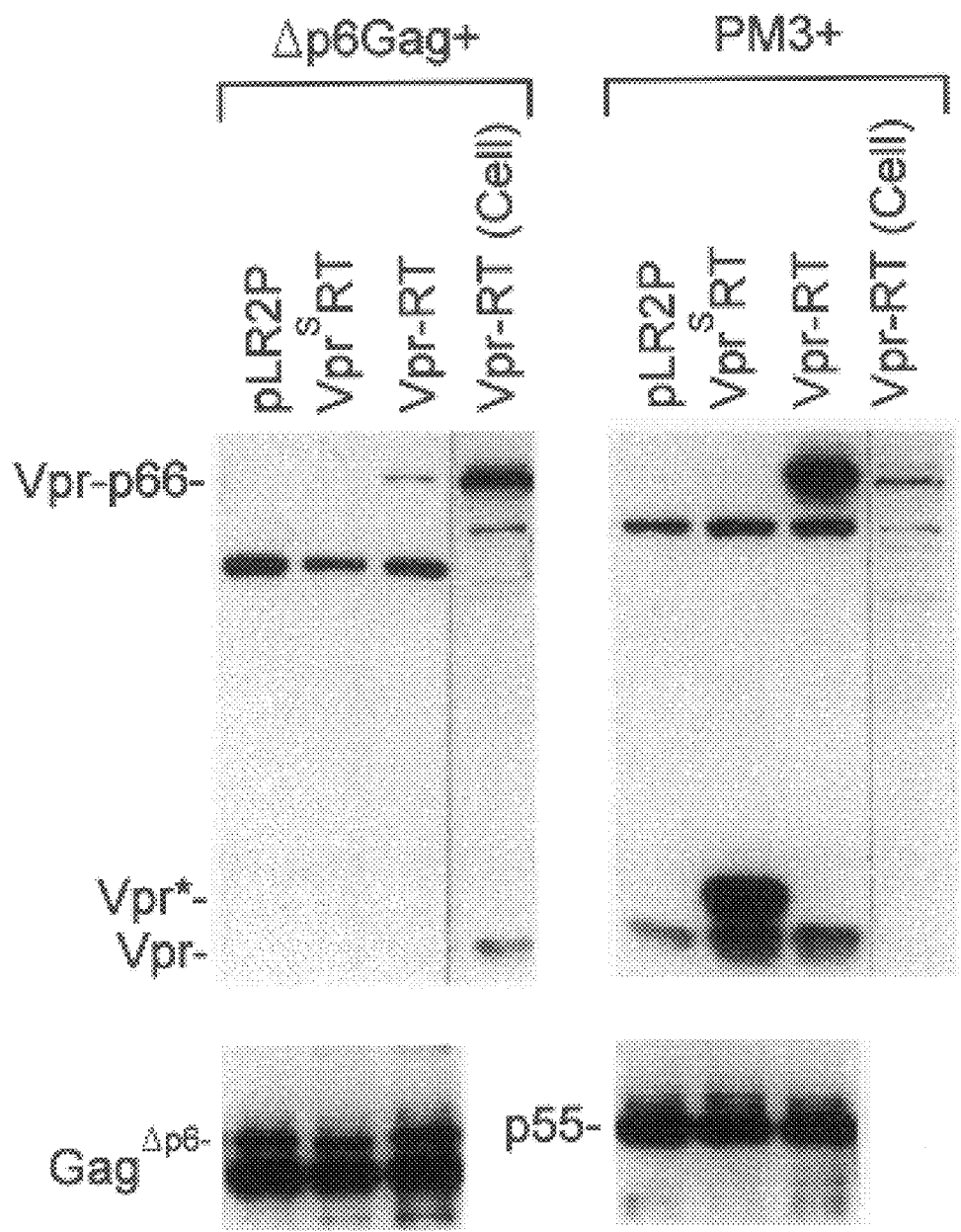
FIGS. 19A and B show the presence in progeny virions of RT in trans without Vpr-dependent incorporation.
Figure 19B:
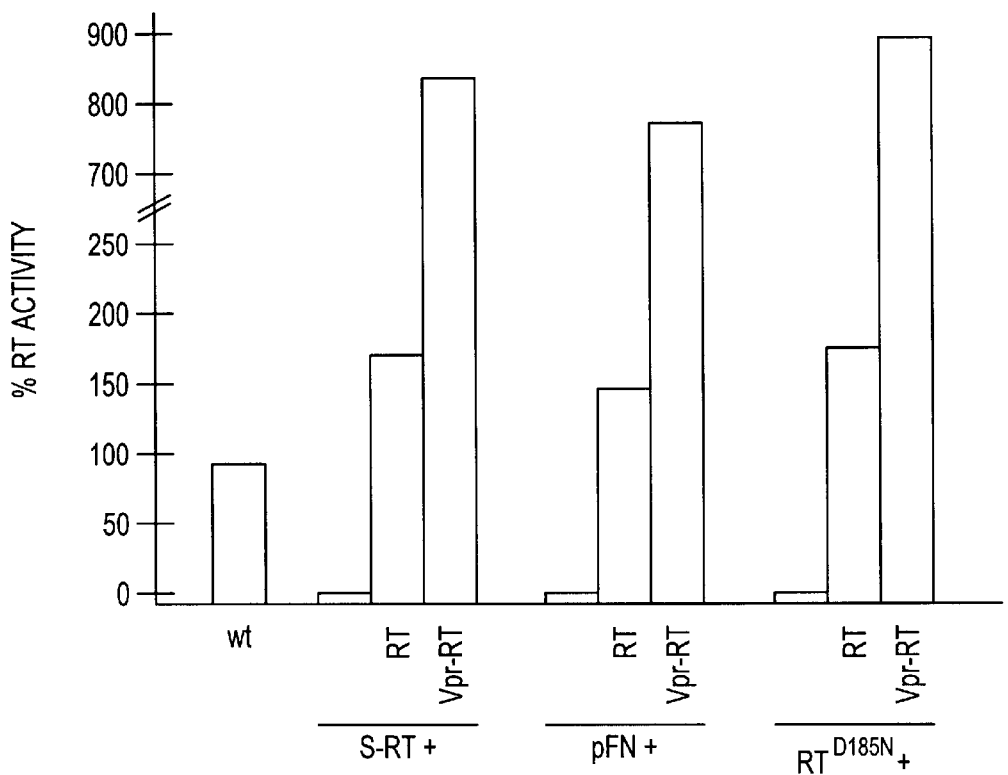

Incorporation of RT in trans into a lentivirus independent of HIV accessory proteins The HIV accessory proteins, Vpr and Vpx, are incorporated into virions through specific interactions with the p6 portion of the $Pr55^{Gag}$ precursor protein (Kappes et al. [cite] 1993; Kondo et al. J. Virol. 1995, 69:2759–2764; Lu et al. J. Virol. 1995, 69:6873–6879; Paxton et al., J. Virol, 1993, 67:7229–7237; Wu et al. J. Virol. 1994, 68:6161–6169). Similarly, it has been demonstrated that Vpr and Vpx fusion proteins (Vpr- and Vpx- SN and CAT) are incorporated into virions through interactions with $p6^{Gag}$, similar to that of the wild-type Vpr and Vpx proteins (Wu et al. J. Virol. 1995, 69:3389–3398). To analyze the contribution of Vpr for incorporation of the Vpr-RT fusion protein into virions, an HIV-1 proviral clone mutated in $p6^{Gag}$ and PR (designated pNL43-Δ $p6^{Gag}$, provided by Dr. Mingjun Huang) was cotransfected with pLR2P-vprRT into 293T cells. This mutant contains a TAA translational stop codon at the first amino acid residue position of $p6^{Gag}$. This abrogated the Gag sequences that are required for Vpr virion incorporation. The pNL43-Δ $p6^{Gag}$ clone also contains a mutation (D25N) in the active site of PR, which enhances the release of the $p6^{Gag}$ mutant virus from the cell surface membrane (G ettlinger et al. [cite] 1991; Huang et al. [cite] 1995). As a control, The HIV-1 PR mutant PM3 (Kohl et al. [cite] 1988), derived from the same pNL4-3 parental clone, was also included for analysis. Progeny virions, purified from pNL43-Δ $p6^{Gag}$ transfected cell cultures, contained detectable amounts of RT protein (labeled as Vpr-p66), albeit in lesser amounts compared with virions derived from PM3 (FIG. 19). Analysis of cell lysates confirmed expression, and compared with PM3, the accumulation of Vpr-RT in pLR2P-vprRT/pNL43-Δ $p6^{Gag}$ cotransfected cells. $Vpr^S$-RT was included as an additional control and was shown to incorporate Vpr efficiently into PM3 virions but not into those derived by coexpression with pNL43-Δ $p6^{Gag}$. Wild-type Vpr protein was also absent from Δ $p6^{Gag}$ virions. Approximately equal amounts of Gag protein was detected in the different virus pellets, confirming that similar amounts of the different virions were compared in the quantitation. These results show that RT protein can be incorporated into virions independently of Vpr-p6 mediated interaction. These data also indicate that expression of RT (and IN by inference) in trans, independently of Gag-Pol, is sufficient for its incorporation and function.

EXAMPLE 23

Expression of RT in trans in a lentivirus vector independent of HIV accessory

Figure 20:
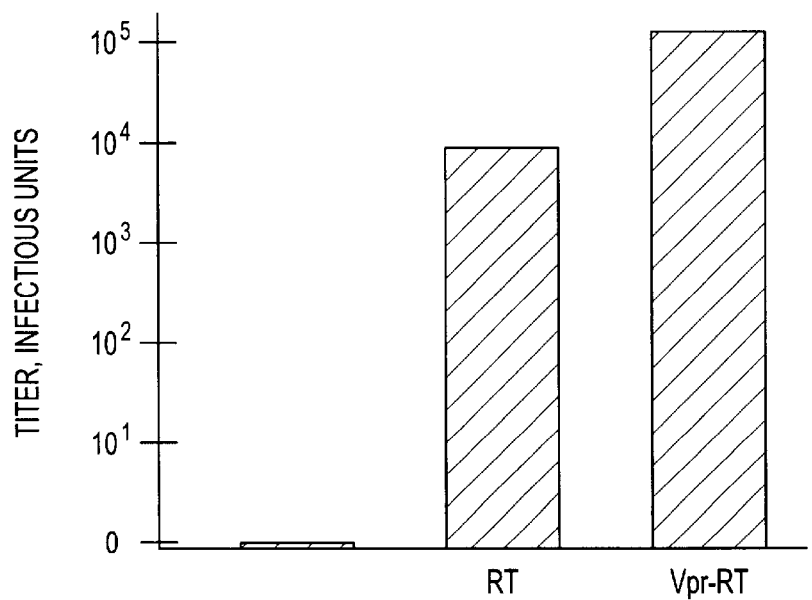
FIG. 20 shows that both Vpr-RT and RT support vector transduction when provided in trans.

It has been demonstrated that functional RT can be incorporated into HIV-1 virions by its expression in trans, fever without fusion to Vpr (Example 19). To determine if RT expressed in trans can package into lentiviral vector and support the transduction of a marker gene RT was ligated into the pLR2P expression plasmid under control of the HIV LTR and RRE, generating the pLR2P-RT expression plasmid. The pLR2P-RT, pHR-CMV-VSV-G, pHR-CMV-β-gal, and $pΔ8.2-RT^{D185N}$ was transfected together into 293T cells. The $pΔ8.2-RT^{D185N}$ plasmid contains a point mutation in RT at amino acid residue position 185 (D185N), which abolishes polymerase activity and destroys its ability to support gene transduction. As a control Vpr-RT (pLR2P-vpr-RT) was substituted for pLR2P-RT in a parallel experiment. As another control neither RT or Vpr-RT were provided. Virions generated by transfection were used to infect HeLa cells. Two days later, transduction positive cells were counted. FIG. 20 shows that both Vpr-RT and RT support vector transduction when provided in trans. The vector titer was reduced by about 10-fold when RT was provided without fusion with Vpr. These results demonstrate that enzymatic function (RT and IN) can be provided in trans, independently of Gag-Pol.

The present invention demonstrated that Vpr and Vpx can serve as vehicles to deliver functionally active enzymes to the HIV virion, including those that may exert an antiviral activity such as SN. The present invention has demonstrated that the concept of accessory protein targeted virus inactivation is feasible.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A transretroviral vector system comprising: at least a first nucleic acid segment encoding at least one fusion protein comprising at least a functional portion of a first truncated Gag protein fused in frame to a functional portion of a reverse transcriptase polypeptide having reverse transcriptase activity fused in frame to a functional portion of an integrase polypeptide having integrase activity, said first nucleic acid segment capable of expression in a mammalian cell, said functional portion of said first Gag protein capable of providing for the incorporation of said fusion protein into a viral particle.

2. The transretroviral vector system of claim 1 further comprising at least a second nucleic acid segment comprising a nucleic acid sequence encoding at least a functional portion of a second Gag polypeptide and a functional portion of a protease polypeptide, said second nucleic acid segment provided on the same or a different nucleic acid strand than said first segment, said second nucleic acid segment capable of expression in said mammalian cell, said functional portion of said second Gag polypeptide and said protease are capable of supporting the formation of an infectious viral particle, and wherein said second nucleic acid segment does not encode a functional Reverse Transcriptase polypeptide or a functional Integrase polypeptide.

3. The transretroviral vector system according to claim 2 further comprising at least a third nucleic acid segment comprising a nucleic acid sequence encoding an envelope polypeptide, said third nucleic acid segment provided on a different or the same nucleic acid strand as said first and said second nucleic acid segments.

4. The transretroviral vector system according to claim 3 further comprising at least a fourth nucleic acid segment comprising a nucleic acid sequence of interest and at least one cis acting nucleic acid sequence functioning in packaging, reverse transcription and integration of said fourth nucleic acid segment into the genome of a target cell.

5. The transretroviral vector system according to claim 4 wherein said fourth nucleic acid segment further comprises a promoter sequence active in the target cell and operably linked to the nucleotide sequence of interest and at least one nucleic acid sequence for facilitating transduction of said fourth nucleic acid segment into the target cell.

6. The transretroviral vector system according to any of claims 2, 3, or 4 wherein said functional portions of said first and said second Gag protein and said protease are from a retrovirus.

7. The transretroviral vector of claim 5 wherein said nucleic acid sequences for facilitating transduction are selected from the group consisting of PPT-CTS and WPRE.

8. The transretroviral vector system according to claim 6 wherein said retrovirus is selected from the group consisting of HIV, SIV, EIAV, BIV, FIV, and MLV.

9. A transretroviral vector system comprising:
(a) at least a first nucleic acid segment encoding at least one fusion protein comprising at least a functional portion of a first truncated Gag protein fused in frame to a functional portion of a reverse transcriptase polypeptide having reverse transcriptase activity fused in frame to a functional portion of an integrase polypeptide having integrase activity, said first nucleic acid segment capable of expression in a mammalian cell, said functional portion of said first Gag protein capable of providing for the incorporation of said fusion protein into a viral particle; and,
(b) at least a second nucleic acid segment comprising a nucleic acid sequence encoding at least a functional portion of a second Gag polypeptide and a functional portion of a protease polypeptide, said second nucleic acid segment provided on the same or a different nucleic acid strand than said first nucleic acid segment, said second nucleic acid segment capable of expression in said mammalian cell, said functional portion of said second Gag polypeptide and said protease polypeptide are capable of supporting the formation of an infectious viral particle, and wherein said second nucleic acid segment does not encode a functional Reverse Transcriptase polypeptide or a functional Integrase polypeptide.

10. The transretroviral vector system according to claim 9 further comprising at least a third nucleic acid segment comprising a nucleic acid sequence encoding an envelope polypeptide, said third nucleic acid segment provided on a different or the same nucleic acid strand as said first and said second nucleic acid segments.

11. The transretroviral system according to claim 10 further comprising at least a fourth nucleic acid segment comprising a nucleic acid sequence of interest and at least one cis acting nucleic acid sequence functioning in packaging, reverse transcription and integration of said fourth nucleic acid segment into the genome of a target cell.

12. The transretroviral system according to claim 11 wherein said fourth nucleic acid segment further comprises a promoter sequence active in the target cell and operably linked to said nucleotide sequence of interest and at least one nucleic acid sequence for facilitating transduction of said fourth segment into the target cell.

13. The transretroviral system according to any of claims 9, 10, or 11 wherein said functional portions of said first and said second Gag protein and said protease polypeptide are from a retrovirus.

14. The transretroviral system of claim 12 wherein said nucleic acid sequences for facilitating transduction are selected from the group consisting of PPT-CTS and WPRE.

15. The transretroviral vector system according to claim 13 wherein said retrovirus is selected from the group consisting of HIV, SIV, EIAV, BIV, FIV, and MLV.

16. A transretroviral vector system comprising:
(a) at least a first nucleic acid segment encoding at least one fusion protein comprising at least a functional portion of a first truncated Gag protein fused in frame to a functional portion of a reverse transcriptase polypeptide having reverse transcriptase activity fused in frame to a functional portion of an integrase polypeptide having integrase activity, said first segment capable of expression in a mammalian cell, said functional portion of said first Gag protein capable of providing for the incorporation of said fusion protein into a viral particle;
(b) at least a second nucleic acid segment comprising a nucleic acid sequence encoding at least a functional portion of a second Gag polypeptide and a functional portion of a protease polypeptide, said second nucleic acid segment provided on the same or a different nucleic acid strand than said first segment, said second nucleic acid segment capable of expression in said mammalian cell, said functional portion of said second Gag polypeptide and said protease polypeptide are capable of supporting the formation of an infectious viral particle and wherein said second nucleic acid segment does not encode a functional Reverse Transcriptase polypeptide or a functional Integrase polypeptide; and
(c) at least a third nucleic acid segment comprising a nucleic acid sequence encoding an envelope polypeptide, said third nucleic acid segment provided on a different or the same nucleic acid strand as said first and said second nucleic acid segments.

17. The transretroviral vector system according to claim 16 further comprising at least a fourth nucleic acid segment comprising a nucleic acid sequence of interest and at least one cis acting nucleic acid sequence functioning in packaging, reverse transcription and integration of said fourth nucleic acid segment into the genome of a target cell.

18. The transretroviral vector system according to claim 17 wherein said fourth nucleic acid segment further comprises a promoter sequence active in the target cell and operably linked to the nucleotide sequence of interest and at least one nucleic acid sequence for facilitating transduction of said fourth segment into the target cell.

19. The transretroviral vector system according to any of claims 16 or 17 wherein said functional portions of said first and said second Gag protein and said protease polypeptide are from a retrovirus.

20. The transretroviral vector of claim 18 wherein said nucleic acid sequences for facilitating transduction are selected from the group consisting of PPT-CTS and WPRE.

21. The transretroviral vector system according to claim 19 wherein said retrovirus is selected from the group consisting of HIV, SIV, EIAV, BIV, FIV, and MLV.

22. A transretroviral vector system comprising:
   (a) at least a first nucleic acid segment encoding at least one fusion protein comprising at least a functional portion of a first truncated Gag protein fused in frame to a functional portion of a reverse transcriptase polypeptide having reverse transcriptase activity fused in frame to a functional portion of an integrase polypeptide having integrase activity, said first nucleic acid segment capable of expression in a mammalian cell, said functional portion of said first Gag protein capable of providing for the incorporation of said fusion protein into a viral particle;
   (b) at least a second nucleic acid segment comprising a nucleotide sequence encoding at least a functional portion of a second Gag polypeptide and a functional portion of a protease polypeptide, said second nucleic acid segment provided on the same or a different nucleic acid strand than said first segment, said second nucleic acid segment capable of expression in said mammalian cell, said functional portion of said second Gag polypeptide and said protease polypeptide are capable of supporting the formation of an infectious viral particle, and wherein said second nucleic acid segment does not encode a functional Reverse Transcriptase polypeptide or a functional Integrase polypeptide;
   (c) at least a third nucleic acid segment comprising a nucleic acid sequence encoding an envelope polypeptide, said segment provided on a different or same nucleic acid strand as said first and said second nucleic acid segments; and
   (d) at least a fourth nucleic acid segment comprising a nucleic acid sequence of interest and at least one cis acting nucleic acid sequence functioning in packaging, reverse transcription and integration of said fourth nucleic acid segment into the genome of a target cell.

23. The transretroviral vector system according to claim 22 wherein said fourth nucleic acid segment further comprises a promoter sequence active in the target cell operably linked to the nucleotide sequence of interest and at least one nucleic acid sequence for facilitating transduction of said fourth nucleic acid segment into the target cell.

24. The transretroviral vector system according to claim 22 wherein said functional portion of said first or said second Gag protein and said protease polypeptide are from a retrovirus.

25. The transretroviral vector system of claim 23 wherein said nucleic acid sequences for facilitating transduction are selected from the group consisting of PPT-CTS and WPRE.

26. The transretroviral vector system according to claim 24 wherein said retrovirus is selected from the group consisting of HIV, SIV, EIAV, BIV, FIV, and MLV.

27. The transretroviral vector system according to any of claims 1, 9, 16, or 22 wherein said first nucleic acid segment further comprises a nucleic acid sequence comprising the Rev Responsive Element.

28. The transretroviral vector system of claim 22, wherein said nucleotide sequence of interest encodes a virus inhibitory polypeptide and said vector in association with a pharmaceutically acceptable carrier.

29. The transretroviral vector system according to any of claims 1, 11, 17, or 22 wherein at least one of said first, second, third, or fourth nucleic acid segment further comprises a gene encoding a marker protein selected from the group consisting of β-gal, fluorescence proteins, and luciferase.

30. The transretroviral vector system of claims 1, 11, 17, or 22, wherein said nucleotide sequence of interest encodes a polypeptide.

31. The transretroviral vector system of claims 5, 12, 18, or 23, wherein said nucleic acid sequences for facilitating transduction are selected from the group consisting of PPT-CTS, WPRE and sequences capable of stabilizing messenger RNAs and increasing the titer of the viral particle.

32. The transretroviral vector system according to any of claims 1, 11, or 17 further comprising promoters operatively linked to at least one of said first, said second, said third or said fourth nucleic acid segments, said promoters selected from the group consisting of HIV promoters, non-HIV promoters, constitutive promoters, and inducible promoters.

33. The transretroviral vector system according to any of claims 1, 11, 17, or 22 further comprising a poly A signal operatively lined to at least one of said first, second, third or fourth nucleic acid segments, said poly A signal selected from the group consisting of non HIV poly A, SV40 poly A, and non-lentiviral poly A.

34. The transretroviral vector system according to claim 30, wherein said protein is selected from the group consisting of a viral inhibitory protein and a therapeutic protein.

35. The transretroviral vector system according to claim 30 wherein said nucleotide sequence of interest encodes a protein selected from the group consisting of neomycin, hygromycin, and puromycin.

36. A method for generating a transretroviral vector comprising:
   (a) providing at least a first nucleic acid segment encoding at least one fusion protein comprising at least a functional portion of a first truncated Gag protein fused in frame to a functional portion of a reverse transcriptase polypeptide having reverse transcriptase activity fused in frame to a functional portion of an integrase polypeptide having integrase activity, said first segment capable of expression in a mammalian cell, said functional portion of said Gag polypeptide capable of providing for the incorporation of said fusion protein into a viral particle;
   (b) providing at least a second nucleic acid segment comprising a nucleic acid sequence encoding at least a functional portion of a second Gag polypeptide and a functional portion of a protease polypeptide, said second nucleic acid segment provided on the same or a different nucleic acid strand than said first segment, said second nucleic acid segment capable of expression in a mammalian cell, said functional portion of said second Gag polypeptide and said protease polypeptide are capable of supporting the formation of an infectious viral particle, and wherein said second nucleic acid segment does not encode a functional Reverse Transcriptase polypeptide or a functional Integrase polypeptide;
   (c) providing at least a third nucleic acid segment comprising nucleic acid sequence encoding an envelope polypeptide, said segment provided on a different or same nucleic acid strand as said first or said second nucleic acid segments;
   (d) contacting said nucleic acid segments of (a), (b), and (c) with the mammalian cell, said mammalian cell becoming transfected with said first, said second, and said third nucleic acid segment; and, (e) producing viral particles from said mammalian cell, said viral particles containing said fusion protein.

37. The method according to claim 36 further comprising providing at least a fourth nucleic acid segment comprising a nucleic acid sequence of interest and at least one cis acting nucleic acid sequence functioning in packaging, reverse transcription and integration of said fourth nucleic acid segment into the genome of a target cell.

38. The method according to claim 37 wherein said fourth nucleic acid segment further comprises a promoter active in said target cell and operably linked to said nucleotide sequence of interest and at least one nucleic acid sequence for facilitating transduction of said fourth nucleic acid segment into the target cell.

39. The method according to claim 38 wherein said nucleic acid sequence for facilitating transduction are selected from the group consisting of PPT-CTS and WPRE.

40. A method for generating a transretroviral vector comprising:

(a) providing at least a first nucleic acid segment encoding at least one fusion protein comprising at least a functional portion of a first truncated Gag protein fused in frame to a functional portion of a reverse transcriptase polypeptide having reverse transcriptase activity fused in frame to a functional portion of an integrase polypeptide having integrase activity, said segment capable of expression in a mammalian cell, said functional portion of said first Gag polypeptide capable of providing for the incorporation of said fusion protein into a viral particle;

(b) providing at least a second nucleic acid segment encoding at least a functional portion of a second Gag polypeptide and a functional portion of a protease polypeptide, said second nucleic acid segment provided on the same or a different nucleic acid strand than said first segment, said second nucleic acid segment capable of expression in the mammalian cell, said functional portion of said second Gag polypeptide and said protease polypeptide are capable of supporting the formation of an infectious viral particle and wherein said second nucleic acid segment does not encode a functional Reverse Transcriptase polypeptide or a functional integrase polypeptide;

(c) providing at least a third nucleic acid segment comprising a nucleic acid sequence of interest and at least one cis acting nucleic acid sequence for packaging, reverse transcription and integration of said third nucleic acid segment into the genome of a target cell;

(d) contacting said nucleic acids of (a), (b), and (c) with the mammalian cell, said mammalian cell becoming transfected with said first, said second, and said third nucleic acid segment; and, (e) producing viral particles from said mammalian cell, said particles containing said fusion protein.

41. The method according to claim 40 further comprising providing at least a fourth nucleic acid segment comprising a nucleic acid sequence encoding an envelope polypeptide, said segment provided on a different or same nucleic acid strand as said first, said second, or said third nucleic acid segment.

42. The method according to claim 40 wherein said third segment further comprises a promoter sequence active in said target cell and operably linked to said nucleotide sequence of interest and at least one nucleic acid sequence for facilitating transduction of said third segment into said target cell.

43. The method according to claim 42 wherein said nucleic acid sequence for facilitating transduction is selected from the group consisting of PPT-CTS and WPRE.

44. The method of claims 38 or 42, wherein said nucleic acid sequences for facilitating transduction are selected from the group consisting of PPT-CTS, WPRE and sequences capable of stabilizing messenger RNAs and increasing he titer of the viral particle.

45. A method for generating a transretroviral vector comprising:

(a) providing at least a first nucleic acid segment encoding at least one fusion protein comprising at least a functional portion of a first truncated Gag protein fused in frame to a functional portion of a reverse transcriptase polypeptide having reverse transcriptase activity fused in frame to a functional portion of an integrase polypeptide having integrase activity, said first nucleic acid segment capable of expression in a mammalian cell, said functional portion of said first Gag polypeptide capable of providing for the incorporation of said fusion protein into a viral particle;

(b) providing at least a second nucleic acid segment comprising a nucleic acid sequence encoding at least a functional portion of a second Gag polypeptide and a functional portion of a protease polypeptide, said second nucleic acid segment provided on the same or a different nucleic acid strand than said first segment, said second segment capable of expression in said mammalian cell, said functional portion of said second Gag polypeptide and a protease polypeptide are capable of supporting the formation of an infectious viral particle and wherein said second nucleic acid segment does not encode a functional Reverse Transcriptase polypeptide or a functional Integrase polypeptide;

(c) providing at least a third nucleic acid segment comprising a nucleic acid sequence encoding an envelope polypeptide, said segment provided on a different or same nucleic acid strand as said first or said second nucleic acid segments;

(d) providing at least a fourth nucleic acid segment comprising a nucleic acid sequence of interest and at least one cis acting nucleic acid sequence functioning in packaging, reverse transcription and integration of said fourth nucleic acid segment into the genome of a target cell;

(e) contacting said nucleic acid segment of (a), (b), (c) and (d) with the mammalian cell, said mammalian cell becoming tranfected with said nucleic acids; and, (f) producing viral particles from said mammalian cell, said particles containing said fusion protein.

46. The method according to claim 45 wherein said fourth nucleic acid segment further comprises a promoter sequence active in said target cell and operably linked to the nucleotide sequence of interest and at least one nucleic acid sequence for facilitating transduction of said fourth segment into the target cell.

47. The method according to claim 36, 40, or 45 wherein said first nucleic acid segment further comprises a Rev Responsive Element (RRE).

48. The method of claim 45 wherein said nucleotide sequence of interest encodes a viral inhibitory protein and said vector is in association with a pharmaceutically acceptable carrier.

49. The method of claims 37 or 45 wherein at least one of said first, said second, said third, or said fourth nucleic acid segment further comprise a nucleic acid sequence encoding a marker protein, said marker protein selected from the group consisting of β-gal, fluorescence proteins, and luciferase.

50. The method of claims 37 or 45 wherein said first, said second, said third, and said fourth nucleic acid segment further comprise a promoter active in said mammalian cell operatively linked to at least one of said first, said second, said third, and said fourth nucleic acid segments, said promoter selected from the group consisting of HIV promoters, non-HIV promoters, constitutive promoters, and inducible promoters.

51. The method of claims 37 or 45 wherein at least one of said first, said second, said third, or said fourth nucleic acid segment further comprise providing a poly A signal operatively linked to at least one of said first, second, third, or fourth nucleic acid segments, said poly A signal selected from the group consisting of non HIV poly A, SV40 poly A, and non-lentiviral poly A.

52. The method of claims 37 or 45, wherein said nucleotide sequence of interest encodes a polypeptide.

53. The method according to claim 46 wherein said nucleic acid sequence for facilitating transduction are selected from the group consisting of PPT-CTS and WPRE.

54. The method of claim 52 wherein said nucleotide sequence of interest encodes a viral inhibitory protein or a therapeutic protein.

55. The method of claim 52 wherein said nucleotide sequence of interest encodes at least one drug resistant protein selected from the group consisting of neomycin, hygromycin, and puromycin.

56. A transretroviral vector system comprising:
at least a first nucleic acid segment encoding a first fusion protein comprising at least a functional portion of a first truncated Gag protein fused in frame to a functional portion of a Reverse Transcriptase polypeptide having reverse transcriptase activity; and,
at least a second nucleic acid segment encoding a second fusion protein comprising at least a functional portion of a second truncated Gag protein fused in frame to a functional portion of an Integrase polypeptide having integrase activity;
wherein said first and said second nucleic acid segment capable of expression in a mammalian cell; said functional portion of said first and said second Gag protein is capable of providing for the incorporation of said first and said second fusion protein into a viral particle; and, said first and said second nucleic acid sequences provided on the same or different nucleic acid strand.

57. The transretroviral vector system of claim 56 further comprising:
at least a third nucleic acid segment comprising a nucleic acid sequence encoding at least a functional portion of a third Gag polypeptide and a functional portion of a protease polypeptide, wherein said third nucleic acid segment provided on the same or a different nucleic acid strand than said first or said second segment; said third nucleic acid segment capable of expression in said mammalian cell; said functional portion of said third Gag polypeptide and said protease polypeptide are capable of supporting the formation of an infectious viral particle and said third nucleic acid segment does not encode a functional Reverse Transcriptase polypeptide or a functional Integrase polypeptide.

58. The transretroviral vector system according to claim 57 further comprising at least a fourth nucleic acid segment comprising a nucleic acid sequence encoding an envelope polypeptide, said fourth nucleic acid segment provided on a different or the same nucleic acid strand as said first, said second, or said third nucleic acid segments.

59. The transretroviral vector system according to claim 58 further comprising at least a fifth nucleic acid segment comprising a nucleic acid sequence of interest and at least one cis acting nucleic acid sequence functioning in packaging, reverse transcription and integration of said fifth nucleic acid segment into the genome of a target cell.

60. The transretroviral vector system according to claim 59 wherein said fifth nucleic acid segment further comprises a promoter active in the target cell and operably linked to the nucleotide sequence of interest and at least one nucleic acid sequence for facilitating transduction of said fifth nucleic acid segment into the target cell.

61. The transretroviral vector of claim 60 wherein said nucleic acid sequences for facilitating transduction are selected from the group consisting of PPT-CTS and WPRE.

62. The transretroviral vector system according to any of claims 57, 58, and, 59 wherein said functional portions of said first, said second, said third Gag polypeptide and said protease polypeptide are from a retrovirus.

63. The transretroviral vector system according to claim 62 wherein said retrovirus is selected from the group consisting of HIV, SIV, EIAV, BIV, FIV, and MLV.

64. A transretroviral vector system comprising:
(a) at least a first nucleic acid segment encoding a first fusion protein comprising at least a functional portion of a first truncated Gag protein fused in frame to a functional portion of a Reverse Transcriptase polypeptide having reverse transcriptase activity; and,
at least a second nucleic acid segment encoding a second fusion protein comprising at least a functional portion of a second truncated Gag protein fused in frame to a functional portion of an Integrase polypeptide having integrase activity;
wherein said first and said second nucleic acid segment capable of expression in a mammalian cell; said functional portion of said first and said second Gag protein are capable of providing for the incorporation of said first and said second fusion protein into a viral particle; and, said first and said second nucleic acid sequences provided on the same or different nucleic acid strand;
(b) at least a third nucleic acid segment comprising a nucleic acid sequence encoding at least a functional portion of a third Gag polypeptide and a functional portion of a protease polypeptide, wherein,
said third nucleic acid segment provided on the same or a different nucleic acid strand than said first or said second nucleic acid segment; said third nucleic acid segment capable of expression in said mammalian cell; said functional portion of said third Gag polypeptide and said protease polypeptide are capable of supporting the formation of an infectious viral particle; and, wherein said third nucleic acid segment does not encode a functional Reverse Transcriptase polypeptide or a functional Integrase polypeptide.

65. The transretroviral vector system according to claim 64 further comprising at least a fourth nucleic acid segment comprising a nucleic acid sequence encoding an envelope polypeptide, said fourth nucleic acid segment provided on a different or the same nucleic acid strand as said first, said second, or said third nucleic acid segments.

66. The transretroviral vector system according to claim 65 further comprising at least a fifth nucleic acid segment comprising a nucleic acid sequence of interest and at least one cis acting nucleic acid sequence functioning in packaging, reverse transcription and integration of said fifth nucleic acid segment into the genome of a target cell.

67. The transretroviral vector system according to claim 66 wherein said fifth nucleic acid segment further comprises a promoter active in the target cell and operably linked to the nucleotide sequence of interest and at least one nucleic acid sequence for facilitating transduction of said fifth segment into the target cell.

68. The transretroviral vector system according to any of claims 64. 65, or 66 wherein said functional portions of said first, said second, and said third Gag protein and said protease polypeptide are from a retrovirus.

69. The transretroviral viral vector of claim 67 wherein said nucleic acid sequences for facilitating transduction are selected from the group consisting of PPT-CTS and WPRE.

70. The transretroviral vector system according to claim 68 wherein said retrovirus is selected from the group consisting of HIV, SIV, EIAV, BIV, FIV, and MLV.

71. A transretroviral vector system comprising:
(a) at least a first nucleic acid segment encoding a first fusion protein comprising at least a functional portion of a first truncated Gag protein fused in frame to a functional portion of a Reverse Transcriptase polypeptide having reverse transcriptase activity; and,
at least a second nucleic acid segment encoding a second fusion protein comprising at least a functional portion of a second truncated Gag protein fused in frame to a functional portion of an Integrase polypeptide having integrase activity;
wherein said first and said second nucleic acid segment capable of expression in a mammalian cell; said functional portion of said first and said second Gag protein capable of providing for the incorporation of said first and said second fusion protein into a viral particle; and, said first and said second nucleic acid sequences provided on the same or different nucleic acid strand;
(b) at least a third nucleic acid segment comprising a nucleic acid sequence encoding at least a functional portion of a third Gag polypeptide and a functional portion of a protease polypeptide, wherein,
said third nucleic acid segment provided on the same or a different nucleic acid strand than said first or said second nucleic acid segment; said third nucleic acid segment capable of expression in said mammalian cell; said functional portion of said third Gag polypeptide and said protease polypeptide are capable of supporting the formation of an infectious viral particle; and, wherein said third nucleic acid segment does not encode a functional Reverse Transcriptase polypeptide or a functional Integrase polypeptide; and,
(c) at least a fourth nucleic acid segment comprising a nucleic acid sequence encoding an envelope polypeptide, said fourth nucleic acid segment provided on a different or the same nucleic acid strand as said first, said second, said third, or said fourth nucleic acid segment.

72. The transretroviral vector system according to claim 71 further comprising at least a fifth nucleic acid segment comprising a nucleic acid sequence of interest and at least one cis acting nucleic acid sequence functioning in packaging, reverse transcription and integration of said fifth nucleic acid segment into the genome of a host cell.

73. The transretroviral vector system according to any of claims 71 or 72 wherein said functional portions of said first, said second, said third Gag protein and said protease polypeptide are from a retrovirus.

74. The transretroviral vector system according to claim 72 wherein said fifth nucleic acid segment further comprises a promoter active in the target cell and operably linked to the nucleotide sequence of interest and at least one nucleic acid sequence for facilitating transduction of said fifth segment into the target cell.

75. The transretroviral vector of claim 74 wherein said nucleic acid sequences for facilitating transduction are selected from the group consisting of PPT-CTS and WPRE.

76. The transretroviral vector system according to claim 73 wherein said retrovirus is selected from the group consisting of HIV, SIV, EIAV, BIV, FIV, and MLV.

77. A transretroviral vector system comprising:
(a) at least a first nucleic acid segment encoding a first fusion protein comprising at least a functional portion of a first truncated Gag protein fused in frame to a functional portion of a Reverse Transcriptase polypeptide having reverse transcriptase activity; and,
at least a second nucleic acid segment encoding a second fusion protein comprising at least a functional portion of a second truncated Gag protein fused in frame to a functional portion of an Integrase polypeptide having integrase activity;
wherein said first and said second nucleic acid segment capable of expression in a mammalian cell; said functional portion of said first and said second Gag protein capable of providing for the incorporation of said first and said second fusion protein into a viral particle; and, said first and said second nucleic acid sequences provided on the same or different nucleic acid strand;
(b) at least a third nucleic acid segment comprising a nucleic acid sequence encoding at least a functional portion of a third Gag polypeptide and a functional portion of a protease polypeptide, wherein,
said third nucleic acid segment provided on the same or a different nucleic acid strand than said first or said second nucleic acid segment; said third nucleic acid segment capable of expression in said mammalian cell; said functional portion of said third Gag polypeptide and said protease polypeptide are capable of supporting the formation of an infectious viral particle; and, wherein said third nucleic acid segment does not encode a functional Reverse Transcriptase polypeptide or a functional Integrase polypeptide; and,
(c) at least a fourth nucleic acid segment comprising a nucleic acid sequence encoding an envelope polypeptide, said fourth nucleic acid segment provided on a different or the same nucleic acid strand as said first, said second, said third, or said fourth nucleic acid segment; and,
(d) at least a fifth nucleic acid segment comprising a nucleic acid sequence of interest and at least one cis acting nucleic acid sequence functioning in packaging, reverse transcription and integration of said fifth nucleic acid segment into the genome of a target cell.

78. The transretroviral vector system according to claim 77 wherein said fifth nucleic acid segment further comprises a promoter active in the target cell operably linked to said nucleotide sequence of interest and at least one nucleic acid sequence for facilitating transduction of said fifth nucleic acid segment into the target cell.

79. The transretroviral vector system according to claim 77 wherein said functional portion of said first, said second or said third Gag protein and said protease polypeptide are from a retrovirus.

80. The transretroviral vector system according to any of claims 56, 64, 71, or 77 wherein said first and said second nucleic acid segment further comprises a nucleic acid sequence comprising a Rev Responsive Element (RRE).

81. The transretroviral vector system according to any of claims 59, 66, 72, or 77 wherein at least one of said first, second, third, fourth or fifth nucleic acid segment further comprises a nucleotide sequence encoding a marker protein selected from the group consisting of β-gal, fluorescence proteins, and luciferase.

82. The transretroviral vector system according to claim 79 wherein said retrovirus is selected from the group consisting of HIV, SIV, EIAV, BIV, FIV, and MLV.

83. The transretroviral vector of claim 78 wherein said nucleic acid sequences for facilitating transduction are selected from the group consisting of PPT-CTS and WPRE.

84. The transretroviral vector system according to any of claims 59, 66, or 72 further comprising promoters operatively linked to at least one of said first, said second, said third, said fourth, or said fifth nucleic acid segments, said promoters selected from the group consisting of HIV promoters, non-HIV promoters, constitutive promoters, and inducible promoters.

85. The transretroviral vector system according to any of claims 59, 66, 72, or 77 further comprising a poly A signal operatively linked to at least one of said first, second, third, fourth or fifth nucleic acid segments, said poly A signal selected from the group consisting of non HIV poly A, SV40 poly A, and non-lentiviral poly A.

86. The transretroviral vector system of claims 59, 66, 72, or 77, wherein said nucleotide sequence of interest encodes a polypeptide.

87. The transretroviral vector system of claims 60, 67, 74, or 78, wherein said nucleic acid sequences for facilitating transduction are selected from the group consisting of PPT-CTS, WPRE and sequences capable of stabilizing messenger RNAs and increasing the titer of the viral particle.

88. The transretroviral vector system according to claim 86 wherein said nucleotide sequence of interest encodes a protein which confers resistance to bacteria and is selected from the group consisting of neomycin, hygromycin, and puromycin.

89. The transretroviral vector system according to claim 86, wherein said nucleotide sequence of interest encodes a polypeptide selected from the group consisting of a viral inhibitory protein and a therapeutic protein.

90. A method for generating a transretroviral vector comprising:
 (a) providing at least a first nucleic acid segment encoding a first fusion protein comprising at least a functional portion of a first truncated Gag protein fused in frame to a functional portion of a Reverse Transcriptase polypeptide having reverse transcriptase activity; and, providing at least a second nucleic acid segment encoding a second fusion protein comprising at least a functional portion of a second truncated Gag protein fused in frame to a functional portion of an Integrase polypeptide having integrase activity; wherein said first and said second nucleic acid segment capable of expression in a mammalian cell; said functional portion of said first and said second Gag protein capable of providing for the incorporation of said first and said second fusion protein into a viral particle; and, said first and said second nucleic acid sequences provided on the same or different nucleic acid strand;
 (b) providing at least a third nucleic acid segment comprising a nucleic acid sequence encoding at least a functional portion of a third Gag polypeptide and a functional portion of a protease polypeptide, wherein, said third nucleic acid segment provided on the same or a different nucleic acid strand than said first or said second nucleic acid segment; said third nucleic acid segment capable of expression in said mammalian cell; said functional portion of said third Gag polypeptide and said protease polypeptide are capable of supporting the formation of an infectious viral particle; and, wherein said third nucleic acid segment does not encode a functional Reverse Transcriptase polypeptide or a functional Integrase polypeptide; and,
 (c) providing at least a fourth nucleic acid segment comprising a nucleic acid sequence encoding an envelope polypeptide, said fourth nucleic acid segment provided on a different or the same nucleic acid strand as said first, said second, said third, or said fourth nucleic acid segment; and,
 (d) contacting said nucleic acid segments of (a), (b), and (c) with the mammalian cell, said mammalian cell becoming transfected with said first, said second, said third, and said fourth nucleic acid segment; and,
 (e) providing viral particles from said mammalian cell, said viral particles containing said first and said second fusion protein.

91. The method according to claim 90 further comprising providing at least a fifth nucleic acid segment comprising a nucleic acid sequence of interest and at least one cis acting nucleic acid sequence functioning in packaging, reverse transcription and integration of said fifth nucleic acid segment into the genome of a target cell.

92. The method according to claim 91 wherein said fifth nucleic acid segment further comprises a promoter active in said target cell and operably linked to said nucleotide sequence of interest and at least one nucleic acid sequence for facilitating transduction of said fifth nucleic acid segment into the target cell.

93. The method according to claim 92 wherein said nucleic acid sequence for facilitating transduction are selected from the group consisting of PPT-CTS and WPRE.

94. A method for generating a transretroviral vector system comprising:
 (a) providing at least a first nucleic acid segment encoding a first fusion protein comprising at least a functional portion of a first truncated Gag protein fused in frame to a functional portion of a Reverse Transcriptase polypeptide having reverse transcriptase activity; and, providing at least a second nucleic acid segment encoding a second fusion protein comprising at least a functional portion of a second truncated Gag protein fused in frame to a functional portion of an Integrase polypeptide having integrase activity; wherein said first and said second nucleic acid segment capable of expression in a mammalian cell; said functional portion of said first and said second Gag protein capable of providing for the incorporation of said first and said second fusion protein into a viral particle; and, said first and said second nucleic acid sequences provided on the same or different nucleic acid strand;
 (b) providing at least a third nucleic acid segment comprising a nucleic acid sequence encoding at least a functional portion of a third Gag polypeptide and a functional portion of a protease polypeptide, wherein, said third nucleic acid segment provided on the same or a different nucleic acid strand than said first or said second nucleic acid segment; said third nucleic acid segment capable of expression in said mammalian cell; said functional portion of said third Gag polypeptide and said protease polypeptide are capable of supporting the formation of an infectious viral particle; and, wherein said third nucleic acid segment does not encode a functional Reverse Transcriptase polypeptide or a functional Integrase polypeptide;

(c) providing at least a fourth nucleic acid segment comprising a nucleic acid sequence of interest and at least one cis acting nucleic acid sequence functioning in packaging, reverse transcription and integration of said fourth nucleic acid segment into the genome of a target cell;

(d) contacting said nucleic acids of (a), (b), and (c) with the mammalian cell, said mammalian cell becoming transfected with said first, said second, said third and said fourth nucleic acid segment; and, (e) providing viral particles from said mammalian cell, said particles containing said first and said second fusion protein.

95. The method according to claim 94 further comprising providing at least a fifth nucleic acid segment comprising a nucleic acid sequence encoding an envelope polypeptide, said segment provided on a different or same nucleic acid strand as said first, said second, said third, or said forth nucleic acid segment.

96. The method according to claim 94 wherein said fourth segment further comprises a promoter active in said target cell and operably linked to said nucleotide sequence of interest and at least one nucleic acid sequence for facilitating transduction of said fourth segment into said target cell.

97. The method according to claim 96 wherein said nucleic acid sequence for facilitating transduction are selected from the group consisting of PPT-CTS and WPRE.

98. A method for generating a transretroviral vector comprising:

(a) providing at least a first nucleic acid segment encoding a first fusion protein comprising at least a functional portion of a first truncated Gag protein fused in frame to a functional portion of a Reverse Transcriptase polypeptide having reverse transcriptase activity; and, providing at least a second nucleic acid segment encoding a second fusion protein comprising at least a functional portion of a second truncated Gag protein fused in frame to a functional portion of an Integrase polypeptide having integrase activity;

wherein said first and said second nucleic acid segment capable of expression in a mammalian cell; said functional portion of said first and said second Gag protein capable of providing for the incorporation of said first and said second fusion protein into a viral particle; and, said first and said second nucleic acid sequences provided on the same or different nucleic acid strand;

(b) providing at least a third nucleic acid segment comprising a nucleic acid sequence encoding at least a functional portion of a third Gag polypeptide and a functional portion of a protease polypeptide, wherein, said third nucleic acid segment provided on the same or a different nucleic acid strand than said first or said second nucleic acid segment; said third nucleic acid segment capable of expression in said mammalian cell; said functional portion of said third Gag polypeptide and said protease polypeptide are capable of supporting the formation of an infectious viral particle; and, wherein said third nucleic acid segment does not encode a functional Reverse Transcriptase polypeptide or a functional Integrase polypeptide;

(c) providing at least a fourth nucleic acid segment comprising a nucleic acid sequence encoding an envelope polypeptide, said segment provided on a different or same nucleic acid strand as said first, said second, or said third nucleic acid segments;

(d) providing at least a fifth nucleic acid segment comprising a nucleic acid sequence of interest and at least one cis acting nucleic acid sequence functioning in packaging, reverse transcription and integration of said fifth nucleic acid segment into the genome of a target cell;

(e) contacting said nucleic acids of (a), (b), (c), and (d) with the mammalian cell, said mammalian cell becoming transfected with said first, said second, said third, said fourth and said fifth nucleic acid segment; and, (f) providing viral particles from said mammalian cell, said particles containing said first and said second fusion protein.

99. The method according to claim 98 wherein said fifth nucleic acid segment further comprises a promoter active in said target cell and operably linked to the nucleotide sequence of interest and at least one nucleic acid sequence for facilitating transduction of said fifth segment into the target cell.

100. The method according to claims 90, 94, 98 wherein at least said first or said second nucleic acid segment further comprises a Rev Responsive Element (RRE).

101. The method of claims 91 or 98 wherein at least said first, said second, said third, said fourth or said fifth nucleic acid segment further comprise a nucleic acid sequence encoding a marker protein, said marker protein selected from the group consisting of β-gal, fluorescence proteins, and luciferase.

102. The method of claims 91 or 98 wherein at least said first, said second, said third, said fourth, or said fifth nucleic acid segment further comprise a promoter active in said mammalian cell operatively linked to at least one of said first, said second, said third, said fourth, or said fifth nucleic acid segments, said promoter selected from the group consisting of HIV promoters, non-HIV promoters, constitutive promoters, and inducible promoters.

103. The method of claims 91 or 98 wherein at least said first, said second, said third, said fourth or said fifth nucleic acid segment further comprise providing a poly A signal operatively linked to at least one of said first, second, third, fourth or fifth nucleic acid segments, said poly A signal selected from the group consisting of non HIV poly A, SV40 poly A, and non-lentiviral poly A.

104. The method of claims 91 or 98, wherein said nucleotide sequence of interest encodes a polypeptide.

105. The method of claims 92, 96, or 99, wherein said nucleic acid sequences for facilitating transduction are selected from the group consisting of PPT-CTS, WPRE, and sequences capable of stabilizing messenger RNAs and increasing the titer of the viral particle.

106. The method according to claim 99 wherein said nucleic acid sequence for facilitating transduction are selected from the group consisting of PPT-CTS and WPRE.

107. The method of claim 104 wherein said nucleotide sequence of interest encodes a viral inhibitory protein or a therapeutic protein.

108. The method of claim 104 wherein said nucleotide sequence of interest encodes at least one drug resistant protein selected from the group consisting of neomycin, hygromycin, and puromycin.

* * * * *

UNITED STATES PATENT AND TRADEMARK OFFICE
CERTIFICATE OF CORRECTION

PATENT NO. : 6,555,342 B1
DATED : April 29, 2003
INVENTOR(S) : Kappes et al.

It is certified that error appears in the above-identified patent and that said Letters Patent is hereby corrected as shown below:

Column 3,
Line 44, "$1_{-62U2}$" should read -- $I_{yu2}$ --;
Lines 57 and 58, "BahHI" should read -- BamH1 --.

Column 6,
Line 11, "BgIII" should read -- Bg1II --.

Column 13,
Line 18, "$^{HIV\text{-}t}HXB2D^{gag}$" should read -- $^{IIIV\text{-}1}HXB2D^{gag}$ --;
Line 60, "elevated" should read -- cleaved --.

Column 33,
Line 28, after "vector" insert -- system --;
Line 66, after "transretroviral" insert -- vector --.

Column 34,
Lines 5, 11 and 15, after "transretroviral" insert -- vector --.

Column 35,
Line 1, after "vector" insert -- system --;
Line 67, "claims 1," should read -- claims 4, --.

Column 36,
Lines 5, 14 and 20, "claims l," should read -- claims 4, --.

Column 37,
Line 43, "integrase" should read -- Integrase --.

Column 38,
Line 7, "he" should read -- the --.

Column 40,
Line 15, after "vector" insert -- system --.

Column 41,
Line 13, delete "viral"; after "vector" insert -- system --.

UNITED STATES PATENT AND TRADEMARK OFFICE
CERTIFICATE OF CORRECTION

PATENT NO. : 6,555,342 B1
DATED : April 29, 2003
INVENTOR(S) : Kappes et al.

It is certified that error appears in the above-identified patent and that said Letters Patent is hereby corrected as shown below:

Column 42,
Line 7, after "vector" insert -- system --.

Column 43,
Line 12, after "vector" insert -- system --.

Column 44,
Line 22, "providing" should read -- producing --.

Column 45,
Line 18, "providing" should read -- producing --.

Column 46,
Line 16, "providing" should read -- producing --;
Line 25, after "94," insert -- or --.

Signed and Sealed this

Twenty-third Day of March, 2004

JON W. DUDAS
*Acting Director of the United States Patent and Trademark Office*